(12) United States Patent
Burgey et al.

(10) Patent No.: US 8,598,209 B2
(45) Date of Patent: Dec. 3, 2013

(54) P2X3, RECEPTOR ANTAGONISTS FOR TREATMENT OF PAIN

(75) Inventors: Christopher S. Burgey, Philadelphia, PA (US); Zhengwu J. Deng, Eagleville, PA (US); Diem N. Nguyen, Harleysville, PA (US); Daniel V. Paone, Lansdale, PA (US); Anthony W. Shaw, Harleysville, PA (US); Anthony Ginnetti, Perkasie, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 218 days.

(21) Appl. No.: 13/125,935

(22) PCT Filed: Oct. 21, 2009

(86) PCT No.: PCT/US2009/061409
§ 371 (c)(1),
(2), (4) Date: Apr. 25, 2011

(87) PCT Pub. No.: WO2010/051188
PCT Pub. Date: May 6, 2010

(65) Prior Publication Data
US 2011/0206783 A1 Aug. 25, 2011

Related U.S. Application Data

(60) Provisional application No. 61/197,869, filed on Oct. 31, 2008, provisional application No. 61/227,285, filed on Jul. 21, 2009.

(51) Int. Cl.
*A61K 31/4412* (2006.01)
*C07D 213/24* (2006.01)
*C07D 213/60* (2006.01)

(52) U.S. Cl.
USPC ........................................ 514/336; 546/268.1

(58) Field of Classification Search
USPC ........................................ 546/268.1; 514/336
See application file for complete search history.

(56) References Cited

U.S. PATENT DOCUMENTS

| | | | |
|---|---|---|---|
| 6,096,753 A | 8/2000 | Spohr et al. | |
| 6,410,729 B1 | 6/2002 | Spohr et al. | |
| 6,420,385 B1 | 7/2002 | Spohr et al. | |
| 6,436,972 B1 | 8/2002 | Darvesh et al. | |
| 6,544,986 B2 | 4/2003 | Darvesh et al. | |
| 6,610,698 B2 | 8/2003 | Sphor et al. | |
| 6,649,604 B2 | 11/2003 | Spohr et al. | |
| 6,977,266 B2 | 12/2005 | Tada et al. | |
| 2007/0049609 A1 | 3/2007 | Broka et al. | |
| 2008/0004442 A1 | 1/2008 | Dillion et al. | |
| 2008/0021024 A1 | 1/2008 | Sucholeiki et al. | |

FOREIGN PATENT DOCUMENTS

| | | | |
|---|---|---|---|
| WO | WO9824780 | 6/1998 | |
| WO | WO 98/24780 | * 11/1998 | ........... C07D 401/00 |
| WO | WO0112627 | 2/2001 | |
| WO | WO2006119504 | 11/2006 | |
| WO | WO2007001973 | 1/2007 | |
| WO | WO2007010553 | 1/2007 | |
| WO | WO2007041087 | 4/2007 | |

OTHER PUBLICATIONS

Overman, L. "Dehydrogenase Enzyme Models. Approximation of an alcohol and a pyridinium ring," J. Org. Chem. (1972), pp. 4214-4218.*
G. Burnstock et al., "Physiological and Pathological Roles of Purines: An Update", Drug Development Research., 1993 vol. 28, pp. 195-206., Wiley-Liss, Inc., UK.
S. Valera et al., "A New Class of Ligand-Gated Ion Channel Defined by P2X Receptor for Extracellular ATP", Nature, 1994, vol. 371, pp. 516-519, Nature Publishing Group (United Kingdom).
A. J. Brake et al., "A New Structural Motif for Ligand-Gated Ion Channels defined by an Ionotropic ATP Receptor", Nature, 1994, vol. 371, pp. 519-523, Nature Publishing Group (United Kingdom).
C. Lewis et al., "Coexpression of P2X2 and P2X3 Receptor Subunits can Account for ATP-Gated Currents in Sensory Neurons", Nature, 1995, vol. 377, pp. 432-435, Nature Publishing Group (United Kingdom).
C. Chen et al., "A P2X Purinoceptor Expressed by a Subset of Sensory Neurons", Nature, 1995, vol. 377, pp. 428-431, Nature Publishing Group (United Kingdom).
Buell et al., "An Antagonist-Insensitive P2X Receptor Expressed in Epithelia and Brain", EMBO, 1996, vol. 15, pp. 55-62, Oxford University Press, UK.
P. Seguela et al., "A Novel Neuronal P2X ATP Receptor Ion Channel with Widespread Distribution in the Brain", J. of Neuroscience, 1996, vol. 16, pp. 448-455, Society for Neuroscience, Washington DC.
X. Bo et al., "A P2X Purinoceptor cDNA Conferring a Novel Pharmacological Profile", FEBS Letters, 1995, vol. 375, pp. 129-133, Federation of European Biochemical Societies, Elsevier Science B.V., Amsterdam.
F. Soto et al., "P2X4: An ATP-Activated Ionotropic Receptor Cloned from Rat Brain", Proc. Natl. Acad. Sci., 1996, vol. 93, pp. 3684-3688, USA.
C. Wang et al., "Cloning and Pharmacological Characterization of a Fourth P2X Receptor Subtype Widely Expressed in Brain and Peripheral Tissues Including Various Endocrine Tissues", Biochemical and Biophysical Research Communications, 1996, vol. 220, pp. 196-202, Academic Press.
G. Collo et al., "Cloning of P2X5 and P2X6 Receptors and the Distribution and Properties of an Extended Family of ATP-Gated Ion Channels", J. of Neuroscience, 1996, vol. 16, pp. 2495-2507, Society for Neuroscience, Washington DC.
M. Garcia-Guzman et al., "Molecular Cloning and Functional Expression of a Novel Rat Heart P2X Purinoceptor", FEBS Letters, 1996, vol. 388, pp. 123-127, Federation of European Biochemical Societies, Elsevier Science B.V., Amsterdam.

(Continued)

*Primary Examiner* — Kamal Saeed
*Assistant Examiner* — Janet L. Coppins
(74) *Attorney, Agent, or Firm* — Sylvia A. Ayler; Gerard M. Devlin

(57) ABSTRACT

The subject invention relates to novel P2X$_3$ receptor antagonists that play a critical role in treating disease states associated with pain, in particular peripheral pain, inflammatory pain, or tissue injury pain that can be treated using a P2X$_3$ receptor subunit modulator.

16 Claims, No Drawings

(56) References Cited

OTHER PUBLICATIONS

F. Soto et al., "Cloning and Tissue Distribution of a Novel P2X Receptor from Rat Brain", Biochemical and Biopysical Research Communications, 1996, vol. 223, pp. 456-460, Academic Press.

A. Surprenant et al., "The Cytolytic P2z Receptor for Extracellular ATP Identified as a P2x Receptor (P2X7)", Science, 1996, vol. 272, pp. 735-738, Elsevier.

G. Buell et al., "P2X Receptors: An Emerging Channel Family", E. Journal of Neuroscience, 1996, vol. 8, pp. 2221-2228, Wiley-Blackwell.

K. Le et al., "Central P2X4 and P2X6 Channel Subunits Coasssemble into a Novel Heteromeric ATP Receptor", J. of Neuroscience, 1998, vol. 18, pp. 7152-7159, Wiley-Blackwell.

G. Torres et al., "Co-Expression of P2X1 and P2X5 Receptor Subunits Reveals a Novel ATP-Gated Ion Channel", Mol. Pharmacol., 1998, vol. 54, pp. 989-993, American Society for Pharmacology and Experimental Therapeutics.

P. A. Bland-Ward et al., "Acute Nociception Mediated by Hindpaw P2X Receptor Activation in the Rat", British J. of Pharmacology, 1997, vol. 122, pp. 365-371, Stockton Press.

S. Hamilton et al., "The Effects of Inflammation and Inflammatory Mediators on Nociceptive Behaviour Induced by ATP Analogues in the Rat", British J. of Pharmacology, 1999, vol. 126, pp. 326-332, Stockton Press.

B. Driessen et al., "Antinociceptive Effect of Intrathecally Administered P2-Purinoceptor Antagonists in Rats", Brain Research, 1994, vol. 666 pp. 182-188, Elsevier Science.

M. Tsuda et al., "In Vivo Pathway of Thermal Hyperalegesia by Intrathecal Administration of Alpha, Beta-Methylene ATP in Mouse Spinal Cord: Involvement of the Glutamate-NMDA Receptor System", Br. J. Pharmacol., 1999, vol. 127, pp. 449-456, Stockton Press.

M. Tsuda et al., "Evidence for the Involvement of Spinal Endogenous ATP and P2X Receptors in Nociceptive Responses Caused by Formalin and Capsaicin in Mice", B. J. of Pharmacology, 1999, vol. 18, pp. 1497-1504, Stockton Press.

Y. Chen et al., "Ectopic Purinergic Sensitivity Develops at Sites of Chronic Nerve Constriction Injury in Rat", NeuroReport, 1999, vol. 10, pp. 2779-2782, Lippincot Williams & Wilkins.

L. Vulchanova et al., "Immunohistochemical Study of the P2X2 and P2X3 Receptor Subunits in Rat and Monkey Sensory Neurons and Their Central Terminals", Neuropharmacology, 1997, vol. 36, No. 9, pp. 1229-1242, Elsevier Science Ltd., Great Britain.

G. Burnstock et al., "Relase of Vasoactive Substances from Endothelial Cells by Shear Stress and Purinergic Mechanosensory Transduction", J. Anat., 1999, vol. 194, pp. 335-342, Autonomic Neuroscience Institute, UK.

D.R. Ferguson et al., "ATP is released from Rabbit Urinary Bladder Epithelial Cells by Hydrostatic Pressure Changes, A Possible Sensory Mechanism?", J. of Physiology, 1997, vol. 505, pp. 503-511.

V. Ralevic et al., "Receptors and Purines and Pyrimidines", Pharmacological Reviews, 1998, vol. 50, pp. 413-492, American Society for Pharmacology and Experimental Therapeutics.

S. Namasivayam et al., "Purinergic Sensory Neurotransmission in the Urinary Bladder: An In Vitro Study in the Rat", BJU International, 1999, vol. 84, pp. 854-860, Blackwell Publishing Ltd, UK.

Y. Zhong et al., "Pharmacological and Molecular Characterization of P2X Receptors in Rat Pelvic Ganglion Neurons", British J. of Pharmacology, 1998, vol. 125, pp. 771-781, Stockton Press, UK.

Y. Yiangou et al., "ATP-Gated Ion Channel P2X3 is Increased in Human Inflammatory Bowel Disease", Neurogastroenterol. Mot., 2001, vol. 13, pp. 365-369, Blackwell Science Ltd., UK.

X. Bian et al., "Peristalsis is Impaired in the Small Intestine of Mice Lacking the P2X3 Subunit", J. Physiol., 2003, vol. 551.1, pp. 309-322, John Wiley & Sons, US.

G. Wynn et al., "Purinergic Component of Mechanosensory Transduction is Increased in a Rat Model of Colitis", Am. J. Physiol. ,2004, vol. 287, pp. 647-657, American Physiological Society, US.

I. Brouns et al., "Intraepithelial Vagal Sensory Nerve Terminals in Rat Pulmonary Neuroepithelial Bodies Express P2X3 Receptors", Am. J. Respir. Cell Mol. Biol., 2000, vol. 23, pp. 52-61, American Thoracic Society, US.

W. Rong et al., "Pivotal Role of Nucleotide P2X2 Receptor Subunit of the ATP-Gated Ion Channel Mediating Ventilatory Responses to Hypoxia", J. of Neuroscience, 2003, vol. 23, pp. 11315-11321, Elsevier Science.

Burnstock et al., "A Basis for Distinguishing Two Types of Purinergic Receptor", Cell Membrane Receptors for Drugs and Hormone: A Multidisciplinary Approach, Cell Membrane for Drugs and Hormones, 1978, pp. 107-118, Raven Press, NY.

Burnstock et al., "Purinergic Nerves", Pharmacological Reviews, 1972, vol. 24, No. 3, pp. 509-581, The Williams & Wilkins, Co.

* cited by examiner

P2X3, RECEPTOR ANTAGONISTS FOR TREATMENT OF PAIN

CROSS REFERENCE TO RELATED APPLICATIONS

This application is the National Stage of International Application No. PCT/US2009/061409 filed on Oct. 21, 2009, which claims the benefit under 35 U.S.C. 119(e) of U.S. Provisional Application Nos. 61/197,869, filed Oct. 31, 2008 and 61/227,285 filed Jul. 21, 2009.

FIELD OF THE INVENTION

The invention relates generally to compounds which act as modulators, e.g., antagonists of the P2X$_3$ receptor, compositions and therapeutic uses thereof.

BACKGROUND OF THE INVENTION

Purines, acting via an extracellular purinoreceptor, have been implicated as having a variety of physiological and pathological roles. (See, Burnstock (1993) Drug Dev. Res. 28:195-206.) Purinoreceptors (P2) have been generally categorized as either metabotropic nucleotide receptors or ionotropic receptors for extracellular nucleotides. Metabotropic nucleotide receptors (usually designated P2Y or P2Y$_{(n)}$, where "n" is a subscript integer indicating subtype) are believed to differ from ionotropic receptors (usually designated P2X or P2X$_{(n)}$ in that they are based on a different fundamental means of transmembrane signal transduction: P2Y receptors operate through a G protein-coupled system, while P2X receptors are ligand-gated ion channels.

At least seven P2X receptors, and the cDNA sequences encoding them, have been identified to date. P2X$_1$ cDNA was cloned from the smooth muscle of the rat vas deferens (Valera et al. (1994) Nature 371:516-519) and P2X$_2$ cDNA was cloned from PC12 cells (Brake et al. (1994) Nature 371:519-523). Five other P2X receptors have been found in cDNA libraries by virtue of their sequence similarity to P2X$_1$ and P2X$_2$—P2X$_3$: Lewis et al. (1995) Nature 377:432-435, Chen et al. (1995) Nature 377:428-431; P2X$_4$: Buell et al. (1996) EMBO J. 15:55-62, Seguela et al. (1996) J. Neurosci. 16:448-455, Bo et al. (1995) FEBS Lett. 375:129-133, Soto et al. (1996) Proc. Natl. Acad. Sci. USA 93:3684-3688, Wang et al. (1996) Biochem. Biophys. Res. Commun. 220:196-202; P2X$_5$: Collo et al. (1996) J. Neurosci. 16:2495-2507, Garcia-Guzman et al. (1996) FEBS Lett. 388:123-127; P2X$_6$: Collo et al. (1996), supra, Soto et al. (1996) Biochem. Biophys. Res. Commun. 223:456-460; P2X$_7$: Surprenant et al. (1996) Science 272:735-738). For a comparison of the amino acid sequences of rat P2X receptor see Buell et al. (1996) Eur. J. Neurosci. 8:2221-2228.

Purinergic receptors, in particular, P2X receptors, are known to function as homomultimeric cation-permeable ion channels and, in some cases, as heteromeric channels consisting of two different P2X receptor subtypes (Lewis et al., Nature 377:432-435 (1995); Le et al., J. Neurosci. 18:7152-7159 (1998); Torres et al., Mol. Pharmacol. 54:989-993 (1998)). The P2X$_2$ and P2X$_3$ subunits form functional channels when expressed alone, and can also form a functional heteromultimeric channel that has properties similar to currents seen in native sensory channels when co-expressed. At least one pair of P2X receptor subtypes, P2X$_2$ and P2X$_3$, functions as a heteromeric channel in rat nodose ganglion neurons where it exhibits distinct pharmacological and electrophysiological properties (Lewis et al., supra (1995)).

Native P2X receptors are known to form rapidly activated, nonselective cationic channels upon activation by ATP. The channels formed by P2X receptors generally have high Ca$^{2+}$ permeability (P$_{(Ca)}$/P$_{(Na)}$). With respect to individual receptors, the P2X$_3$ purinergic receptor is a ligand-gated cation channel that is selectively permeable to small cations. Known ligands for P2X receptors include natural nucleotides, for example, ATP, UTP, UDP, or synthetic nucleotides, for example 2-methylthioATP. ATP, in addition to its function as an intracellular energy donor, is now recognized as an important neurotransmitter or cotransmitter, in both the central and peripheral nervous system (Ralevic, V., et al., Pharmacol. Rev., 50:413-492 (1998)). It is released from a variety of cell types, including nerve fibers, upon stimulation and produces diverse effects on many tissues by activation of specific membrane receptors including purinoreceptors (P2 receptor) (See Burnstock, G., Pharmacol. Rev., 24:509-581 (1972); Burnstock, G., Cell Membrane Receptor for Drugs and Hormones: A Multidisciplinary Approach, edited by R. W. Straub and L. Bolid. New York: Raven, 1978, p. 107-118). With respect to the P2X purinergic receptor, data suggest that ATP is capable of activating P2X$_3$ homomeric receptors and P2X$_2$/P2X$_3$ heteromeric receptors where it functions as an excitatory neurotransmitter in the spinal cord dorsal horn and in primary afferents from sensory ganglia. In vitro, co-expression of P2X$_2$ and P2X$_3$ receptor subunits is necessary to produce ATP-gated currents with the properties seen in some sensory neurons. See, Lewis, et al. (1995) Nature 377:432-435.

ATP, and to a lesser extent, adenosine, can stimulate sensory nerve endings resulting in intense pain and a pronounced increase in sensory nerve discharge. According to available data, ATP released from damaged cells can evoke pain by activating P2X$_3$ homomeric receptors, or P2X$_2$/P2X$_3$ heteromeric receptors expressed on nociceptive nerve endings of sensory nerves. This is consistent with reports of the induction of pain by intradermally applied ATP in the human blister-base model; the identification of P2X$_3$ containing receptor on nociceptive neurons in the tooth pulp; and with reports that P2X antagonists are analgesic in animal models. To date, research data suggests that the mechanism whereby ATP-induced activation of the P2X purinergic receptors on dorsal root ganglion nerve terminals in the spinal cord and on neurons in the brain results in pain sensation is by the stimulation of the release of glutamate, a key neurotransmitter involved in nociceptive signaling.

It has also been recently demonstrated that P2X$_3$ receptor gene disruption results in a diminished sensitivity to noxious chemical stimuli and reduced pain. The nociceptive effects of exogenously administered ATP and P2X containing receptor agonists have also been demonstrated in laboratory animals. See Bland-Ward et al., Dr. J. Pharmacol. 122:366-371 (1997); Hamilton et al., Br. J. Phamacol. 126:326-332 (1999). The peripheral nociceptive actions of P2X activation and stimulation of spinal P2X containing receptor also contribute to nociception as indicated by the ability of intrathecally (i.t.) administered P2 receptor agonists to increase sensitivity to acute and persistent noxious stimuli in rodents. See Driessen et al., Brain Res. 666:182-188 (1994); Tsuda et al., Br. J. Pharmacol. 127:449-4S6 (1999); Tsuda et al., Br. J. Pharmacol. 128:1497-1504 (1999). A selective P2 receptor-mediated increase in ectopic neuronal excitability that is localized to damaged sensory afferents has also been recently reported in rats following chronic constriction nerve injury. See Chen et al., NeuroReport 10:2779-2782 (1999). This role in pain transmission is consistent with the observation that the rat P2X$_3$ receptor expression is found primarily in a subset of neurons of the sensory ganglia, which are involved in pain transmission. See Chen et al., Nature 377:428-430 (1995); Vulchanova et al., Neuropharmacol. 36:1229-1242 (1997). See also US20080004442, US200700409609, WO2007041087, WO2006119504, WO200112627, WO2007001973 and WO2007010553.

Taken together, the functional and immunohistochemical localization of $P2X_3$ containing receptors ($P2X_3$ and/or $P2X_{2/3}$) on sensory nerves indicates that these P2X receptors may have a primary role in mediating the nociceptive effects of ATP. Thus, compounds which block or inhibit activation of $P2X_3$ receptors serve to block the pain stimulus. More, receptor antagonists to compounds which normally activate the $P2X_3$ receptor and/or $P2X_2/P2X_3$ heteromeric channels, such as ATP, could successfully block the transmission of pain. Indeed, modulators of P2X receptors, e.g., $P2X_3$ receptor may find use as analgesics.

Additionally, compounds that block or inhibit activation of $P2X_3$ receptors also serve to treat genitourinary, gastrointestinal and respiratory diseases, conditions and disorders or receptor antagonists to compounds which normally activate the $P2X_3$ receptor and/or $P2X_2/P2X_3$ heteromeric channels, such as ATP are useful for treatment of genitourinary, gastrointestinal and respiratory diseases, conditions and disorders.

Burnstock (1999) *J. Anatomy* 194:335-342; and Ferguson et al. (1997) *J. Physiol*. 505:503-511 disclose that P2X receptor subunits have been found on afferents in rodent and human bladder urothelium. There data suggests that ATP may be released from epithelial/endothelial cells of the urinary bladder or other hollow organs as a result of distention. ATP released in this manner may serve a role in conveying information to sensory neurons located in subepithelial components, e.g., suburothelial lamina propria (Namasibayam, et al. (1999) *BJU Intl*. 84:854-860). P2X receptors have been studied in a number of neurons including sensory, sympathetic, parasympathetic, mesenteric, and central neurons (Zhong, et al. (1998) *Br. J. Pharmacol*. 125:771-781). These studies indicate that purinergic receptors play a role in affterent neurotransmission from the bladder, and that modulators of P2X receptors are potentially useful in the treatment of bladder disorders such as urinary incontinence and other genitourinary diseases or conditions.

$P2X_3$ receptors have been shown to be expressed in human colon, and are expressed at higher levels in inflamed colon, than in normal colon (Y. Yiangou et al, *Neurokastroenterol Mot* (2001) 13:365-69). $P2X_3$ receptors have also been implicated in detection of distension or intraluminal pressure in the intestine and initiation of reflex contractions (X. Bian et al. *J. Physiol* (2003) 551.1:309-22), and have linked this to coilitis (G. Wynn et al., *Am J. Physiol Gastrointest Liver Physiol* (2004) 287:G647-57).

$P2X_3$ receptors also have been shown to be expressed in pulmonary neuroepithelial bodies (NEBs), implicating the receptor in pain transmission in the lung (Inge Brouns et al., *Am J. Respir Cell Mol Biol* (2000) 23:52061). Additionally, $P2X_2$ and $P2X_3$ receptors have been implicated in $pO_2$ detection in pulmonary NEBs (W. Rong et al., *J. Neurosci* (2003) 23(36):11315-21).

However, the utility of available purinergic ligands to evaluate the role of individual P2 receptor subtypes in mammalian physiology has been complicated by the susceptibility of P2 receptor agonists to undergo enzymatic degradation. As well, the study of the role of an individual P2X receptor is hampered by the lack of receptor subtype-specific agonists and antagonists.

Consequently, the state of the art begs an inquiry into methods and/or compounds which will provide the ability to regulate or control the P2X receptors, for example, $P2X_3$, because control of such receptors will provide the ability to minimize pain in patients in need of such treatment. In addition, for both research and therapeutic purposes there is a need in the art for specific agonists and antagonists for each P2X receptor subtype and, in particular, agents that will be effective in vivo, as well as for methods for identifying purinoreceptor-specific agonist and antagonist compounds.

See WO9824780, U.S. Pat. No. 6,420,385, U.S. Pat. No. 6,096,753, U.S. Pat. No. 6,410,729, U.S. Pat. No. 6,649,604, U.S. Pat. No. 6,436,972, U.S. Pat. No. 6,544,986, U.S. Pat. No. 6,977,266, and U.S. Pat. No. 6,610,698 for the state of the art regarding compound structures.

The present invention aims to overcome some of the aforementioned drawbacks by providing novel $P2X_3$ receptor antagonists that play a critical role in treating disease states associated with pain, in particular peripheral pain, inflammatory pain, or tissue injury pain that can be treated using a $P2X_3$ receptor subunit modulator.

SUMMARY OF THE INVENTION

The present invention relates to a novel $P2X_3$ type receptor antagonists of structural formula I:

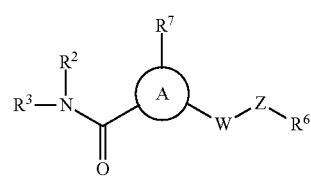

I or pharmaceutically acceptable salts and individual enantiomers and diastereomers thereof wherein:

A represents pyridinyl, pyrimidinyl, or pyridinonyl;

W and Z independently are absent or represent $C(R^2)_2$, —O—, $NR^2$, CO, or $SO_{0-2}$;

$R^2$ represents H, $C_{1-6}$ alkyl, $CF_3$, OH, $CHF_2$, or $CH_2F$;

$R^3$ represents $CR^2R^4R^5$, $(CH_2)_nC_{3-10}$ cycloalkyl, $(CH_2)_n C_{6-10}$ aryl, $(CH_2)_nC_{5-10}$ heterocycle, said cycloalkyl, and heterocyclyl optionally substituted with 1 to 3 groups of $R^a$;

or $R^2$ and $R^3$ can be combined with the nitrogen to which they are attached to form a $C_{5-10}$ heterocyclyl optionally substituted with 1 to 3 groups of $R^a$;

$R^4$ and $R^5$ independently represent H, $(CH_2)_nOR^2$, $CHF_2$, $(CH_2)_nCF_3$, $(CH_2)_nC_{5-10}$ heterocyclyl, $(CH_2)_nC_{6-10}$ aryl, $C_{3-10}$ cycloalkyl, $C_{1-6}$ alkoxy, $C_{2-6}$ alkenyl, $C(O)_{1-2}R^2$, or $C_{1-6}$ alkyl; said alkyl, cycloalkyl, heterocyclyl and aryl optionally substituted with 1 to 3 groups of $R^a$;

$R^6$ represents hydrogen, $OR^2$, —O—, $CF_3$, $C(R^2)_2OR^2$, $C_{1-6}$ alkyl, $C_{2-6}$ alkenyl, $C_{2-6}$ alkynyl, $C_{3-10}$ cycloalkyl, $(CH_2)_n C_{6-10}$ aryl, $(CH_2)_nC_{5-10}$ heterocyclyl, said alkyl, cycloalkyl, aryl and heterocyclyl optionally substituted with 1 to 3 groups of $R^a$;

$R^7$ represents $C_{1-6}$ alkyl, $C_{3-10}$ cycloalkyl, $(CH_2)_nC_{5-10}$ heterocyclyl, or $(CH_2)_nC_{6-10}$ aryl, said alkyl, cycloalkyl, heterocyclyl and aryl optionally substituted with 1 to 3 groups of $R^a$;

$R^a$ represents $C_{1-6}$ alkyl, halogen, hydroxyl, $OR^2$ $(CH_2)_nCF_3$, —O—, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $C(O)OR^2$, $SO_2R^2$, $OR^2$, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN; and n represents 0 to 4, provided that when A is pyrimidinyl WZR⁶ is not OH and when A is pyridinonyl WZR⁶ is not hydrogen.

This invention also relates to compositions and methods for using the compounds disclosed herein. These and other embodiments of the present invention will readily occur to those of ordinary skill in the art in view of the disclosure herein.

DETAILED DESCRIPTION OF THE INVENTION

The present invention relates to a novel P2X₃ type receptor antagonists of structural formula I that are useful in treating pain and diseases associated with pain.

An embodiment of the invention of formula I is realized when R⁷ is C₁₋₆ alkyl optionally substituted with 1 to 3 groups of Rᵃ and all other variables are as previously described.

Another embodiment of the invention of formula I is realized when R⁷ is C₃₋₁₀ cycloalkyl optionally substituted with 1 to 3 groups of Rᵃ and all other variables are as previously described. A sub-embodiment of this invention is realized when the cycloalkyl is cyclopropyl.

Another embodiment of the present invention is realized when R⁷ is (CH₂)ₙC₆₋₁₀ aryl optionally substituted with 1 to 3 groups of Rᵃ and all other variables are as previously described. A sub-embodiment of this invention is realized when the aryl is phenyl. Another sub-embodiment of this invention is realized when n is 0.

Another embodiment of the present invention is realized when R⁷ is optionally substituted (CH₂)ₙC₅₋₁₀ heterocyclyl and all other variables are as previously described. A sub-embodiment of this invention is realized when the heterocyclyl is pyridinyl, morpholinyl, pyrimidinyl, imidazolyl, or oxazolyl optionally substituted with 1 to 3 groups of Rᵃ. Another sub-embodiment of this invention is realized when n is 0.

Still another embodiment of the present invention is realized when R⁷ is represented by structural formula Ia:

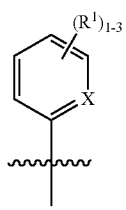

Ia wherein X is N or CH; and R¹ represents H, C₁₋₆ alkyl, halogen, (CH₂)ₙCF₃, C₃₋₁₀ cycloalkyl, C(R²)₂OH, —O—, CN, (CH₂)ₙOR², (CH₂)ₙC₅₋₁₀ heterocyclyl, (CH₂)ₙC₆₋₁₀ aryl, or C₁₋₆ alkoxy; said alkyl, cycloalkyl, heterocyclyl and aryl optionally substituted with 1 to 3 groups of C₁₋₆ alkyl, halogen, hydroxyl, (CH₂)ₙCF₃, or CN. A sub-embodiment of the present invention is realized when X of formula Ia is N and all other variables are as previously described. Another sub-embodiment of the present invention is realized when X of formula Ia is CH and all other variables are as previously described.

Another embodiment of the present invention is realized when formula Ia is linked to a carbon atom on A and all other variables are as previously described.

Yet another embodiment of the present invention is realized when formula Ia is linked to a nitrogen atom on A and all other variables are as previously described.

Another embodiment of the present invention is realized when A is pyridyl and all other variables are as previously described. A subembodiment of this invention is realized when —C(O)NR²R³ and —WZR⁶ are independently attached to carbon atoms on A.

Another embodiment of the present invention is realized when A is pyridyl, —C(O)NR²R³ is attached to a carbon atom on A and —WZR⁶ is attached to a nitrogen atom on A.

Another embodiment of the present invention is realized when A is pyrimidinyl and all other variables are as previously described. A subembodiment of this invention is realized when —C(O)NR²R³ and —WZR⁶ are independently attached to carbon atoms on A.

Another embodiment of the present invention is realized when A is pyridinonyl and all other variables are as previously described. A subembodiment of this invention is realized when —C(O)NR²R³ and —WZR⁶ are independently attached to carbon atoms on A. Another subembodiment of this invention is realized when —WZR⁶ is attached to the nitrogen atom on A and —C(O)NR²R³ is attached to a carbon atom on A. Yet another embodiment of this invention is realized when formula Ia is attached to a carbon atom on A. Still another embodiment of this invention is realized when formula Ia is attached to the nitrogen atom on A. Yet another embodiment of this invention is realized when the =O of the pyridinonyl is ortho to the bond linking A to formula Ia.

Another embodiment of the present invention is realized when W and Z both are absent. Still another embodiment of this invention is realized when R⁶ is hydrogen, OR², C₁₋₆ alkyl, C₃₋₁₀ cycloalkyl, (CH₂)ₙC₆₋₁₀ aryl, (CH₂)ₙC₅₋₁₀ heterocyclyl, said alkyl, cycloalkyl, aryl and heterocyclyl optionally substituted with 1 to 3 groups of Rᵃ. A subembodiment of this invention is realized when R⁶ is hydrogen, C₁₋₆ alkyl, OR², (CH₂)ₙmorpholinyl, (CH₂)ₙpyridyl, (CH₂)ₙpiperidinyl, (CH₂)ₙoxazolyl, (CH₂)ₙisoxazolyl, (CH₂)ₙphenyl, (CH₂)ₙimidazolyl, (CH₂)ₙpyrimidinyl, cyclopropyl, cyclobutyl, preferably hydrogen, (CH₂)ₙpyridyl, (CH₂)ₙmorpholinyl, (CH₂)ₙphenyl, C₁₋₆ alkyl, cyclopropyl, all optionally substituted with 1 to 3 groups of Rᵃ. A further sub-embodiment of this invention is realized when R⁶ is hydrogen, C₁₋₆ alkyl, OR², (CH₂)ₙmorpholinyl, (CH₂)ₙpyridyl, (CH₂)ₙphenyl, or (CH₂)ₙpyrimidinyl.

Another embodiment of the present invention is realized when W and Z both are absent, and R⁶ is an —O— linked to a nitrogen on the ring.

Still another embodiment of this invention is realized when one of W and Z is absent and the other is —O—, or NR². Still another embodiment of this invention is realized when R⁶ is hydrogen, OR², C₁₋₆ alkyl, C₃₋₁₀ cycloalkyl, (CH₂)ₙC₆₋₁₀ aryl, (CH₂)ₙC₅₋₁₀ heterocyclyl, said alkyl, cycloalkyl, aryl and heterocyclyl optionally substituted with 1 to 3 groups of Rᵃ. A subembodiment of this invention is realized when R⁶ is hydrogen, C₁₋₆ alkyl, OR², (CH₂)ₙmorpholinyl, (CH₂)ₙpyridyl, (CH₂)ₙpiperidinyl, (CH₂)ₙoxazolyl, (CH₂)ₙisoxazolyl, (CH₂)ₙphenyl, (CH₂)ₙimidazolyl, (CH₂)ₙpyrimidinyl, cyclopropyl, cyclobutyl, preferably hydrogen, (CH₂)ₙpyridyl, (CH₂)ₙmorpholinyl, (CH₂)ₙphenyl, C₁₋₆ alkyl, cyclopropyl, all optionally substituted with 1 to 3 groups of Rᵃ.

Another embodiment of the present invention is realized when R² is hydrogen and all other variables are as previously described.

Still another embodiment of this invention is realized when R³ is (CH₂)ₙC₃₋₁₀ cycloalkyl and all other variables are as previously described.

Still another embodiment of this invention is realized when R³ is CR²R⁴R⁵ and all other variables as previously described. A subembodiment of this invention is realized when $R^2$ of $CR^2R^4R^5$ is hydrogen. A subembodiment of this invention is realized when one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. A further subembodiment of this invention is realized when said aryl and heterocyclyl is $(CH_2)_n$phenyl, $(CH_2)_n$pyridyl, $(CH_2)_n$pyrimidinyl, $(CH_2)_n$triazolyl, pyrazinyl, or $(CH_2)_n$oxadiazolyl.

Another subembodiment of this invention is realized when $R^3$ is $CR^2R^4R^5$, which is an alkyl optionally substituted with 1 to 3 groups of $R^a$ and all other variables are as previously described. A subembodiment of this invention is realized when $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. Another subembodiment of this invention is realized when $R^2$ of $CR^2R^4R^5$ is hydrogen, and one of $R^4$ and $R^5$ is $C_{1-6}$ alkyl or hydrogen and the other is $(CH_2)_n$phenyl, $(CH_2)_n$pyridyl, $(CH_2)_n$pyrimidinyl, $(CH_2)_n$triazolyl, pyrazinyl, or $(CH_2)_n$oxadiazolyl, said phenyl, pyridyl, pyrimidinyl, triazolyl, pyrazinyl and oxadiazolyl optionally substituted with 1 to 3 groups of $R^a$. Still another subembodiment of this invention is realized when $R^2$ of $CR^2R^4R^5$ is hydrogen, and one of $R^4$ and $R^5$ is $C_{1-6}$ alkyl or hydrogen and the other is $(CH_2)_n$pyridyl, or $(CH_2)_n$oxadiazolyl, said oxadiazolyl optionally substituted with 1 to 3 groups of $R^a$.

Another embodiment of the present invention is realized when $R^3$ is $(CH_2)_nC_{6-10}$ aryl, optionally substituted with 1 to 3 groups of $R^a$. A subembodiment of this invention is realized when said aryl is optionally substituted phenyl.

Another embodiment of the present invention is realized when $R^3$ is $(CH_2)_nC_{5-10}$ heterocyclyl optionally substituted with 1 to 3 groups of $R^a$. A subembodiment of this invention is realized when said heterocyclyl is optionally substituted $(CH_2)_n$pyridyl, $(CH_2)_n$pyrimidinyl, $(CH_2)_n$triazolyl, $(CH_2)_n$oxadiazolyl, or pyrazinyl. Another subembodiment of this invention is realized when the heterocyclyl is optionally substituted $(CH_2)_n$pyridyl, or $(CH_2)_n$oxadiazolyl.

Still another embodiment of the present invention is realized when $R^a$ is $C_{1-6}$ alkyl, halogen (preferably chloro or fluoro), —O—, $OR^2$, CN, $CF_3$, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN Still another embodiment of this invention is realized by structural formula II:

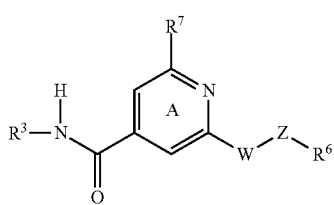

Wherein $R^3$, $R^6$, $R^7$, W and Z are as previously described. A subembodiment of formula II is realized when W and Z are absent, $R^7$ is $(CH_2)_nC_{6-10}$ aryl, or $(CH_2)_nC_{6-10}$ heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. Another subembodiment of formula II is realized when $R^7$ is phenyl, pyridinyl, morpholinyl, pyrimidinyl, imidazolyl, or oxazolyl optionally substituted with 1 to 3 groups of $R^a$.

Still another subembodiment of the compound of formula II is realized by structural formula IIa:

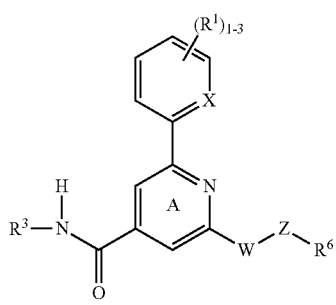

wherein $R^1$, $R^3$, $R^6$, X, W and Z are as previously described. A subembodiment of formula IIa is realized when W and Z are absent, $R^6$ is $C_{1-6}$ alkyl, optionally substituted with 1 to 3 groups of $R^a$, X is CH, $R^1$ is H, $C_{1-6}$ alkyl, halogen, or $(CH_2)_nCF_3$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$.

Yet another embodiment of this invention is realized by structural formula III:

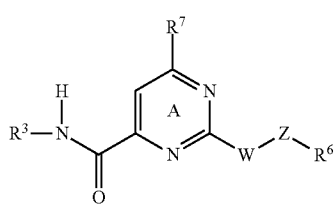

Wherein $R^3$, $R^6$, $R^7$, W and Z are as previously described. A subembodiment of formula III is realized when W and Z are absent, $R^7$ is $(CH_2)_nC_{6-10}$ aryl, or $(CH_2)_nC_{6-10}$ heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. Another subembodiment of formula III is realized when $R^7$ is phenyl, pyridinyl, morpholinyl, pyrimidinyl, imidazolyl, or oxazolyl optionally substituted with 1 to 3 groups of $R^a$.

Another embodiment of this invention is realized by structural formula IV:

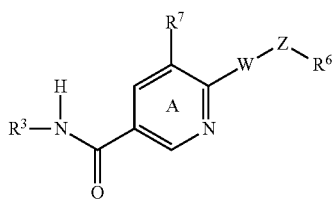

IV

Wherein $R^3$, $R^6$, $R^7$, W and Z are as previously described. A subembodiment of formula IV is realized when W and Z are absent, $R^7$ is $(CH_2)_nC_{6-10}$ aryl, or $(CH_2)_nC_{6-10}$ heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. Another subembodiment of formula IV is realized when $R^7$ is phenyl, pyridinyl, morpholinyl, pyrimidinyl, imidazolyl, or oxazolyl optionally substituted with 1 to 3 groups of $R^a$.

Another embodiment of this invention is realized by structural formula V:

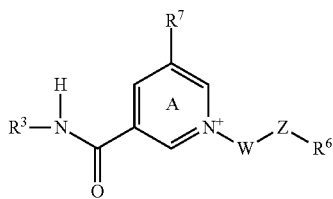

V wherein $R^3$, $R^6$, $R^7$, W and Z are as previously described and the "+" charge on the ring is balanced by a counter balancing ion group of W, Z or $R^6$. A subembodiment of formula V is realized when W and Z are absent, $R^7$ is $(CH_2)_nC_{6-10}$ aryl, or $(CH_2)_nC_{6-10}$ heterocyclyl optionally substituted with 1 to 3 groups of $R^a$, $R^6$ is —O—, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. A subembodiment of formula V is realized when $R^7$ is phenyl, pyridinyl, morpholinyl, pyrimidinyl, imidazolyl, or oxazolyl optionally substituted with 1 to 3 groups of $R^a$.

Another embodiment of this invention is realized by structural formula VI:

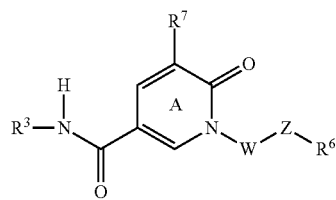

VI

Wherein $R^3$, $R^6$, $R^7$, W and Z are as previously described. A subembodiment of formula VI is realized when W and Z are absent, $R^7$ is $(CH_2)_nC_{6-10}$ aryl, or $(CH_2)_nC_{6-10}$ heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, any of which is optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_nC_{6-10}$ aryl, or $(CH_2)_nC_{6-10}$ heterocyclyl, said alkyl, aryl and heterocyclyl optionally substituted with 1 to 3 groups of $R^a$. A subembodiment of formula VI is realized when $R^7$ is phenyl, pyridinyl, morpholinyl, pyrimidinyl, imidazolyl, or oxazolyl any one of which is optionally substituted with 1 to 3 groups of $R^a$, $R^2$ of $CR^2R^4R^5$ in $R^3$ is hydrogen, and one of $R^4$ and $R^5$ of $CR^2R^4R^5$ is $C_{1-6}$ alkyl or hydrogen and the other is $(CH_2)_n$phenyl, $(CH_2)_n$pyridyl, $(CH_2)_n$pyrimidinyl, $(CH_2)_n$triazolyl, pyrazinyl, or $(CH_2)_n$oxadiazolyl, said phenyl, pyridyl, pyrimidinyl, triazolyl, pyrazinyl and oxadiazolyl optionally substituted with 1 to 3 groups of $R^a$. Another subembodiment of formula VI is realized when $R^2$ of $CR^2R^4R^5$ in $R^3$ is hydrogen, and one of $R^4$ and $R^5$ of $CR^2R^4R^5$ is $C_{1-6}$ alkyl or hydrogen and the other is $(CH_2)_n$oxadiazolyl, said oxadiazolyl optionally substituted with 1 to 3 groups of $R^a$.

TABLE 1

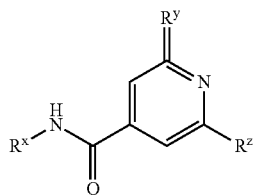

| Example | $R^x$ | $R^y$ | $R^z$ | MS (M + 1) |
|---|---|---|---|---|
| 1.1 | 4-F-phenyl-CH(CH₃)- | 2-CN-phenyl- | -CH₂-morpholinyl | 445.2029 |

TABLE 1-continued

| Example | R^x | R^y | R^z | MS (M + 1) |
|---------|-----|-----|-----|------------|
| 1.2 | 6-chloropyridin-3-yl ethyl | 2-cyanophenyl | morpholinomethyl | 448.1536 |
| 1.3 | 1-(4-fluorophenyl)ethyl | 3-fluoro-4-yl phenyl | 2-phenylmorpholin-4-yl | 514.2299 |
| 1.4 | 1-(4-fluorophenyl)ethyl | 3-fluoro-4-yl phenyl | 3,3-dimethylpiperidin-1-yl | 464.2513 |
| 1.5 | tert-butyl | 3-fluoro-4-yl phenyl | 5-(pyridin-2-yl)-4,5-dihydroisoxazol-3-yl | 419.1874 |
| 1.6 | 1-(pyrimidin-4-yl)ethyl | 3-fluoro-4-yl phenyl | 2-phenylmorpholin-4-yl | 498.2304 |
| 1.7 | 1-(6-(trifluoromethyl)pyridin-3-yl)ethyl | 3-fluoro-4-yl phenyl | 5-(pyridin-2-yl)-4,5-dihydroisoxazol-3-yl | 550.1855 |

TABLE 1-continued
| Example | R$^x$ | R$^y$ | R$^z$ | MS (M + 1) |
|---|---|---|---|---|
| 1.8 | 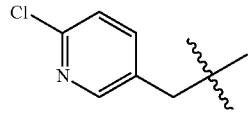 [SMILES: *Cc1ccc(Cl)nc1] | 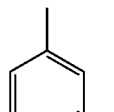 | 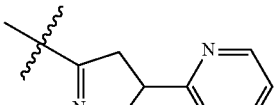 | 502.1454 |
| 1.9 | 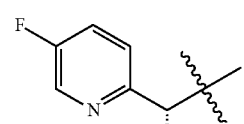 | 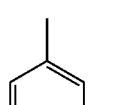 | 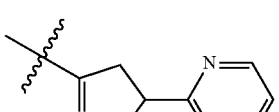 | 500.1887 |
| 1.10 | 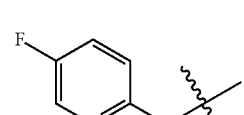 | 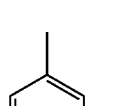 |  | 434.2247 |
| 1.11 | 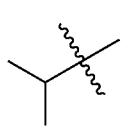 [SMILES: *C(C)C] | 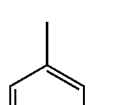 | 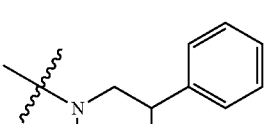 | 432.2455 |
| 1.12 | 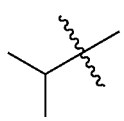 [SMILES: *C(C)C] | 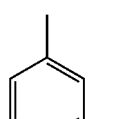 | 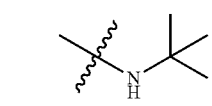 [SMILES: *NC(C)(C)C] | 344.2140 |
| 1.13 | 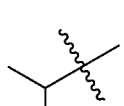 | 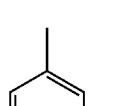 | 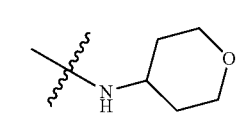 [SMILES: *NC1CCOCC1] | 372.2095 |

TABLE 1-continued
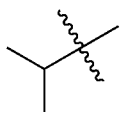 [SMILES: *C(C)C]
| Example | R<sup>x</sup> | R<sup>y</sup> | R<sup>z</sup> | MS (M + 1) |
|---|---|---|---|---|
| 1.14 | 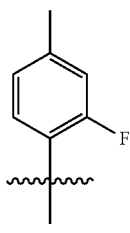 [SMILES: *c1ccc(C)cc1F] | 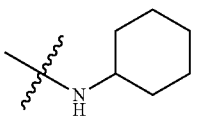 [SMILES: *NC1CCCCC1] | 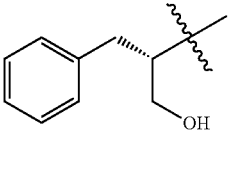 [SMILES: *[C@H](CO)Cc1ccccc1] | 370.2301 |
| 1.15 | 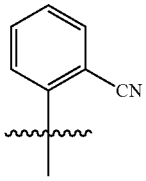 [SMILES: *c1ccccc1C#N] | 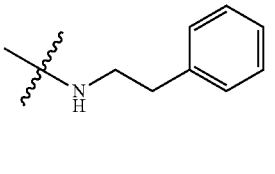 [SMILES: *NCCc1ccccc1] | 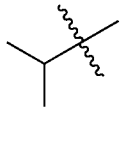 [SMILES: *C(C)C] | 477.2293 |
| 1.16 | 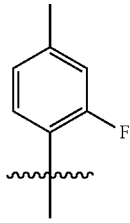 [SMILES: *c1ccc(C)cc1F] | 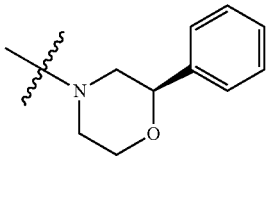 | 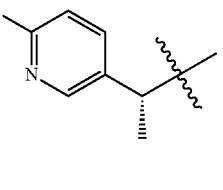 | 434.2252 |
| 1.17 | 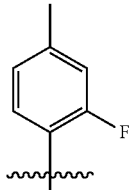 | 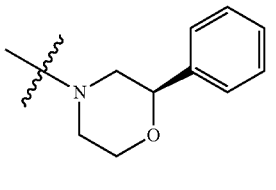 [SMILES: *N1CCO[C@H](c2ccccc2)C1] | 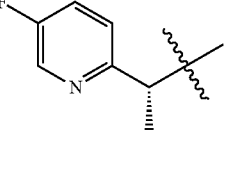 | 565.2232 |
| 1.18 | 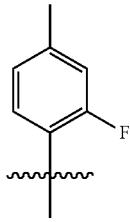 [SMILES: *c1ccc(C)cc1F] | 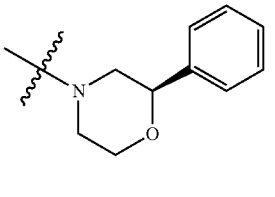 [SMILES: *N1CCO[C@H](c2ccccc2)C1] | 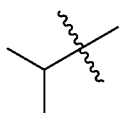 [SMILES: *C(C)C] | 515.2274 |
| 1.19 | 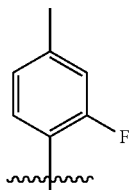 | 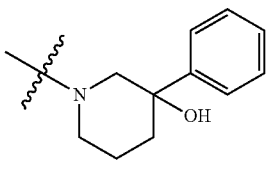 [SMILES: *N1CCCC(O)(c2ccccc2)C1] |  | 448.2396 |

TABLE 1-continued
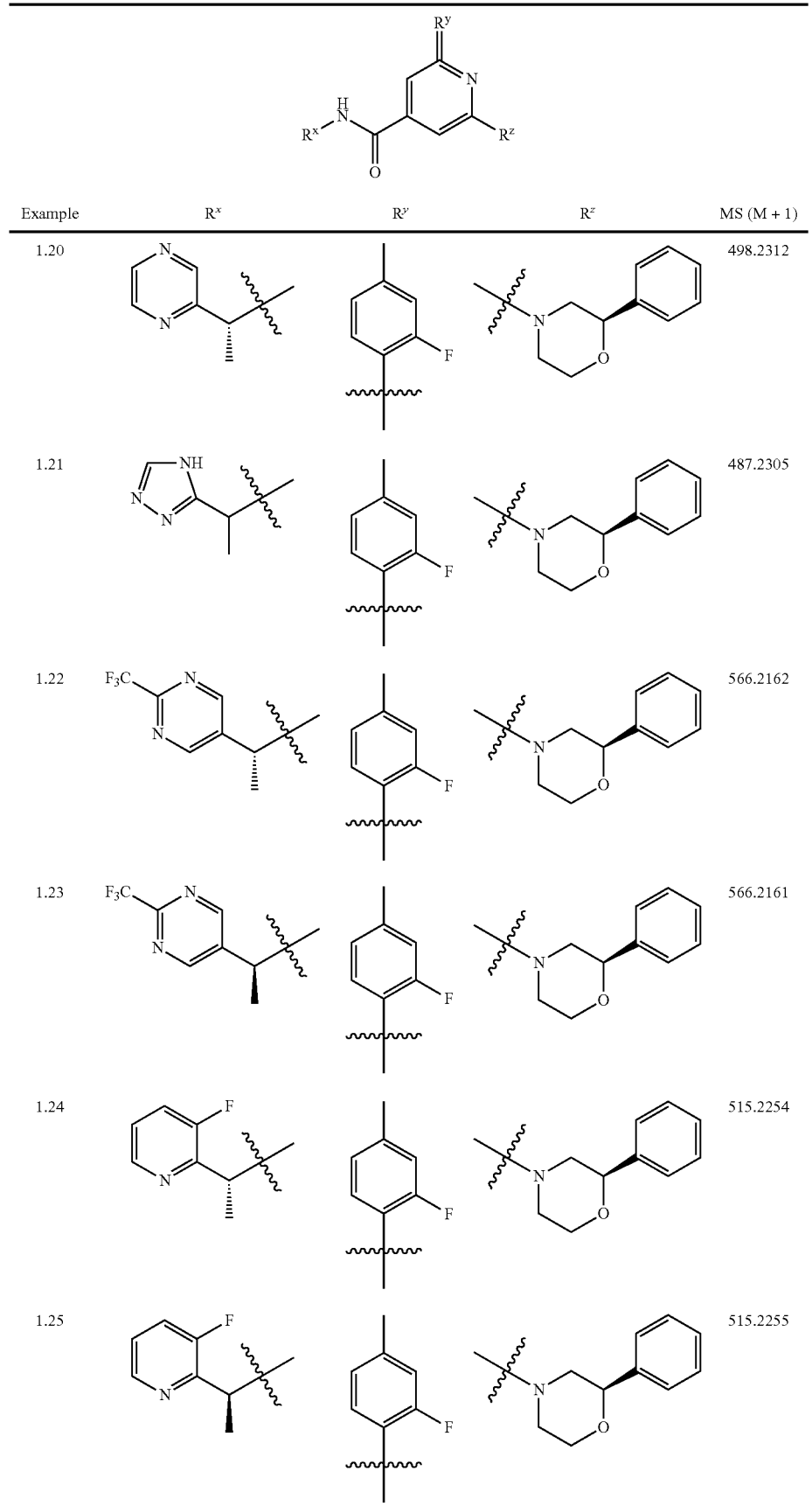
| Example | $R^x$ | $R^y$ | $R^z$ | MS (M + 1) |
|---|---|---|---|---|
| 1.20 | | | | 498.2312 |
| 1.21 | | | | 487.2305 |
| 1.22 | | | | 566.2162 |
| 1.23 | | | | 566.2161 |
| 1.24 | | | | 515.2254 |
| 1.25 | | | | 515.2255 |

TABLE 1-continued
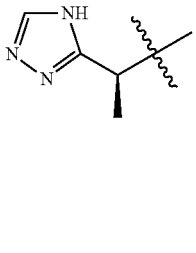 [SMILES: *[C@@H](C)c1nnc[nH]1]
| Example | R$^x$ | R$^y$ | R$^z$ | MS (M + 1) |
|---|---|---|---|---|
| 1.26 | 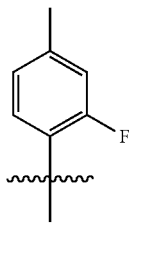 [SMILES: *c1ccc(C)cc1F] | 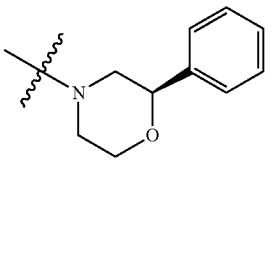 [SMILES: *N1CCO[C@H](c2ccccc2)C1] | 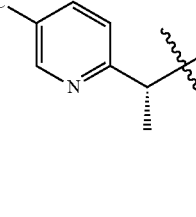 | 487.2272 |
| 1.27 | 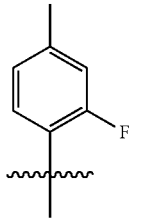 [SMILES: *c1ccc(C)cc1F] | 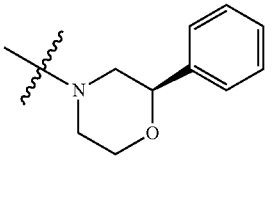 [SMILES: *N1CCO[C@H](c2ccccc2)C1] | 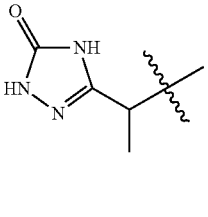 [SMILES: *C(C)c1n[nH]c(=O)[nH]1] | 565.2261 |
| 1.28 | 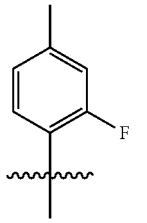 [SMILES: *c1ccc(C)cc1F] | 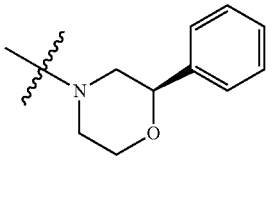 [SMILES: *N1CCO[C@H](c2ccccc2)C1] | 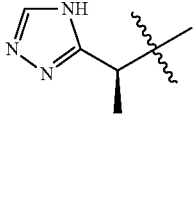 | 503.2214 |
| 1.29 | 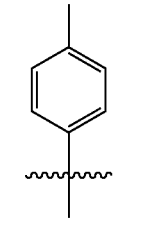 | 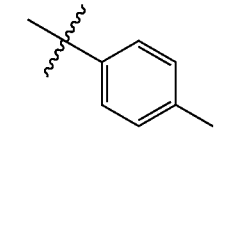 [SMILES: *c1ccc(C)cc1] | 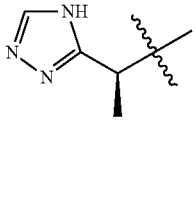 [SMILES: *[C@@H](C)c1nnc[nH]1] | 398.1987 |
| 1.30 | 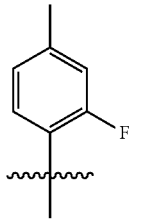 [SMILES: *c1ccc(C)cc1F] | 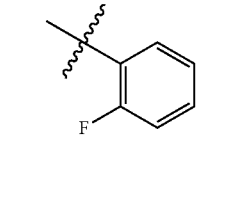 [SMILES: *c1ccccc1F] | | 406.1481 |

TABLE 1-continued

| Example | R^x | R^y | R^z | MS (M + 1) |
|---|---|---|---|---|
| 1.31 | 3-methyl-1,2,4-oxadiazol-5-yl-CH(CH₃)- | 2-fluorophenyl | morpholino | 426.1930 |
| 1.32 | 4H-1,2,4-triazol-3-yl-CH(CH₃)- | 2-fluorophenyl | morpholino | 411.1936 |
| 1.33 | 2-(trifluoromethyl)pyrimidin-5-yl-CH(CH₃)- | 2-fluorophenyl | morpholino | 490.1853 |
| 1.34 | 3-methyl-1,2,4-oxadiazol-5-yl-CH(CH₃)- | 2,4-difluorophenyl | 2,4-difluorophenyl | 457.1277 |
| 1.35 | 5-methyl-1,2,4-oxadiazol-3-yl-CH(CH₃)- | 2,4-difluorophenyl | 2,4-difluorophenyl | 457.1282 |
| 1.36 | 5-fluoropyridin-2-yl N-oxide-CH(CH₃)- | 2,4-difluorophenyl | 2,4-difluorophenyl | 486.1236 |

TABLE 1-continued

| Example | R^x | R^y | R^z | MS (M + 1) |
|---|---|---|---|---|
| 1.37 | (6-trifluoromethylpyridin-3-yl N-oxide, α-methyl) | 2,4-difluorophenyl | 2,4-difluorophenyl | 536.1206 |
| 1.38 | (3-methyl-1,2,4-oxadiazol-5-yl, α-methyl) | 4-methylphenyl | 4-methylphenyl | 413.1967 |
| 1.39 | (5-methyl-1,2,4-oxadiazol-3-yl, α-methyl) | 4-methylphenyl | 4-methylphenyl | 413.1964 |
| 1.40 | (5-fluoropyridin-2-yl N-oxide, α-methyl) | 4-methylphenyl | 4-methylphenyl | 442.1926 |
| 1.41 | (6-trifluoromethylpyridin-3-yl N-oxide, α-methyl) | 4-methylphenyl | 4-methylphenyl | 492.1886 |

TABLE 1-continued

| Example | R$^x$ | R$^y$ | R$^z$ | MS (M + 1) |
|---|---|---|---|---|
| 1.42 | 6-(trifluoromethyl)pyridin-3-yl N-oxide with (S)-methyl linker | 2,4-difluorophenyl | C(CH$_3$)$_2$OH | 440.1052 |
| 1.43 | 6-(trifluoromethyl)pyridin-3-yl N-oxide with (S)-methyl linker | 2,4-difluorophenyl | H | 424.1084 |
| 1.44 | 3-methyl-1,2,4-oxadiazol-5-yl with (S)-methyl linker | 2,4-difluorophenyl | H | 345.1158 |
| 1.45 | 5-methyl-1,2,4-oxadiazol-3-yl with (S)-methyl linker | 2,4-difluorophenyl | H | 345.1159 |
| 1.46 | 5-fluoropyridin-2-yl N-oxide with (S)-methyl linker | 2,4-difluorophenyl | H | 374.1110 |

TABLE 1-continued

| Example | R^x | R^y | R^z | MS (M + 1) |
|---------|-----|-----|-----|------------|
| 1.47 | 4H-1,2,4-triazol-3-yl-CH(CH₃)- | 2,4-difluorophenyl | 2,4-difluorophenyl | 442.1293 |
| 1.48 | 3-methyl-1,2,4-oxadiazol-5-yl-CH(CH₃)- | 4-methylphenyl | -C(CH₃)₂OH | 381.1921 |
| 1.49 | 4H-1,2,4-triazol-3-yl-CH(CH₃)- | 2,4-difluorophenyl | -C(CH₃)₂OH | 388.1590 |
| 1.50 | 2-(trifluoromethyl)pyridine N-oxide-5-yl-CH(CH₃)- | 2,4-difluorophenyl | -CH(CH₃)₂ (isopropyl with extra methyl) | 466.1542 |
| 1.51 | 3-methyl-1,2,4-oxadiazol-5-yl-CH(CH₃)- | 2,4-difluorophenyl | -CH(CH₃)CH(CH₃)₂ | 387.1620 |

TABLE 1-continued

| Example | Rˣ | Rʸ | Rᶻ | MS (M + 1) |
|---------|----|----|----|------------|
| 1.52 | 5-methyl-1,2,4-oxadiazol-3-yl with (S)-methyl linker | 2,4-difluorophenyl | isopropyl | 387.1620 |
| 1.53 | 4H-1,2,4-triazol-3-yl with (S)-methyl linker | 2,4-difluorophenyl | isopropyl | 372.1624 |
| 1.54 | 5-(trifluoromethyl)pyridin-2-yl N-oxide with (S)-methyl linker | 2,4-difluorophenyl | isopropyl | 416.1575 |
| 1.55 | 3-methyl-1,2,4-oxadiazol-5-yl with (S)-methyl linker | 2,4-difluorophenyl | methoxymethyl | 375.1255 |
| 1.56 | 5-methyl-1,2,4-oxadiazol-3-yl with (S)-methyl linker | 2,4-difluorophenyl | methoxymethyl | 375.1256 |

TABLE 1-continued
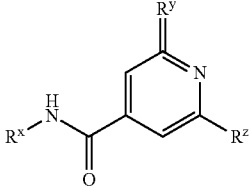
| Example | R$^x$ | R$^y$ | R$^z$ | MS (M + 1) |
|---|---|---|---|---|
| 1.57 | 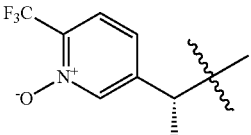 | 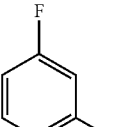 | 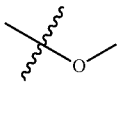 | 454.1183 |
| 1.58 | 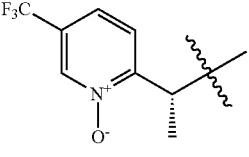 | 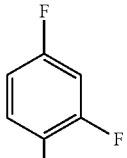 | 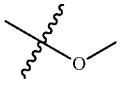 | 404.1213 |
| 1.59 | 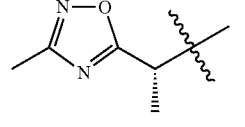 | 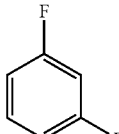 | 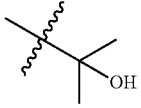 | 403.1563 |
| 1.60 | 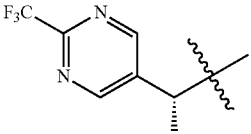 | 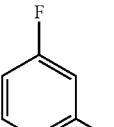 |  | 467.1474 |
| 1.61 | 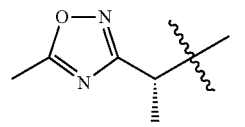 [SMILES: *[C@H](C)c1noc(C)n1] | 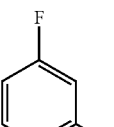 | 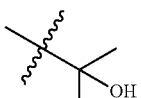 | 403.1560 |

TABLE 1-continued
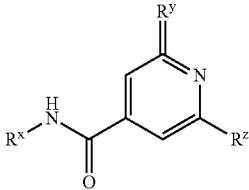
| Example | R$^x$ | R$^y$ | R$^z$ | MS (M + 1) |
|---|---|---|---|---|
| 1.62 | 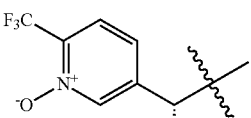 | 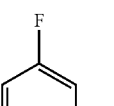 | 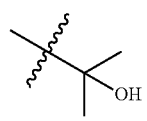 [SMILES: *C(C)(C)O] | 482.1461 |
| 1.63 | 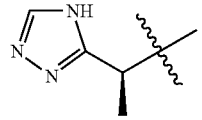 [SMILES: *[C@@H](C)c1nnc[nH]1] | 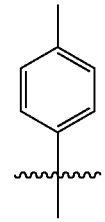 | 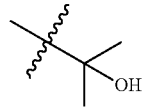 [SMILES: *C(C)(C)O] | 366.1926 |
| 1.64 | 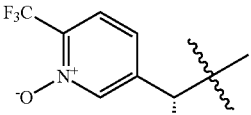 | 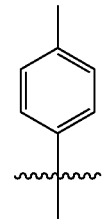 | 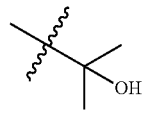 | 460.1843 |
| 1.65 | 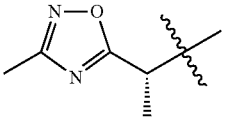 | 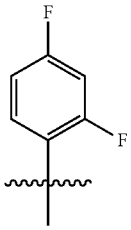 [SMILES: *c1ccc(F)cc1F] | 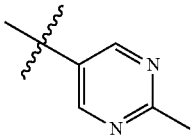 [SMILES: *c1cnc(C)nc1] | 437.1535 |
| 1.66 | 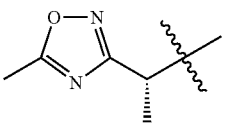 [SMILES: *[C@H](C)c1noc(C)n1] | 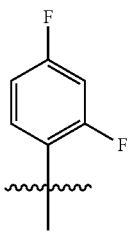 [SMILES: *c1ccc(F)cc1F] | 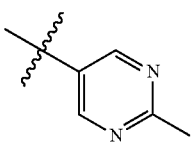 [SMILES: *c1cnc(C)nc1] | 437.1535 |

TABLE 1-continued
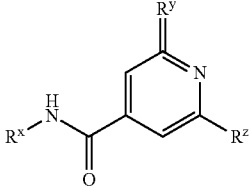
| Example | R<sup>x</sup> | R<sup>y</sup> | R<sup>z</sup> | MS (M + 1) |
|---|---|---|---|---|
| 1.67 | 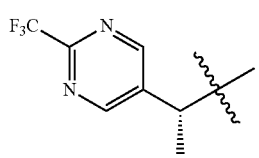 [SMILES: *[C@H](C)c1cnc(C(F)(F)F)nc1] | 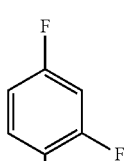 | 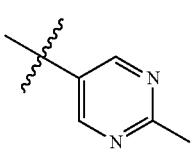 [SMILES: *c1cnc(C)nc1] | 501.1459 |
| 1.68 | 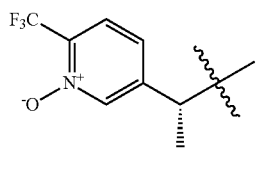 | 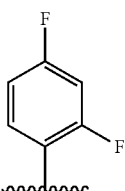 | 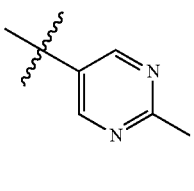 [SMILES: *c1cnc(C)nc1] | 516.1455 |
| 1.69 | 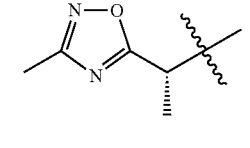 [SMILES: *[C@H](C)c1nc(C)no1] | 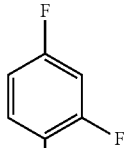 | 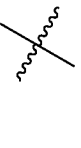 | 359.1324 |
| 1.70 | 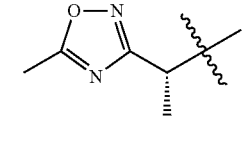 [SMILES: *[C@H](C)c1noc(C)n1] | 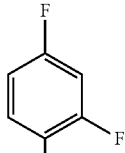 |  | 359.1322 |
| 1.71 | 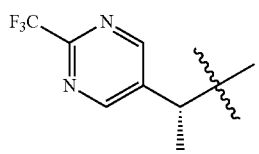 [SMILES: *[C@H](C)c1cnc(C(F)(F)F)nc1] | 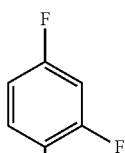 | 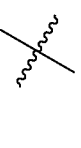 | 423.1246 |

TABLE 1-continued
| Example | R$^x$ | R$^y$ | R$^z$ | MS (M + 1) |
|---|---|---|---|---|
| 1.72 | 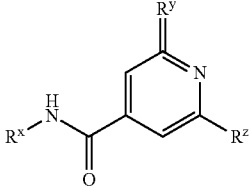 | 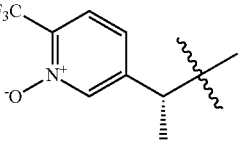 | 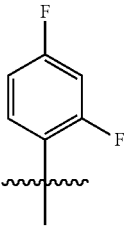 [SMILES: *c1ccc(F)cc1F] | 438.1245 |
| 1.73 |  | 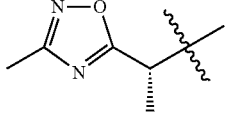 [SMILES: *[C@H](C)c1nc(C)no1] | 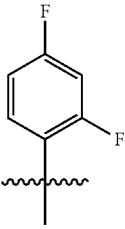 [SMILES: *c1ccc(F)cc1F] | 385.1468 |
| 1.74 |  | 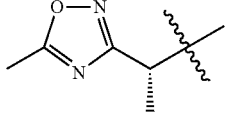 [SMILES: *[C@H](C)c1noc(C)n1] | 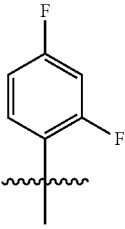 [SMILES: *c1ccc(F)cc1F] | 385.1470 |
| 1.75 |  | 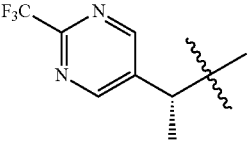 [SMILES: *[C@H](C)c1cnc(C(F)(F)F)nc1] | 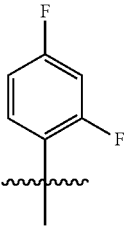 [SMILES: *c1ccc(F)cc1F] | 449.1392 |
| 1.76 |  | 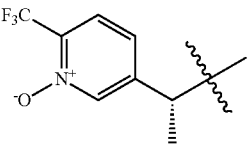 | 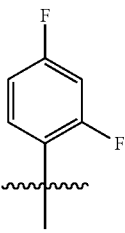 [SMILES: *c1ccc(F)cc1F] | 464.1390 |

TABLE 1-continued
| Example | R$^x$ | R$^y$ | R$^z$ | MS (M + 1) |
|---|---|---|---|---|
| 1.77 | 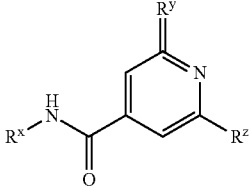 | 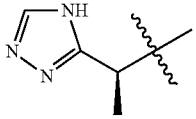 [SMILES: *[C@@H](C)c1nnc[nH]1] | 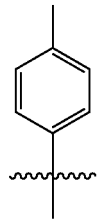 | 338.1618 |
| 1.78 | 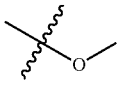 | 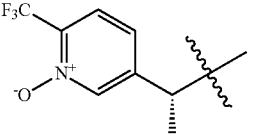 | 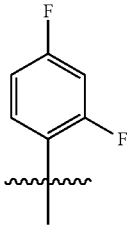 [SMILES: *c1ccc(F)cc1F] | 522.1063 |
| 1.79 | 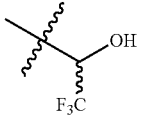 | 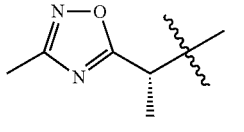 [SMILES: *[C@H](C)c1nc(C)no1] | 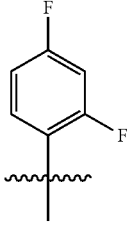 [SMILES: *c1ccc(F)cc1F] | 443.1144 |
| 1.80 | 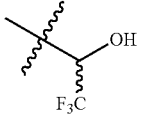 | 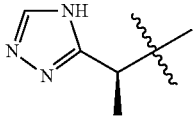 | 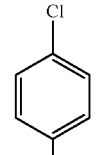 | 386.1381 |
| 1.81 | 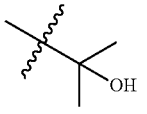 [SMILES: *C(C)(C)O] | 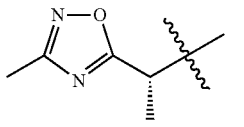 | 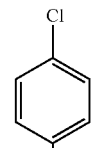 | 401.1370 |

TABLE 1-continued
| Example | R$^x$ | R$^y$ | R$^z$ | MS (M + 1) |
|---|---|---|---|---|
| 1.82 | 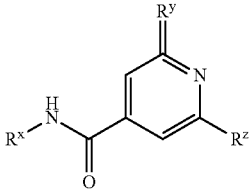 | 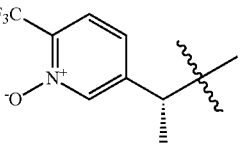 | 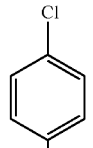 | 480.1292 |
| 1.83 | 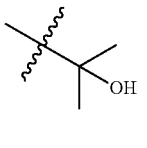 [SMILES: *C(C)(C)O] | 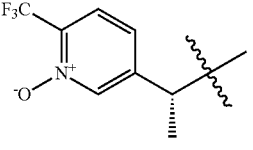 | 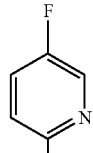 | 505.1112 |
| 1.84 | 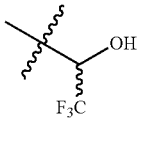 | 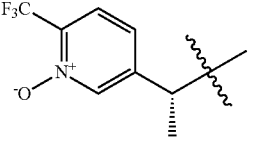 | 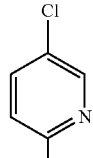 | 481.1253 |
| 1.85 | 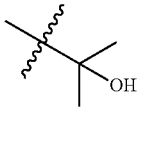 | 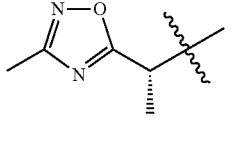 | 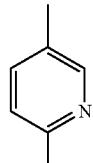 | 366.1927 |
| 1.86 | 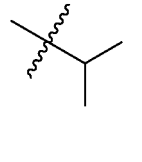 [SMILES: *C(C)C] | 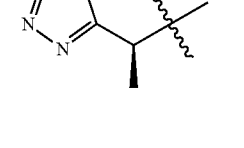 | 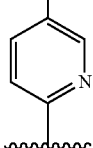 | 351.1928 |
| 1.87 | 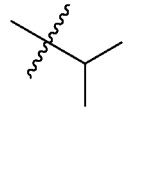 [SMILES: *C(C)C] | 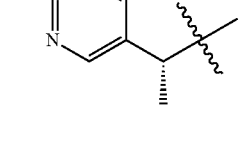 | 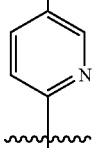 | 430.1850 |

TABLE 1-continued

| Example | R$^x$ | R$^y$ | R$^z$ | MS (M + 1) |
|---------|-------|-------|-------|------------|
| 1.88 | (S)-1-(2-(trifluoromethyl)pyridin-5-yl N-oxide)ethyl | 5-methylpyridin-2-yl | tert-butyl | 445.1846 |
| 1.89 | (S)-1-(4H-1,2,4-triazol-3-yl)ethyl | 5-methylpyridin-2-yl | 2-hydroxy-2-methylpropyl | 367.1869 |
| 1.90 | (S)-1-(2-(trifluoromethyl)pyrimidin-5-yl)ethyl | 5-methylpyridin-2-yl | 2-hydroxy-2-methylpropyl | 446.1786 |
| 1.91 | (S)-1-(2-(trifluoromethyl)pyridin-5-yl N-oxide)ethyl | 5-methylpyridin-2-yl | 2-hydroxy-2-methylpropyl | 461.1783 |
| 1.92 | (S)-1-(3-methyl-1,2,4-oxadiazol-5-yl)ethyl | 5-methylpyridin-2-yl | 2-hydroxy-2-methylpropyl | 382.1865 |

TABLE 1-continued
| Example | R$^x$ | R$^y$ | R$^z$ | MS (M + 1) |
|---|---|---|---|---|
| 1.93 | 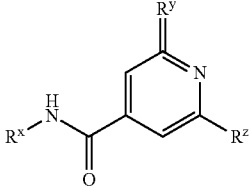 | 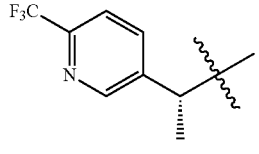 [SMILES: *[C@H](C)c1ccc(C(F)(F)F)nc1] | 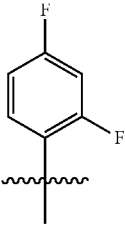 [SMILES: *c1ccc(F)cc1F] | 466.1543 |
| 1.94 | 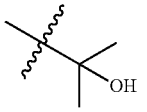 | 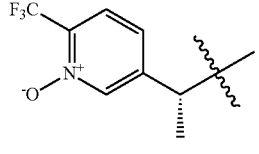 | 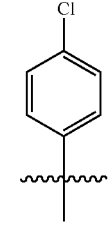 | 520.0869 |
| 1.95 | 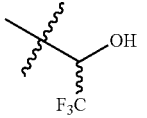 | 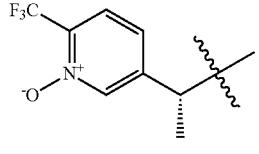 | 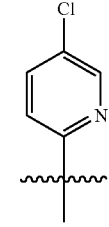 | 521.0830 |
| 1.96 | 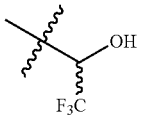 | 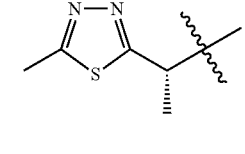 [SMILES: *[C@H](C)c1nnc(C)s1] | 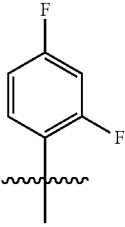 [SMILES: *c1ccc(F)cc1F] | 419.1350 |
| 1.97 | 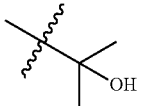 [SMILES: *C(C)(C)O] | 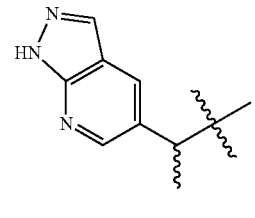 [SMILES: *C(C)c1cnc2[nH]ncc2c1] | 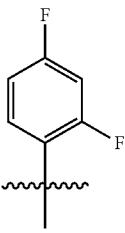 [SMILES: *c1ccc(F)cc1F] | 438.1744 |

TABLE 1-continued
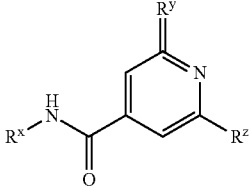
| Example | R$^x$ | R$^y$ | R$^z$ | MS (M + 1) |
|---|---|---|---|---|
| 1.98 | 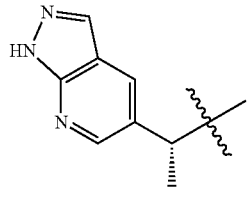 [SMILES: *[C@H](C)c1cnc2[nH]ncc2c1] | 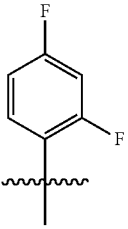 [SMILES: *c1ccc(F)cc1F] | 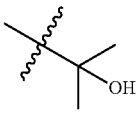 | 438.1745 |
| 1.99 | 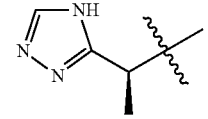 [SMILES: *[C@@H](C)c1nnc[nH]1] | 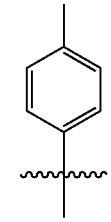 | 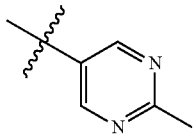 [SMILES: *c1cnc(C)nc1] | 400.1879 |
| 1.100 | 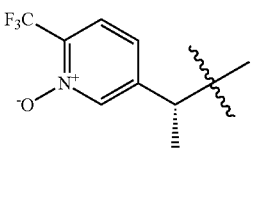 | 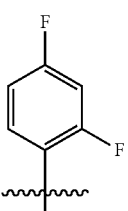 | 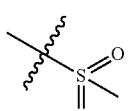 | 502.0856 |
| 1.101 | 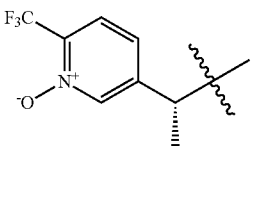 | 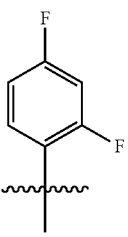 [SMILES: *c1ccc(F)cc1F] | 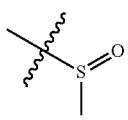 | 486.0905 |
| 1.102 | 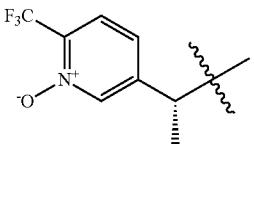 | 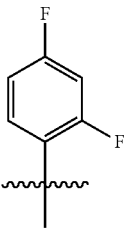 | 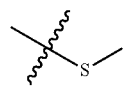 | 470.0950 |

TABLE 1-continued

| Example | R$^x$ | R$^y$ | R$^z$ | MS (M + 1) |
| --- | --- | --- | --- | --- |
| 1.103 | 5-methyl-1,2,4-oxadiazol-3-yl-CH(CH$_3$)- | 2,4-difluorophenyl | methylsulfonyl | 423.0932 |
| 1.104 | 3-methyl-1,2,4-oxadiazol-5-yl-CH(CH$_3$)- | 2,4-difluorophenyl | methylsulfonyl | 423.0933 |
| 1.105 | 5-methyl-1,2,4-thiadiazol-3-yl-C(CH$_3$)$_2$- | 2,4-difluorophenyl | 2-hydroxyprop-2-yl | 419.1354 |
| 1.106 | 5-methyl-1,3,4-thiadiazol-2-yl-CH(CH$_3$)- | 2,4-difluorophenyl | 2-hydroxyprop-2-yl | 413.1341 |
| 1.107 | 4H-1,2,4-triazol-3-yl-CH(CH$_3$)- | 4-chlorophenyl | methylsulfonyl | 406.0752 |

TABLE 1-continued

| Example | R$^x$ | R$^y$ | R$^z$ | MS (M + 1) |
|---|---|---|---|---|
| 1.108 | 5-methyl-1,3,4-thiadiazol-2-yl-CH(CH₃)- | Cl | -S(O)₂CH₃ | 437.0529 |
| 1.109 | 6-(trifluoromethyl)pyridin-3-yl-CH(CH₃)- | Cl | -S(O)₂CH₃ | 484.0704 |
| 1.110 | 6-(trifluoromethyl)pyridin-3-yl N-oxide-CH(CH₃)- | Cl | -S(O)₂CH₃ | 500.0667 |
| 1.111 | 5-methyl-1,3,4-thiadiazol-2-yl-CH(CH₃)- | Cl | -S(O)₂CH₃ | 437.0528 |
| 1.112 | 5-methyl-1,2,4-oxadiazol-3-yl-CH(CH₃)- | Cl | -S(O)₂CH₃ | 421.0758 |

TABLE 1-continued
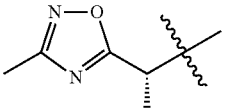
| Example | R$^x$ | R$^y$ | R$^z$ | MS (M + 1) |
|---|---|---|---|---|
| 1.113 | 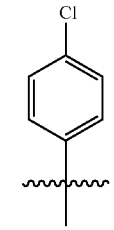 | 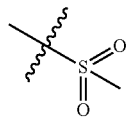 [SMILES: *S(C)(=O)=O] | 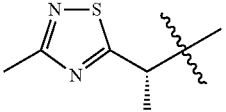 | 421.0739 |
| 1.114 | 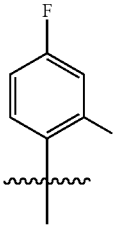 | 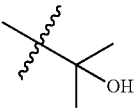 [SMILES: *C(C)(C)O] | 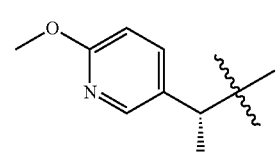 | 419.1346 |
| 1.115 | 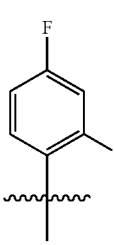 | 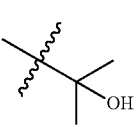 | 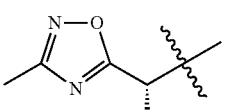 | 444.1728 |
| 1.116 | 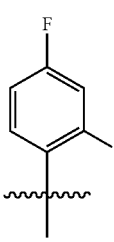 | 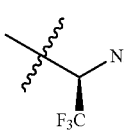 | 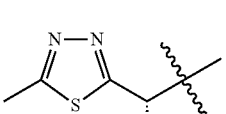 | 442.1298 |
| 1.117 | 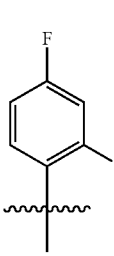 | 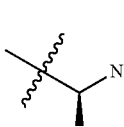 | | 458.1065 |

TABLE 1-continued

| Example | R$^x$ | R$^y$ | R$^z$ | MS (M + 1) |
|---|---|---|---|---|
| 1.118 | 3-methyl-1,2,4-thiadiazol-5-yl, CH(CH₃) | 4-chlorophenyl | methylsulfonyl (SO₂CH₃) | 437.2 |
| 1.119 | 3-methyl-1,2,4-oxadiazol-5-yl, C(CH₂OH) | 2,4-difluorophenyl | C(CH₃)₂OH | 419.1525 |
| 1.120 | 5-methyl-1,3,4-thiadiazol-2-yl, CH(CH₃) | 2,4-difluorophenyl | C(CH₃)(CF₃)NH₂ | 458.1067 |
| 1.121 | 3-methyl-1,2,4-oxadiazol-5-yl, CH(CH₃) | 2,4-difluorophenyl | C(CH₃)(CF₃)NH₂ | 442.1295 |
| 1.122 | 3-methyl-1,2,4-oxadiazol-5-yl, CH(CH₃) | 2,4-difluorophenyl | 5-methyl-1,3,4-thiadiazol-2-yl | 443.1102 |

TABLE 1-continued

| Example | R^x | R^y | R^z | MS (M + 1) |
|---------|-----|-----|-----|------------|
| 1.123 | 5-methyl-1,2,4-oxadiazol-3-yl with chiral methyl | 2,4-difluorophenyl | 5-methyl-1,3,4-thiadiazol-2-yl | 443.1096 |
| 1.124 | 5-methyl-1,3,4-thiadiazol-2-yl with chiral methyl | 2,4-difluorophenyl | 5-methyl-1,3,4-thiadiazol-2-yl | 459.0871 |
| 1.125 | 2-(trifluoromethyl)pyrimidin-5-yl with chiral methyl | 2,4-difluorophenyl | 5-methyl-1,3,4-thiadiazol-2-yl | 507.1026 |
| 1.126 | 6-(trifluoromethyl)pyridin-3-yl N-oxide with chiral methyl | 2,4-difluorophenyl | 5-methyl-1,3,4-thiadiazol-2-yl | 522.1016 |
| 1.127 | 4H-1,2,4-triazol-3-yl with chiral methyl | 2,4-difluorophenyl | 5-methyl-1,3,4-thiadiazol-2-yl | 428.1096 |

TABLE 1-continued

| Example | R$^x$ | R$^y$ | R$^z$ | MS (M + 1) |
|---|---|---|---|---|
| 1.128 | 6-(trifluoromethyl)pyridin-3-yl with CH(CH₂OH)- substituent | 2,4-difluorophenyl | -C(CH₃)₂OH | 482.1498 |
| 1.129 | 3-methyl-1,2,4-thiadiazol-5-yl with CH(CH₃)- substituent | 2,4-difluorophenyl | 5-methyl-1,3,4-thiadiazol-2-yl | 459.0862 |
| 1.130 | 6-(trifluoromethyl)pyridin-3-yl with CH(CH₂OH)- substituent | 2,4-difluorophenyl | -C(CH₃)₂OH | 482.1494 |
| 1.131 | 3-methyl-1,2,4-oxadiazol-5-yl with CH(CH₃)- substituent | 4-chlorophenyl | -S(O)₂Et | 435.0886 |
| 1.132 | 5-(trifluoromethyl)pyridin-2-yl with CH(CH₂OH)- substituent | 2,4-difluorophenyl | -C(CH₃)₂OH | 432.1522 |

TABLE 1-continued

| Example | R$^x$ | R$^y$ | R$^z$ | MS (M + 1) |
|---|---|---|---|---|
| 1.133 | 3-methyl-1,2,4-oxadiazol-5-yl with CH(CH₃) linker | 4-Cl-phenyl | -S(O)₂-iPr | 449.3 |
| 1.134 | 3-methyl-1,2,4-thiadiazol-5-yl with CH(CH₃) linker | 2,4-diF-phenyl | -C(CF₃)(NH₂)- | 458.1060 |
| 1.135 | 3-methyl-1,2,4-oxadiazol-5-yl with CH(CH₃) linker | 4-Cl-phenyl | -S(O)₂-CH₂CF₃ | 489.2 |
| 1.136 | 3-methyl-1,2,4-oxadiazol-5-yl with CH(CH₃) linker | 4-Cl-phenyl | -S(O)₂-cyclopentyl | 475.3 |
| 1.137 | 4H-1,2,4-triazol-3-yl with CH(CH₃) linker | 2,4-diF-phenyl | 1-(2,2,2-trifluoroethyl)-1,2,3-triazol-5-yl | 479.1353 |

TABLE 1-continued

| Example | Rˣ | Rʸ | Rᶻ | MS (M + 1) |
|---|---|---|---|---|
| 1.138 | 3-methyl-1,2,4-oxadiazol-5-yl with CH(CH₃) linker | 2,4-difluorophenyl | 1-(2,2,2-trifluoroethyl)-1,2,3-triazol-5-yl | 494.1358 |
| 1.139 | 3-methyl-1,2,4-thiadiazol-5-yl with CH(CH₃) linker | 2,4-difluorophenyl | 1-(2,2,2-trifluoroethyl)-1,2,3-triazol-5-yl | 510.1137 |
| 1.140 | 5-methyl-1,2,4-oxadiazol-3-yl with CH(CH₃) linker | 2,4-difluorophenyl | 1-(2,2,2-trifluoroethyl)-1,2,3-triazol-5-yl | 494.1358 |
| 1.141 | 3-methyl-1,2,4-oxadiazol-5-yl with CH(CH₃) linker | 2,4-difluorophenyl | 1-methyl-1,2,3-triazol-5-yl | 426.1475 |
| 1.142 | 4H-1,2,4-triazol-3-yl with CH(CH₂OH) linker | 4-methylphenyl | C(CH₃)₂OH | 382.1874 |

TABLE 1-continued

| Example | $R^x$ | $R^y$ | $R^z$ | MS (M + 1) |
|---|---|---|---|---|
| 1.143 | (morpholinomethyl-substituted isopropyl) | 4-methylphenyl | 2-hydroxyprop-2-yl | 398.2434 |
| 1.144 | (methoxymethyl-substituted isopropyl) | 4-methylphenyl | 2-hydroxyprop-2-yl | 343.2014 |
| 1.145 | (hydroxymethyl-substituted isopropyl) | 4-methylphenyl | 2-hydroxyprop-2-yl | 329.1858 |

TABLE 2

| Example | $R^x$ | $R^y$ | $R^z$ | MS (M + 1) |
|---|---|---|---|---|
| 2.1 | (4H-1,2,4-triazol-3-yl)ethyl | 4-methylphenyl | 4-methylphenyl | 399.1923 |

TABLE 2-continued
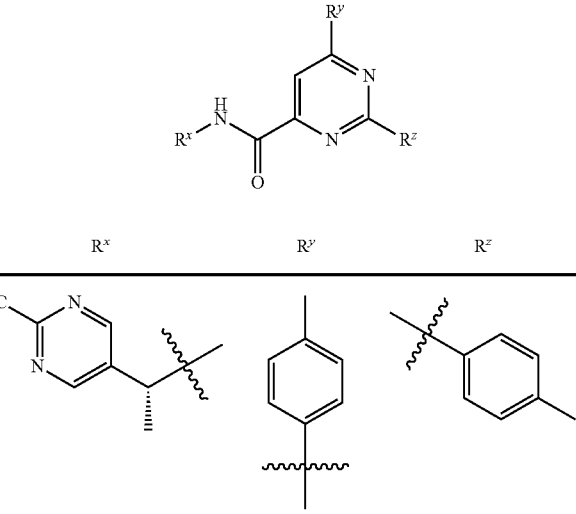
| Example | R$^x$ | R$^y$ | R$^z$ | MS (M + 1) |
|---|---|---|---|---|
| 2.2 | 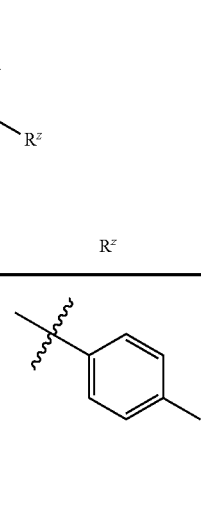 | 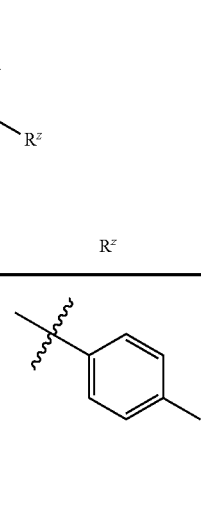 | 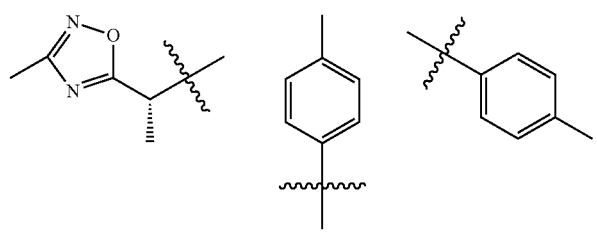 | 478.1847 |
| 2.3 | 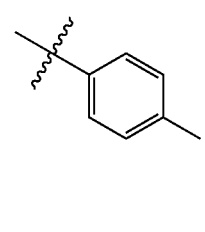 [SMILES: *c1ccc(C)cc1] | 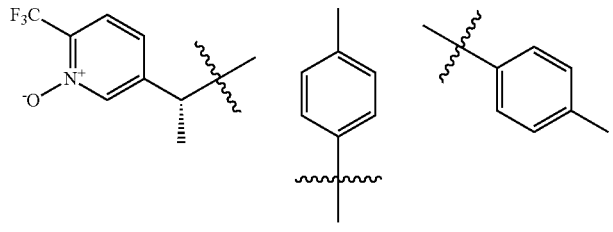 | 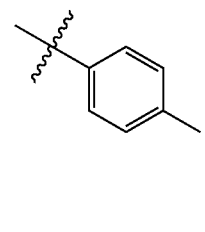 | 414.1924 |
| 2.4 | 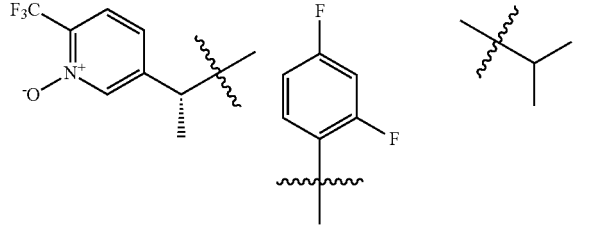 | 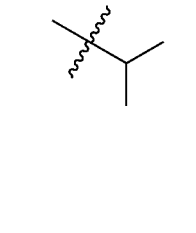 | 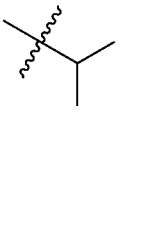 | 493.1847 |
| 2.5 | 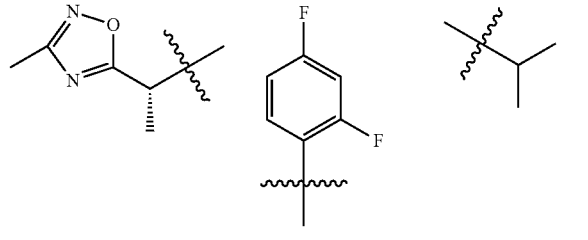 | 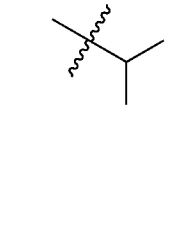 [SMILES: *C(C)C] | 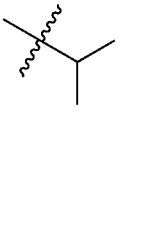 [SMILES: *C(C)C] | 467.1510 |
| 2.6 |  |  |  | 388.1579 |

TABLE 2-continued

| Example | R$^x$ | R$^y$ | R$^z$ | MS (M + 1) |
|---------|-------|-------|-------|------------|
| 2.7 | 2-(trifluoromethyl)pyrimidin-5-yl with chiral methyl linker | 2,4-difluorophenyl | tert-butyl | 452.1505 |
| 2.8 | 6-(trifluoromethyl)pyridin-3-yl N-oxide with chiral methyl linker | 4-methylphenyl | isopropyl | 445.1849 |
| 2.9 | 3-methyl-1,2,4-oxadiazol-5-yl with chiral methyl linker | 4-methylphenyl | isopropyl | 366.1924 |
| 2.10 | 2-(trifluoromethyl)pyrimidin-5-yl with chiral methyl linker | 4-methylpyridinyl | isopropyl | 430.1850 |
| 2.11 | 6-(trifluoromethyl)pyridin-3-yl N-oxide with chiral methyl linker | 2,4-difluorophenyl | 2-hydroxy-2-methylpropyl | 483.1454 |

TABLE 2-continued
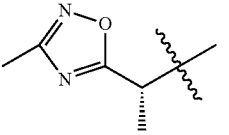 [SMILES: *[C@H](C)c1nc(C)no1]
| Example | R$^x$ | R$^y$ | R$^z$ | MS (M + 1) |
|---|---|---|---|---|
| 2.12 | 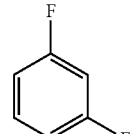 | 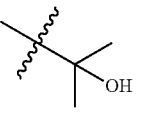 [SMILES: *C(C)(C)O] | 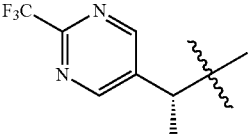 | 404.1533 |
| 2.13 | 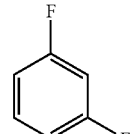 | 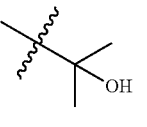 | 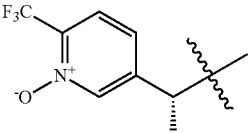 | 468.1455 |
| 2.14 | 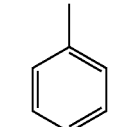 | 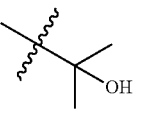 [SMILES: *C(C)(C)O] | 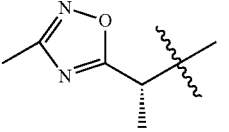 [SMILES: *[C@H](C)c1nc(C)no1] | 461.1803 |
| 2.15 | 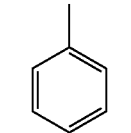 | 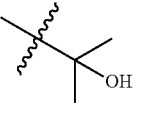 | 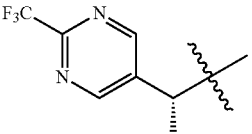 | 382.1874 |
| 2.16 | 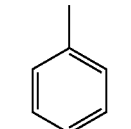 | 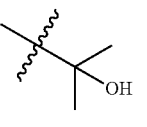 [SMILES: *C(C)(C)O] | | 446.1799 |

TABLE 3

| Example | R^x | R^y | R^z | MS (M + 1) |
|---|---|---|---|---|
| 3.1 | isopropyl-methyl | 3-fluoro-4-yl phenyl | H | 273.1 |
| 3.2 | pyrimidin-4-yl isopropyl | 3-fluoro-4-yl phenyl | H | 337.1646 |
| 3.3 | (4H-1,2,4-triazol-3-yl)isopropyl | 3-fluoro-4-yl phenyl | H | 326.1407 |
| 3.4 | (3-methyl-1,2,4-oxadiazol-5-yl)(S)-1-methyl | 4-yl phenyl | pyridin-2-yloxy (5-methyl) | 430.1881 |
| 3.5 | (4H-1,2,4-triazol-3-yl)(S)-1-methyl | 4-yl phenyl | pyridin-2-yloxy (5-methyl) | 415.1888 |

TABLE 3-continued

| Example | Rx | Ry | Rz | MS (M + 1) |
|---|---|---|---|---|
| 3.6 | 2-trifluoromethylpyrimidin-5-yl CH(CH3)- | 4-phenyl | 5-methylpyridin-2-yloxy CH(CH3)- | 494.1821 |
| 3.7 | 3-methyl-1,2,4-oxadiazol-5-yl CH(CH3)- | 3-fluoro-4-phenyl | H | 341.1408 |
| 3.8 | 2-trifluoromethylpyridin-5-yl N-oxide CH(CH3)- | 3-fluoro-4-phenyl | H | 420.1337 |
| 3.9 | 5-fluoropyridin-2-yl N-oxide CH(CH3)- | 3-fluoro-4-phenyl | H | 370.1359 |
| 3.10 | 5-methyl-1,2,4-oxadiazol-3-yl CH(CH3)- | 3-fluoro-4-phenyl | H | 341.1416 |
| 3.11 | 3-methyl-1,2,4-oxadiazol-5-yl CH(CH3)- | 2,3-difluoro-4-phenyl | H | 345.1157 |

TABLE 3-continued

| Example | R^x | R^y | R^z | MS (M + 1) |
|---|---|---|---|---|
| 3.12 | 5-methyl-1,2,4-oxadiazol-3-yl CH(CH3) | 2,4-difluorophenyl | H | 345.1156 |
| 3.13 | 6-(trifluoromethyl)pyridin-3-yl N-oxide CH(CH3) | 2,4-difluorophenyl | H | 424.1086 |
| 3.14 | 5-fluoropyridin-2-yl N-oxide CH(CH3) | 2,4-difluorophenyl | H | 374.1114 |
| 3.15 | 6-(trifluoromethyl)pyridin-3-yl N-oxide CH(CH3) | 4-fluorophenyl | H | 406.1177 |
| 3.16 | 3-methyl-1,2,4-oxadiazol-5-yl CH(CH3) | pyridin-2-yl | H | 324.1455 |

TABLE 3-continued

| Example | R^x | R^y | R^z | MS (M + 1) |
|---|---|---|---|---|
| 3.17 | 2-(trifluoromethyl)pyrimidin-5-yl, (S)-1-yl | pyridin-5-yl | H | 388.1386 |
| 3.18 | 3-methyl-1,2,4-oxadiazol-5-yl, (S)-1-yl | F, pyridin-5-yl | H | 328.1202 |
| 3.19 | 2-(trifluoromethyl)pyrimidin-5-yl, (S)-1-yl | F, pyridin-5-yl | H | 392.1128 |
| 3.20 | 6-(trifluoromethyl)pyridin-3-yl N-oxide, (S)-1-yl | pyridin-5-yl | H | 403.1380 |
| 3.21 | 6-(trifluoromethyl)pyridin-3-yl N-oxide, (S)-1-yl | F, pyridin-5-yl | H | 407.1132 |
| 3.22 | 3-methyl-1,2,4-oxadiazol-5-yl, (S)-1-yl | phenyl | isopropoxy | 381.1928 |

TABLE 3-continued

| Example | R$^x$ | R$^y$ | R$^z$ | MS (M + 1) |
|---|---|---|---|---|
| 3.23 | 2-CF$_3$-pyridin-5-yl N-oxide, CH(CH$_3$)- | 4-substituted phenyl | -O-CH(CH$_3$)$_2$ | 460.1849 |
| 3.24 | 3-methyl-1,2,4-oxadiazol-5-yl, CH(CH$_3$)- | 4-F-phenyl | -O-CH(CH$_3$)$_2$ | 385.1685 |
| 3.25 | 2-CF$_3$-pyrimidin-5-yl, CH(CH$_3$)- | 2,4-diF-phenyl | H | 409.1085 |
| 3.26 | 2-methyl-pyrimidin-5-yl, CH(CH$_3$)- | 2,5-diF-phenyl | H | 355.1385 |
| 3.27 | 3-methyl-1,2,4-oxadiazol-5-yl, CH(CH$_3$)- | 4-substituted phenyl | -O-(1-methyl-imidazol-2-yl) | 419.1834 |

TABLE 3-continued

| Example | R^x | R^y | R^z | MS (M + 1) |
|---|---|---|---|---|
| 3.28 | 4H-1,2,4-triazol-3-yl CH(CH3) | 2,4-difluorophenyl | H | 330.1160 |
| 3.29 | 4H-1,2,4-triazol-3-yl CH(CH3) | phenyl | H | 308.1506 |
| 3.30 | 4H-1,2,4-triazol-3-yl CH(CH3) | phenyl | OiPr | 366.1925 |
| 3.31 | 4H-1,2,4-triazol-3-yl CH(CH3) | 4-fluorophenyl | OiPr | 370.1673 |
| 3.32 | 4H-1,2,4-triazol-3-yl CH(CH3) | pyridin-3-yl | H | 309.1459 |
| 3.33 | 2-(trifluoromethyl)pyridin-5-yl N-oxide CH(CH3) | 4-chlorophenyl | H | 422.0886 |

TABLE 3-continued

| Example | R$^x$ | R$^y$ | R$^z$ | MS (M + 1) |
|---|---|---|---|---|
| 3.34 | 2-(trifluoromethyl)pyridin-5-yl N-oxide, (S)-methyl | 5-chloropyridin-2-yl | H | 423.0837 |
| 3.35 | 2-(trifluoromethyl)pyridin-5-yl N-oxide, (S)-methyl | phenyl (1,4) | OMe | 432.1538 |
| 3.36 | 3-methyl-1,2,4-oxadiazol-5-yl, (S)-methyl | phenyl (1,4) | OMe | 353.1611 |
| 3.37 | 4H-1,2,4-triazol-3-yl, (S)-methyl | phenyl (1,4) | OMe | 338.1613 |
| 3.38 | 2-(trifluoromethyl)pyridin-5-yl N-oxide, (S)-methyl | 4-fluorophenyl | OCH$_2$CH$_2$CF$_3$ | 518.1327 |

TABLE 3-continued

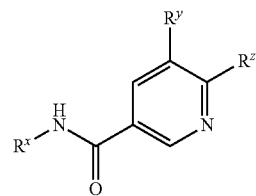

| Example | R$^x$ | R$^y$ | R$^z$ | MS (M + 1) |
|---|---|---|---|---|
| 3.39 | 2-(trifluoromethyl)pyridine 1-oxide with chiral methyl linker | 4-F-phenyl | O-cyclobutyl | 476.1603 |
| 3.40 | 2-(trifluoromethyl)pyridine 1-oxide with chiral methyl linker | 4-F-phenyl | OCH$_3$ | 436.1288 |
| 3.41 | 2-(trifluoromethyl)pyridine 1-oxide with chiral methyl linker | 4-F-phenyl | OCH$_2$-cyclopropyl | 476.1598 |
| 3.42 | 2-(trifluoromethyl)pyridine 1-oxide with chiral methyl linker | 4-F-phenyl | O-(tetrahydrofuran-3-yl) | 492.1524 |
| 3.43 | 3-methyl-1,2,4-oxadiazol-5-yl with chiral methyl linker | 4-F-phenyl | O-(tetrahydrofuran-3-yl) | 413.1610 |

TABLE 3-continued
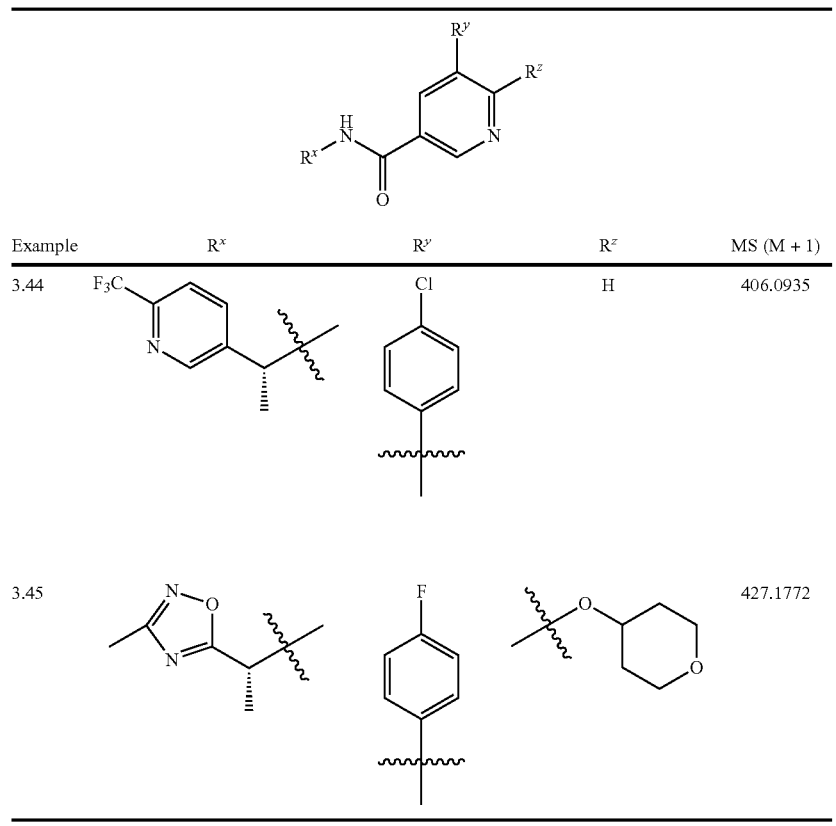
TABLE 4 / TABLE 4-continued
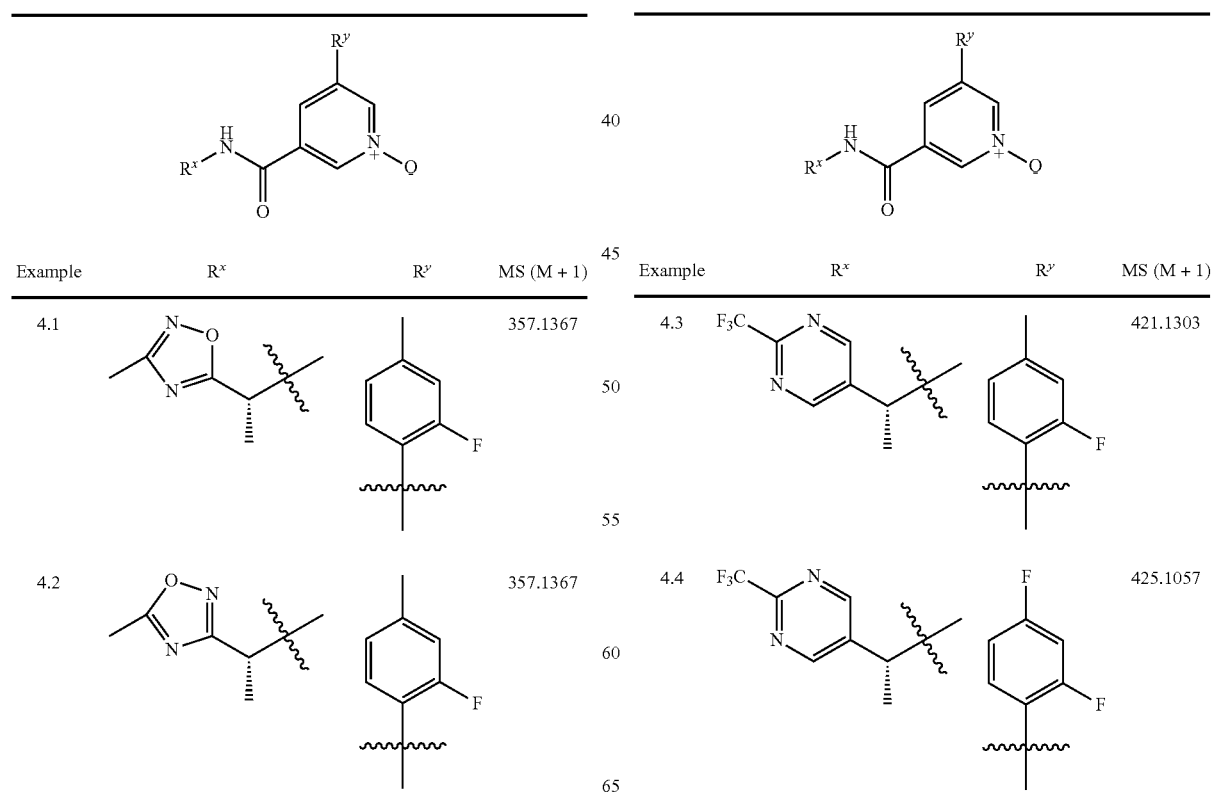

TABLE 4-continued

[Structure: R^y-substituted pyridine N-oxide with R^x-NH-C(=O)- group]

| Example | R^x | R^y | MS (M + 1) |
|---------|-----|-----|------------|
| 4.5 | 3-methyl-1,2,4-oxadiazol-5-yl with (S)-CH(CH3) linker | 2,4-difluorophenyl | 361.1121 |
| 4.6 | 5-methyl-1,2,4-oxadiazol-3-yl with (S)-CH(CH3) linker | 2,4-difluorophenyl | 361.1119 |

TABLE 5

[Structure: 2-oxo-1,2-dihydropyridine-5-carboxamide with R^x-NH-C(=O)- at 5-position, R^y at 3-position, R^z on N1]

| Example | R^x | R^y | R^z | MS (M + 1) |
|---------|-----|-----|-----|------------|
| 5.1 | 5-fluoropyridin-2-yl with (S)-CH(CH3) linker | 4-methylphenyl | 4-methylphenyl | 442.1934 |
| 5.2 | 4H-1,2,4-triazol-3-yl with (S)-CH(CH3) linker | 4-methylphenyl | 4-methylphenyl | 414.1936 |
| 5.3 | 5-fluoropyridin-2-yl with (S)-CH(CH3) linker | 4-methylphenyl | 5-methylpyridin-2-yl | 443.1881 |

TABLE 5-continued

| Example | R$^x$ | R$^y$ | R$^z$ | MS (M + 1) |
|---|---|---|---|---|
| 5.4 | 1H-1,2,4-triazol-3-yl, (S)-1-methylethyl linker | 4-phenylene | 5-methylpyridin-2-yl | 415.1881 |
| 5.5 | 3-methyl-1,2,4-oxadiazol-5-yl, (S)-1-methylethyl linker | 4-phenylene | 5-methylpyridin-2-yl | 430.1881 |
| 5.6 | 3-methyl-1,2,4-oxadiazol-5-yl, (S)-1-methylethyl linker | pyridin-2-yl | 5-methylpyridin-2-yl | 417.1668 |
| 5.7 | 1H-1,2,4-triazol-3-yl, (S)-1-methylethyl linker | pyridin-2-yl | 5-methylpyridin-2-yl | 402.1670 |
| 5.8 | 2-(trifluoromethyl)pyrimidin-5-yl, (S)-1-methylethyl linker | pyridin-2-yl | 5-methylpyridin-2-yl | 481.1597 |
| 5.9 | 3-methyl-1,2,4-oxadiazol-5-yl, (S)-1-methylethyl linker | morpholin-4-yl | 4-phenylene | 424.1982 |

TABLE 5-continued

| Example | R$^x$ | R$^y$ | R$^z$ | MS (M + 1) |
|---|---|---|---|---|
| 5.10 | 2-(trifluoromethyl)pyrimidin-5-yl with CH(CH$_3$) linker | morpholin-4-yl | 4-methylphenyl | 488.1914 |
| 5.11 | 4H-1,2,4-triazol-3-yl with CH(CH$_3$) linker | morpholin-4-yl | 4-methylphenyl | 409.1986 |
| 5.12 | 3-methyl-1,2,4-oxadiazol-5-yl with CH(CH$_3$) linker | morpholin-4-yl | 5-methylpyridin-2-yl | 425.1935 |
| 5.13 | 2-(trifluoromethyl)pyrimidin-5-yl with CH(CH$_3$) linker | morpholin-4-yl | 5-methylpyridin-2-yl | 489.1870 |
| 5.14 | 2-(trifluoromethyl)pyrimidin-5-yl with CH(CH$_3$) linker | cyclopropyl | 5-methylpyridin-2-yl | 444.1636 |
| 5.15 | 2-(trifluoromethyl)pyrimidin-5-yl with CH(CH$_3$) linker | 2,4-difluorophenyl | 5-methylpyridin-2-yl | 516.1442 |
| 5.16 | 3-methyl-1,2,4-oxadiazol-5-yl with CH(CH$_3$) linker | 6-methylpyridin-3-yl | tert-butyl | 354.1555 |

TABLE 5-continued

| Example | R$^x$ | R$^y$ | R$^z$ | MS (M + 1) |
|---|---|---|---|---|
| 5.17 | F$_3$C-pyrimidine-CH(CH$_3$)- | -C(CH$_3$)$_2$OH | 5-methylpyridin-2-yl | 462.1761 |
| 5.18 | F$_3$C-pyrimidine-CH(CH$_3$)- | pyrimidin-5-yl | 5-methylpyridin-2-yl | 496.1720 |
| 5.19 | F$_3$C-pyrimidine-CH(CH$_3$)- | 2-aminopyrimidin-5-yl | 5-methylpyridin-2-yl | 497.1680 |
| 5.20 | F$_3$C-pyrimidine-CH(CH$_3$)- | isopropyl | 5-methylpyridin-2-yl | 446.1804 |
| 5.21 | F$_3$C-pyrimidine-CH(CH$_3$)- | 4-methylphenyl | 5-methylpyridin-2-yl | 494.1814 |
| 5.22 | F$_3$C-pyrimidine-CH(CH$_3$)- | 4-methylphenyl | -CH(CH$_3$)CH$_2$CF$_3$ | 485.1425 |

TABLE 5-continued

| Example | R$^x$ | R$^y$ | R$^z$ | MS (M + 1) |
|---|---|---|---|---|
| 5.23 | 3-methyl-1,2,4-oxadiazol-5-yl with (S)-methyl linker | 4-phenyl | CH$_2$CF$_3$ branched | 421.1497 |
| 5.24 | 5-methyl-1,2,4-oxadiazol-3-yl with (S)-methyl linker | 4-phenyl | CH$_2$CF$_3$ branched | 421.1495 |
| 5.25 | 4H-1,2,4-triazol-3-yl with (S)-methyl linker | 4-phenyl | CH$_2$CF$_3$ branched | 406.1480 |
| 5.26 | 5-fluoropyridin-2-yl N-oxide with (S)-methyl linker | 4-phenyl | CH$_2$CF$_3$ branched | 450.1437 |
| 5.27 | 2-(trifluoromethyl)pyridin-5-yl N-oxide with (S)-methyl linker | 4-phenyl | CH$_2$CF$_3$ branched | 500.1395 |
| 5.28 | 3-methyl-1,2,4-oxadiazol-5-yl with (S)-methyl linker | C(CH$_3$)$_2$OH | 4-methylphenyl | 397.1890 |

TABLE 5-continued
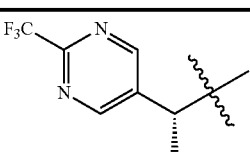
| Example | R$^x$ | R$^y$ | R$^z$ | MS (M + 1) |
|---|---|---|---|---|
| 5.29 | 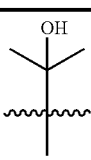 | 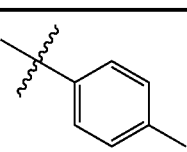 | 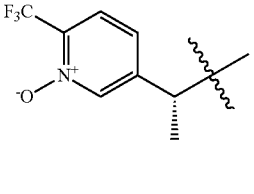 | 461.1820 |
| 5.30 | 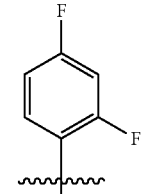 | 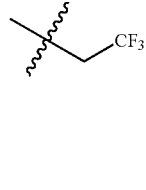 | 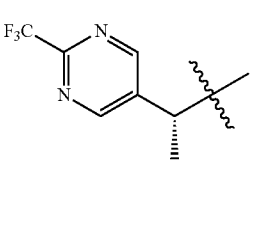 [SMILES: *[C@H](C)c1cnc(C(F)(F)F)nc1] | 522.1089 |
| 5.31 | 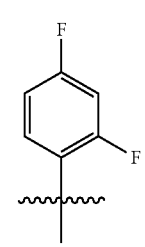 [SMILES: *c1ccc(F)cc1F] | 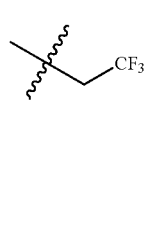 | 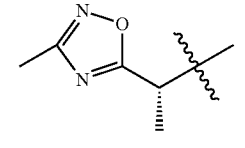 [SMILES: *[C@H](C)c1nc(C)no1] | 507.1084 |
| 5.32 | 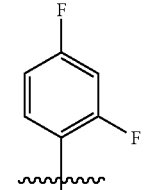 | 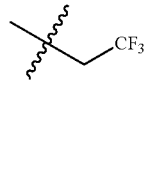 [SMILES: *CC(F)(F)F] | 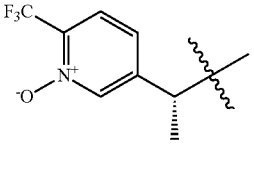 | 443.1159 |
| 5.33 | 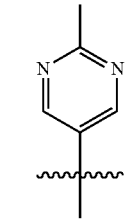 [SMILES: *c1cnc(C)nc1] | 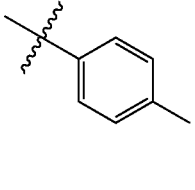 [SMILES: *c1ccc(C)cc1] | 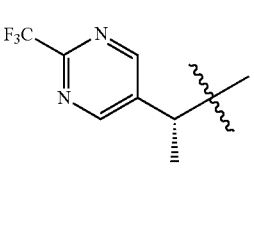 [SMILES: *[C@H](C)c1cnc(C(F)(F)F)nc1] | 510.1754 |
| 5.34 | 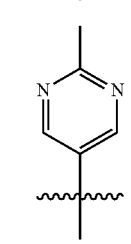 | 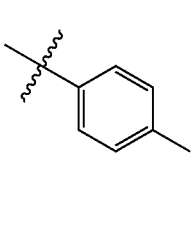 | | 495.1760 |

TABLE 5-continued

| Example | R^x | R^y | R^z | MS (M + 1) |
|---|---|---|---|---|
| 5.35 | 3-methyl-1,2,4-oxadiazol-5-yl (R)-ethyl | pyrimidin-5-yl | p-phenylene | 431.1832 |
| 5.36 | 2-(trifluoromethyl)pyridin-5-yl N-oxide (S)-ethyl | pyridin-2-yl | p-phenylene | 509.1789 |
| 5.37 | 2-(trifluoromethyl)pyrimidin-5-yl (S)-ethyl | pyridin-2-yl | p-phenylene | 494.1790 |
| 5.38 | 3-methyl-1,2,4-oxadiazol-5-yl (S)-ethyl | pyridin-2-yl | p-phenylene | 430.1869 |
| 5.39 | 3-methyl-1,2,4-oxadiazol-5-yl (S)-ethyl | 2,4-difluorophenyl | 5-methylpyridin-2-yl | 452.1505 |
| 5.40 | 3-methyl-1,2,4-oxadiazol-5-yl (S)-ethyl | 2,4-difluorophenyl | tert-butyl | 403.1569 |

TABLE 5-continued

| Example | R^x | R^y | R^z | MS (M + 1) |
|---|---|---|---|---|
| 5.41 | F₃C-pyridine N-oxide with CH(CH₃) linker | 2,4-difluorophenyl | isopropyl | 482.1466 |
| 5.42 | F₃C-pyridine N-oxide with CH(CH₃) linker | 4-phenyl | 2-pyridyl | 495.1645 |
| 5.43 | F₃C-pyrimidine with CH(CH₃) linker | 4-phenyl | 2-pyridyl | 480.1648 |
| 5.44 | 3-methyl-1,2,4-oxadiazole with CH(CH₃) linker | 4-phenyl | 2-pyridyl | 416.1723 |
| 5.45 | 1H-1,2,4-triazole with CH(CH₃) linker | 4-phenyl | 2-pyridyl | 401.1726 |

TABLE 5-continued

| Example | R^x | R^y | R^z | MS (M + 1) |
|---|---|---|---|---|
| 5.46 | F3C-pyrimidine-CH(CH3)- | F (4-F-phenyl) | 5-methylpyridin-2-yl | 498.1556 |
| 5.47 | F3C-pyrimidine-CH(CH3)- | 3,4-diF-phenyl | 5-methylpyridin-2-yl | 516.1468 |
| 5.48 | F3C-pyrimidine-CH(CH3)- | 4-Cl-phenyl | 5-methylpyridin-2-yl | 514.1276 |
| 5.49 | F3C-pyrimidine-CH(CH3)- | 3-F-phenyl | 5-methylpyridin-2-yl | 498.1561 |
| 5.50 | F3C-pyrimidine-CH(CH3)- | 3-methylphenyl | 5-methylpyridin-2-yl | 494.1809 |
| 5.51 | F3C-pyrimidine-CH(CH3)- | phenyl | 5-methylpyridin-2-yl | 480.1666 |

TABLE 5-continued

| Example | R<sup>x</sup> | R<sup>y</sup> | R<sup>z</sup> | MS (M + 1) |
|---------|---------------|---------------|---------------|------------|
| 5.52 | 2-(trifluoromethyl)pyrimidin-5-yl, CH(CH₃)– | 4-(CF₃)phenyl | 5-methylpyridin-2-yl | 548.1534 |
| 5.53 | 2-(trifluoromethyl)pyrimidin-5-yl, CH(CH₃)– | 4-(OMe)phenyl | 5-methylpyridin-2-yl | 510.1764 |
| 5.54 | 2-(trifluoromethyl)pyrimidin-5-yl, CH(CH₃)– | 4-(CN)phenyl | 5-methylpyridin-2-yl | 505.1615 |
| 5.55 | 3-methyl-1,2,4-oxadiazol-5-yl, CH(CH₃)– | phenyl | 2-methylpyrimidin-5-yl | 431.1850 |
| 5.56 | 3-methyl-1,2,4-oxadiazol-5-yl, CH(CH₃)– | phenyl | isopropyl | 381.1928 |
| 5.57 | 4H-1,2,4-triazol-3-yl, CH(CH₃)– | phenyl | isopropyl | 366.1930 |

TABLE 5-continued

| Example | R^x | R^y | R^z | MS (M + 1) |
|---|---|---|---|---|
| 5.58 | 2-(trifluoromethyl)pyrimidin-5-yl with (S)-methyl linker | 4-phenyl | tert-butyl | 445.1870 |
| 5.59 | 6-(trifluoromethyl)pyridin-3-yl N-oxide with (S)-methyl linker | 4-phenyl | tert-butyl | 460.1859 |
| 5.60 | 6-(trifluoromethyl)pyridin-3-yl N-oxide with (S)-methyl linker | C(CH₃)₂OH | 4-methylphenyl | 476.1801 |
| 5.61 | 3-methyl-1,2,4-oxadiazol-5-yl with (S)-methyl linker | 4-fluorophenyl | tert-butyl | 385.1685 |
| 5.62 | 2-(trifluoromethyl)pyrimidin-5-yl with (S)-methyl linker | 4-fluorophenyl | tert-butyl | 449.1617 |
| 5.63 | 6-(trifluoromethyl)pyridin-3-yl N-oxide with (S)-methyl linker | 4-fluorophenyl | tert-butyl | 464.1607 |

TABLE 5-continued

| Example | R$^x$ | R$^y$ | R$^z$ | MS (M + 1) |
|---|---|---|---|---|
| 5.64 | 3-methyl-1,2,4-oxadiazol-5-yl-CH(CH₃)– | 4-phenylene | 1-methylimidazol-2-yl | 419.1833 |
| 5.65 | 2-(trifluoromethyl)pyrimidin-5-yl-CH(CH₃)– | 4-phenylene | isopropyl | 391.2142 |
| 5.66 | 3-methyl-1,2,4-oxadiazol-5-yl-CH(CH₃)– | 4-phenylene | tert-butyl | 353.1629 |
| 5.67 | 3-methyl-1,2,4-oxadiazol-5-yl-CH(CH₃)– | 3-F-4-phenylene | tert-butyl | 357.1377 |
| 5.68 | 2-(trifluoromethyl)pyrimidin-5-yl-CH(CH₃)– | 3-F-4-phenylene | tert-butyl | 421.1297 |

TABLE 5-continued
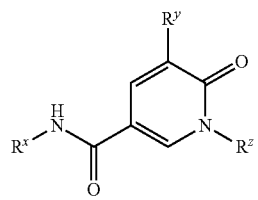
| Example | R$^x$ | R$^y$ | R$^z$ | MS (M + 1) |
|---|---|---|---|---|
| 5.69 | F$_3$C-pyridine N-oxide | 4-F-phenyl |  | 436.1295 |
| 5.70 | methyl-oxadiazole | phenyl | 5-F-pyridin-2-yl | 434.1635 |
| 5.71 | F$_3$C-pyrimidine | phenyl | 5-F-pyridin-2-yl | 498.1563 |
| 5.72 | F$_3$C-pyridine N-oxide | phenyl | 5-F-pyridin-2-yl | 513.1558 |
| 5.73 | methyl-oxadiazole | 4-F-phenyl | CH$_2$CF$_3$ | 425.1237 |

TABLE 5-continued
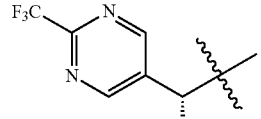
| Example | R$^x$ | R$^y$ | R$^z$ | MS (M + 1) |
|---|---|---|---|---|
| 5.74 | 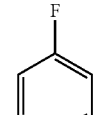 | 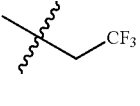 | 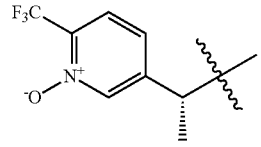 | 489.1162 |
| 5.75 | 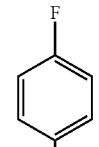 | 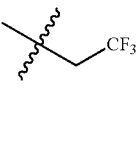 [SMILES: *CC(F)(F)F] | 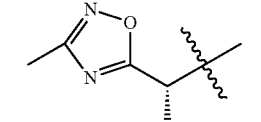 | 504.1164 |
| 5.76 | 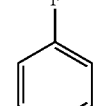 | 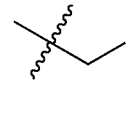 | 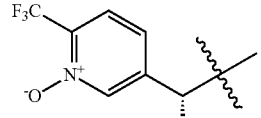 | 371.1513 |
| 5.77 | 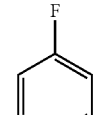 | 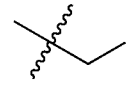 [SMILES: *CC] | 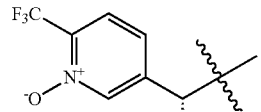 | 450.1448 |
| 5.78 | 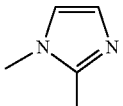 | 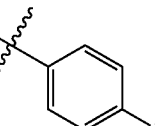 | 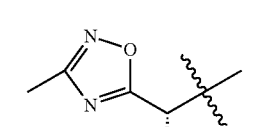 | 502.1497 |
| 5.79 | 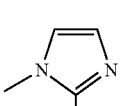 | 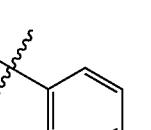 |  | 423.1575 |

TABLE 5-continued

| Example | R^x | R^y | R^z | MS (M + 1) |
|---------|-----|-----|-----|------------|
| 5.80 | F₃C-pyrimidine-CH(CH₃)- | N-methylimidazol-2-yl-C(CH₃)- | 4-fluorophenyl | 487.1497 |
| 5.81 | F₃C-pyridine N-oxide-CH(CH₃)- | oxazol-2-yl-C(CH₃)- | 4-fluorophenyl | 489.1183 |
| 5.82 | 3-methyl-1,2,4-oxadiazol-5-yl-CH(CH₃)- | oxazol-2-yl-C(CH₃)- | 4-fluorophenyl | 410.1258 |
| 5.83 | F₃C-pyrimidine-CH(CH₃)- | oxazol-2-yl-C(CH₃)- | 4-fluorophenyl | 474.1183 |
| 5.84 | F₃C-pyridine N-oxide-CH(CH₃)- | 4-fluorophenyl | 5-fluoropyridin-2-yl | 517.1283 |
| 5.85 | F₃C-pyrimidine-CH(CH₃)- | 4-fluorophenyl | pyridin-2-yl | 484.1385 |
| 5.86 | F₃C-pyridine N-oxide-CH(CH₃)- | 4-fluorophenyl | pyridin-2-yl | 499.1377 |

TABLE 5-continued

| Example | R$^x$ | R$^y$ | R$^z$ | MS (M + 1) |
|---|---|---|---|---|
| 5.87 | 3-methyl-1,2,4-oxadiazol-5-yl with (S)-methyl linker | 4-fluorophenyl | 5-fluoropyridin-2-yl | 438.1379 |
| 5.88 | 3-methyl-1,2,4-oxadiazol-5-yl with (S)-methyl linker | 4-fluorophenyl | pyridin-2-yl | 420.1470 |
| 5.89 | 3-methyl-1,2,4-oxadiazol-5-yl with (S)-methyl linker | 4-fluorophenyl | CH(CH$_3$)CH$_2$CF$_3$ | 439.1383 |
| 5.90 | 6-(trifluoromethyl)pyridin-1-oxide-3-yl with (S)-methyl linker | 4-fluorophenyl | CH(CH$_3$)CH$_2$CF$_3$ | 518.1337 |
| 5.91 | 2-(trifluoromethyl)pyrimidin-5-yl with (S)-methyl linker | 4-fluorophenyl | CH(CH$_3$)CH$_2$CF$_3$ | 503.1317 |

TABLE 5-continued

| Example | R<sup>x</sup> | R<sup>y</sup> | R<sup>z</sup> | MS (M + 1) |
|---------|---------------|---------------|---------------|------------|
| 5.92 | 2-(trifluoromethyl)pyridin-5-yl N-oxide with chiral methyl linker | 4-fluorophenyl | oxetan-3-yl | 478.1391 |
| 5.93 | 3-methyl-1,2,4-oxadiazol-5-yl with chiral methyl linker | 4-fluorophenyl | oxetan-3-yl | 399.1465 |
| 5.94 | 2-(trifluoromethyl)pyridin-5-yl N-oxide with chiral methyl linker | 4-methylphenyl | tert-butyl | 432.1541 |
| 5.95 | 2-(trifluoromethyl)pyridin-5-yl N-oxide with chiral methyl linker | 4-fluorophenyl | tetrahydrofuran-3-yl | 492.1556 |
| 5.96 | 3-methyl-1,2,4-oxadiazol-5-yl with chiral methyl linker | 4-fluorophenyl | tetrahydrofuran-3-yl | 413.1624 |

TABLE 5-continued
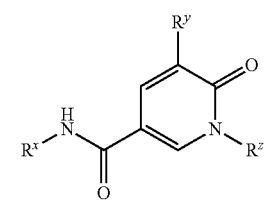
| Example | R$^x$ | R$^y$ | R$^z$ | MS (M + 1) |
|---|---|---|---|---|
| 5.97 | | | | 400.1479 |
| 5.98 | | | | 385.1661 |
| 5.99 | | | | 415.1764 |
| 5.100 | | | | 494.1679 |
| 5.101 | | | | 397.1675 |

TABLE 5-continued
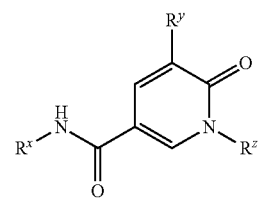
| Example | R$^x$ | R$^y$ | R$^z$ | MS (M + 1) |
|---|---|---|---|---|
| 5.102 | 3-methyl-1,2,4-oxadiazol-5-yl CH(CH₃)- | 4-F-phenyl | CH₂-cyclopropyl | 397.1675 |
| 5.103 | 5-methyl-1,2,4-oxadiazol-3-yl CH(CH₃)- | 4-F-phenyl | 2-pyridyl | 420.1472 |
| 5.104 | 6-(trifluoromethyl)pyridin-3-yl N-oxide CH(CH₃)- | 4-F-phenyl | CH₂-cyclopropyl | 476.1576 |
| 5.105 | 6-(trifluoromethyl)pyridin-3-yl N-oxide CH(CH₃)- | 4-F-phenyl | cyclobutyl | 476.1600 |
| 5.106 | 3-methyl-1,2,4-oxadiazol-5-yl CH(CH₃)- | 4-F-phenyl | 2-thiazolyl | 426.1031 |

TABLE 5-continued

| Example | R^x | R^y | R^z | MS (M + 1) |
|---|---|---|---|---|
| 5.107 | (4H-1,2,4-triazol-3-yl)(methyl)methyl | F-phenyl | thiazol-2-yl | 411.1034 |
| 5.108 | (2-(trifluoromethyl)pyrimidin-5-yl)(methyl)methyl | F-phenyl | thiazol-2-yl | 490.0955 |
| 5.109 | (3-methyl-1,2,4-oxadiazol-5-yl)(methyl)methyl | F-phenyl | 2-methylpyrimidin-5-yl | 435.1565 |
| 5.110 | (2-(trifluoromethyl)pyridin-5-yl 1-oxide)(methyl)methyl | F-phenyl | thiazol-2-yl | 505.1 |
| 5.111 | (3-methyl-1,2,4-oxadiazol-5-yl)(methyl)methyl | Cl-phenyl | pyridin-2-yl | 436.1159 |

TABLE 5-continued
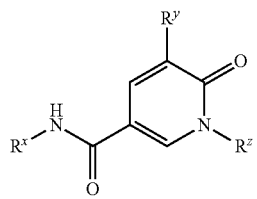
| Example | R$^x$ | R$^y$ | R$^z$ | MS (M + 1) |
|---|---|---|---|---|
| 5.112 | 2-CF$_3$-pyridin-5-yl N-oxide, CH(CH$_3$)- | Cl (4-Cl-phenyl) | pyridin-2-yl | 515.1073 |
| 5.113 | 2-CF$_3$-pyridin-5-yl N-oxide, CH(CH$_3$)- | F (4-F-phenyl) | 2-methylpyrimidin-5-yl | 514.1479 |
| 5.114 | 5-methyl-1,2,4-oxadiazol-3-yl, CH(CH$_3$)- | Cl (4-Cl-phenyl) | pyridin-2-yl | 436.1157 |
| 5.115 | 4H-1,2,4-triazol-3-yl, CH(CH$_3$)- | Cl (4-Cl-phenyl) | pyridin-2-yl | 421.1165 |
| 5.116 | 2-CF$_3$-pyridin-5-yl N-oxide, CH(CH$_3$)- | Cl (4-Cl-phenyl) | 5-methylpyridin-2-yl | 529.1253 |

TABLE 5-continued

| Example | R$^x$ | R$^y$ | R$^z$ | MS (M + 1) |
|---|---|---|---|---|
| 5.117 | 3-methyl-1,2,4-oxadiazol-5-yl-CH(CH$_3$)- | Cl (on phenyl) | 5-methylpyridin-2-yl | 450.1331 |
| 5.118 | 2-(trifluoromethyl)pyrimidin-5-yl-CH(CH$_3$)- | Cl (on phenyl) | pyridin-2-yl | 500.1095 |
| 5.119 | 2-(trifluoromethyl)pyrimidin-5-yl-CH(CH$_3$)- | F (on phenyl) | thiazol-5-yl | 490.0952 |
| 5.120 | 3-methyl-1,2,4-oxadiazol-5-yl-CH(CH$_3$)- | F (on phenyl) | thiazol-5-yl | 426.1029 |
| 5.121 | 2-(trifluoromethyl)pyridin-1-oxide-5-yl-CH(CH$_3$)- | F (on phenyl) | thiazol-5-yl | 505.0958 |

TABLE 5-continued

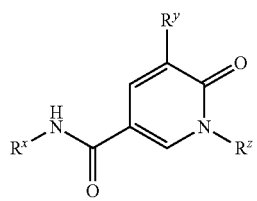

| Example | R$^x$ | R$^y$ | R$^z$ | MS (M + 1) |
|---|---|---|---|---|
| 5.122 | 3-methyl-1,2,4-oxadiazol-5-yl with CH(CH₃) linker | 4-F-phenyl | thiazol-4-yl | 426.1036 |
| 5.123 | 2-(trifluoromethyl)pyridine 1-oxide-5-yl with CH(CH₃) linker | 4-F-phenyl | thiazol-5-yl | 505.0951 |
| 5.124 | 2-(trifluoromethyl)pyrimidin-5-yl with CH(CH₃) linker | 4-F-phenyl | thiazol-4-yl | 490.0957 |
| 5.125 | 2-(trifluoromethyl)pyrimidin-5-yl with CH(CH₃) linker | 4-OH-phenyl | 5-methylpyridin-2-yl | 496.1600 |
| 5.126 | 2-(trifluoromethyl)pyrimidin-5-yl with CH(CH₃) linker | 4-F-phenyl | 1-methylimidazol-2-yl | 487.1505 |

TABLE 5-continued

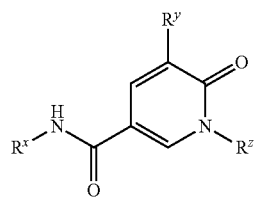

| Example | R$^x$ | R$^y$ | R$^z$ | MS (M + 1) |
|---|---|---|---|---|
| 5.127 | 3-methyl-1,2,4-oxadiazol-5-yl CH(CH$_3$)- | 4-F-phenyl | 1-methylimidazol-2-yl | 423.1579 |
| 5.128 | 2-(trifluoromethyl)pyridin-5-yl N-oxide CH(CH$_3$)- | 4-F-phenyl | 1-methylimidazol-2-yl | 502.1500 |
| 5.129 | 2-(trifluoromethyl)pyrimidin-5-yl CH(CH$_3$)- | 4-F-phenyl | 1-methylimidazol-4-yl | 487.1509 |
| 5.130 | 2-(trifluoromethyl)pyridin-5-yl N-oxide CH(CH$_3$)- | 4-F-phenyl | 1-methylimidazol-4-yl | 502.1505 |
| 5.131 | 3-methyl-1,2,4-oxadiazol-5-yl CH(CH$_3$)- | 4-F-phenyl | 1-methylimidazol-4-yl | 423.1583 |

TABLE 5-continued

| Example | Rˣ | Rʸ | Rᶻ | MS (M + 1) |
|---|---|---|---|---|
| 5.132 | 2-CF₃-pyridine N-oxide, 5-yl with (S)-methyl | 4-F-phenyl | C(CH₃)₂C(CH₃)₂OH | 508.1849 |
| 5.133 | 5-methyl-1,2,4-oxadiazol-3-yl with (S)-methyl | 4-F-phenyl | C(CH₃)₂C(CH₃)₂OH | 429.1939 |
| 5.134 | 3-methyl-1,2,4-oxadiazol-5-yl with (S)-methyl | 4-F-phenyl | C(CH₃)₂C(CH₃)₂OH | 429.1973 |
| 5.135 | 3-methyl-1,2,4-oxadiazol-5-yl with (S)-methyl | 4-F-phenyl | C(CH₃)₂CH(CH₃)OH | 429.1928 |
| 5.136 | 3-methyl-1,2,4-oxadiazol-5-yl with (S)-methyl | 4-F-phenyl | C(CH₃)₂CH(CH₃)OH | 429.1931 |

TABLE 5-continued
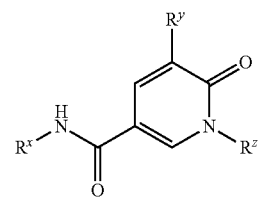
| Example | R$^x$ | R$^y$ | R$^z$ | MS (M + 1) |
|---------|-------|-------|-------|------------|
| 5.137 | | | | 445.1700 |
| | 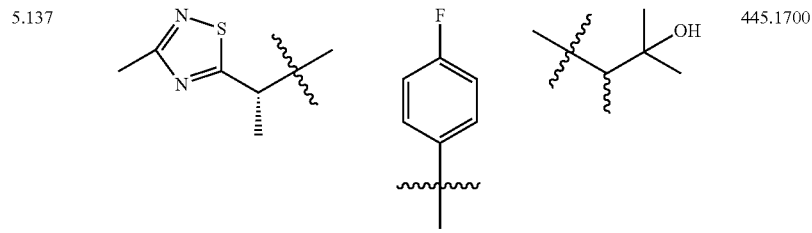 | | | |
| 5.138 | | | | 493.1856 |
| | 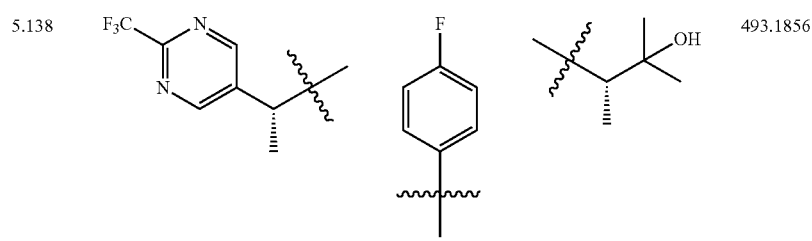 | | | |
| 5.139 | | | | 492.1905 |
| | 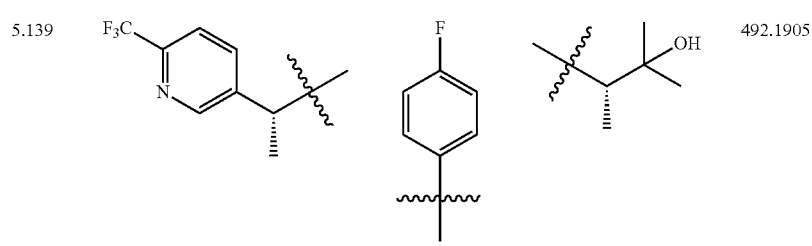 | | | |
| 5.140 | | | | 410.1270 |
| | 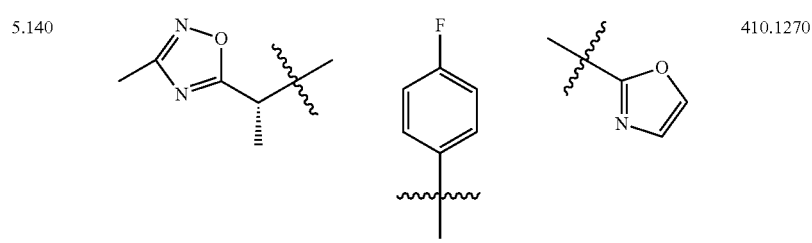 | | | |
| 5.141 | | | | 401.1442 |
| | 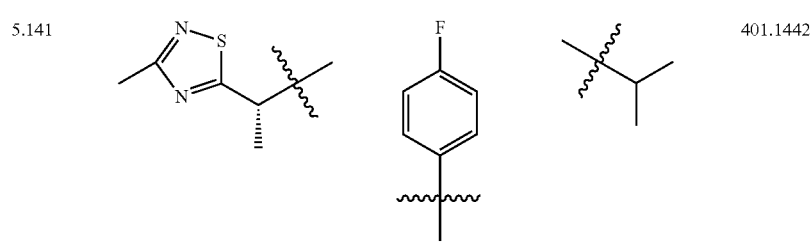 | | | |

TABLE 5-continued
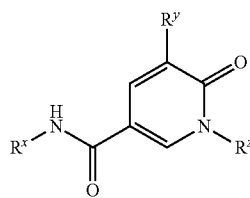
| Example | R$^x$ | R$^y$ | R$^z$ | MS (M + 1) |
|---|---|---|---|---|
| 5.142 | | F | | 401.1445 |
| 5.143 | | F | OH | 445.1713 |
| 5.144 | | Cl | CF$_3$ | 457.0704 |
| 5.145 | | F | N | 436.1247 |
| 5.146 | | Cl | CF$_3$ | 441.0941 |
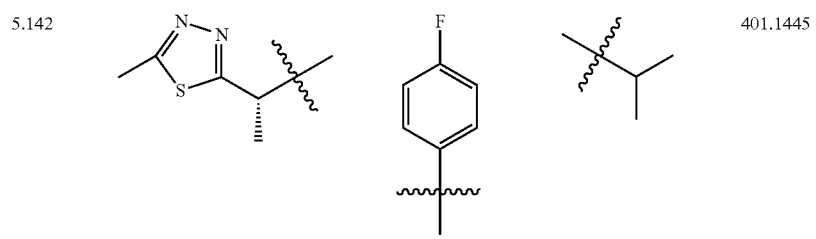
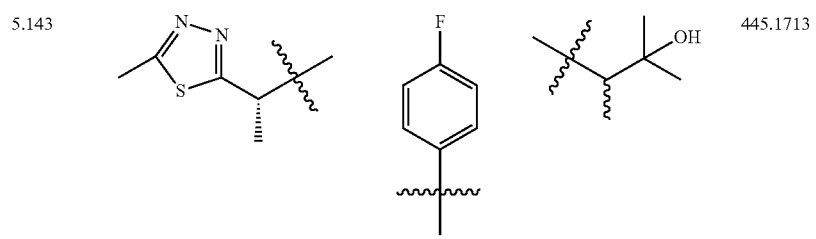
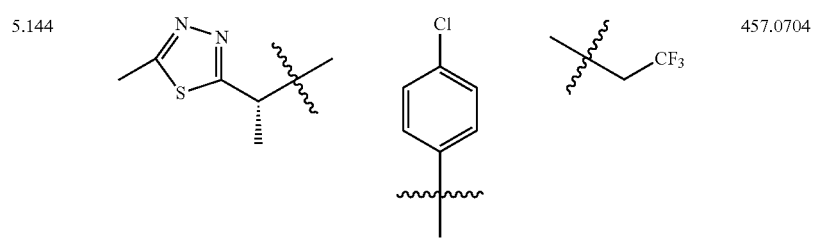
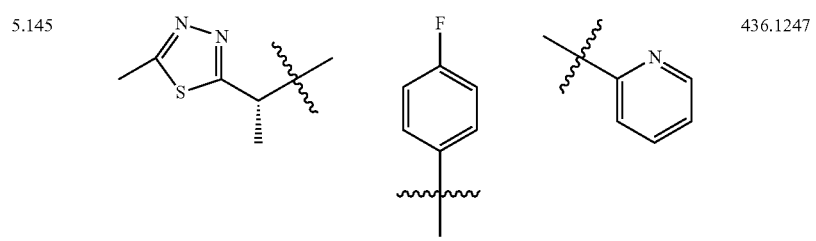
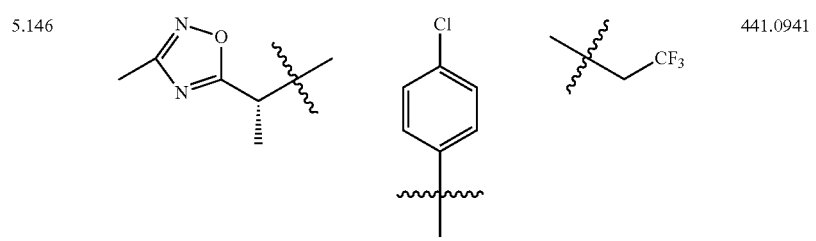

TABLE 5-continued
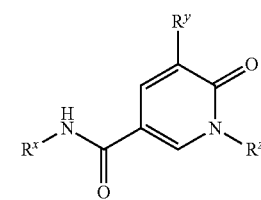
| Example | R$^x$ | R$^y$ | R$^z$ | MS (M + 1) |
|---|---|---|---|---|
| 5.147 | | Cl | | 441.0942 |
| 5.148 | | F | | 401.1452 |
| 5.149 | | Cl | | 461.1429 |
| 5.150 | | Cl | | 445.1646 |
| 5.151 | | Cl | | 445.1646 |
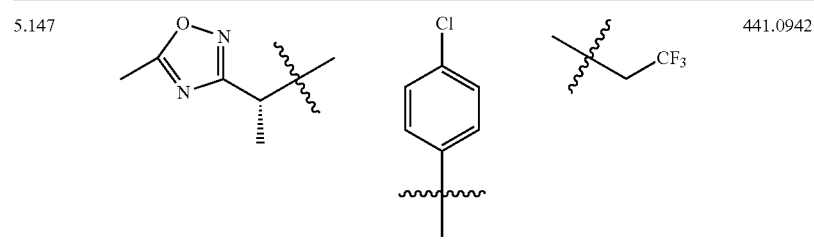
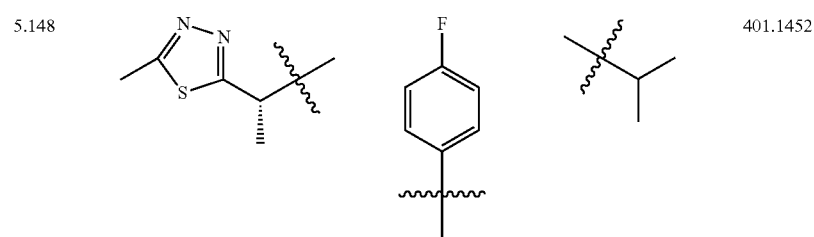
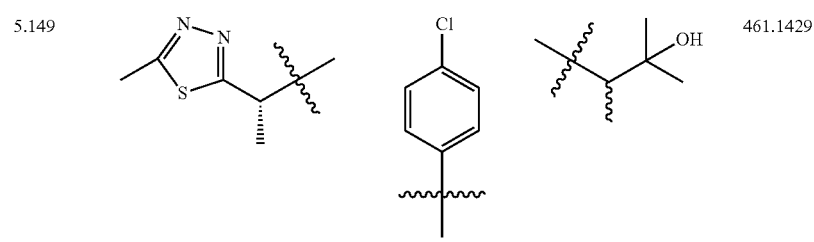
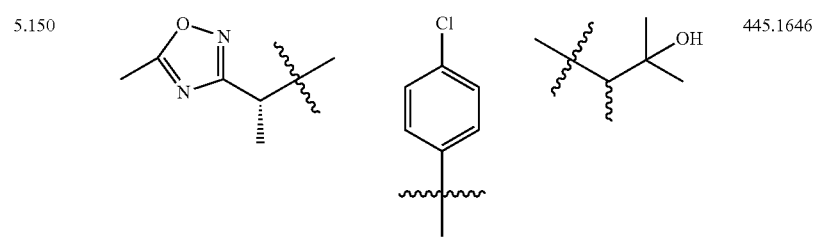
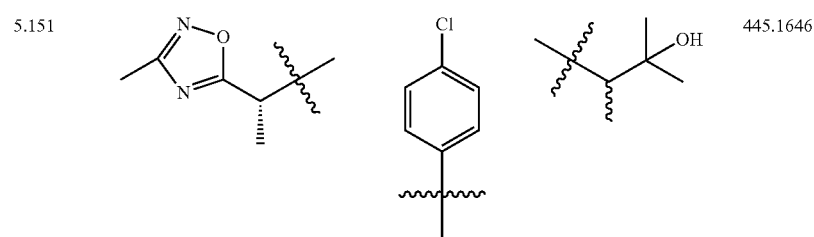

TABLE 5-continued
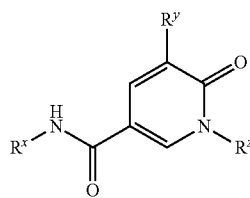
| Example | R$^x$ | R$^y$ | R$^z$ | MS (M + 1) |
|---|---|---|---|---|
| 5.152 | | F | OH | 431.1558 |
| 5.153 | | F | OH | 415.1784 |
| 5.154 | | F | OH | 415.1786 |
| 5.155 | | Cl | | 417.1161 |
| 5.156 | | Cl | | 401.1381 |

TABLE 5-continued
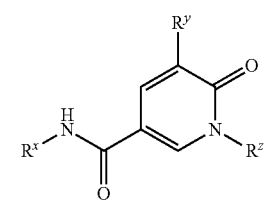
| Example | R^x | R^y | R^z | MS (M + 1) |
|---|---|---|---|---|
| 5.157 | | | | 401.1381 |
| 5.158 | | | | 446.1827 |
| 5.159 | | | | 426.1037 |
| 5.160 | | | | 442.0811 |
| 5.161 | | | | 442.0810 |
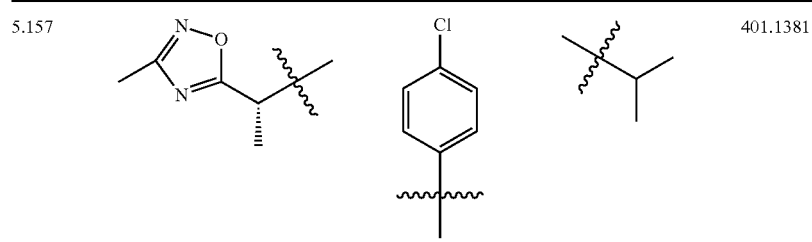
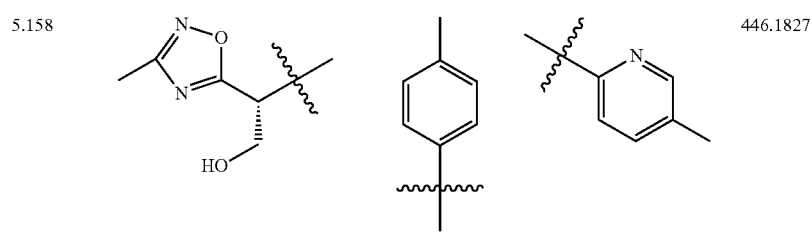
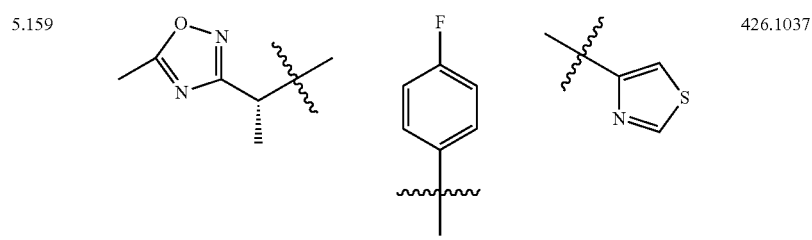
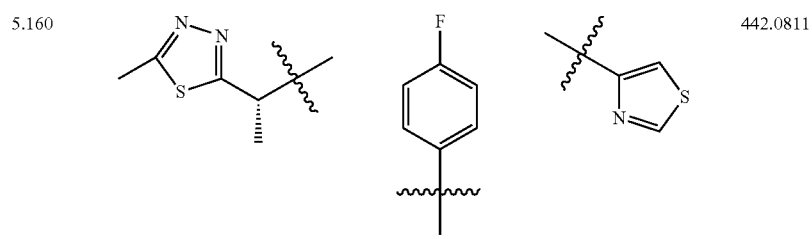
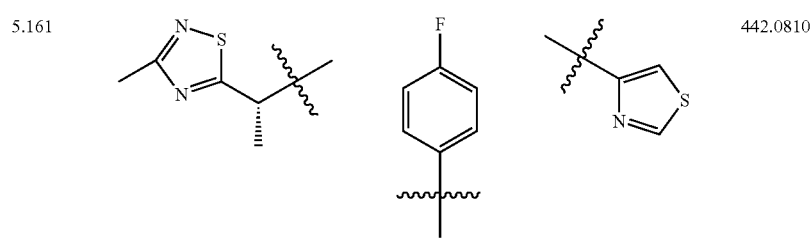

TABLE 5-continued

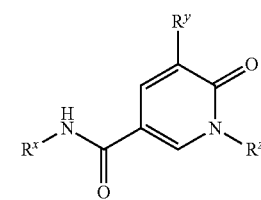

| Example | R$^x$ | R$^y$ | R$^z$ | MS (M + 1) |
|---|---|---|---|---|
| 5.162 | 3-methyl-1,2,4-thiadiazol-5-yl with (S)-methyl linker | 4-fluorophenyl | 2-methyl-1-hydroxypropan-2-yl | 417.1395 |
| 5.163 | 6-methoxypyridin-3-yl with (S)-CH$_2$OH linker | 4-fluorophenyl | isopropyl | 426.1824 |
| 5.164 | 5-methyl-1,3,4-thiadiazol-2-yl with (S)-methyl linker | 4-fluorophenyl | 2-methyl-1-hydroxypropan-2-yl | 417.1397 |
| 5.165 | 5-methyl-1,2,4-oxadiazol-3-yl with (S)-methyl linker | 4-fluorophenyl | 2-methyl-1-hydroxypropan-2-yl | 401.1627 |
| 5.166 | 3-methyl-1,2,4-oxadiazol-5-yl with (S)-methyl linker | 4-fluorophenyl | 2-methyl-1-hydroxypropan-2-yl | 401.1627 |

TABLE 5-continued

| Example | Rˣ | Rʸ | Rᶻ | MS (M + 1) |
|---------|----|----|----|------------|
| 5.167 | 3-methyl-1,2,4-oxadiazol-5-yl with (S)-CH(CH₃)- | 4-F-C₆H₄- | -C(CH₃)(CF₃)OH | 483.1652 |
| 5.168 | 3-methyl-1,2,4-oxadiazol-5-yl with -CH(CH₂OH)- | 4-F-C₆H₄- | isopropyl | 401.1621 |
| 5.169 | 3-methyl-1,2,4-thiadiazol-5-yl with (S)-CH(CH₃)- | 4-F-C₆H₄- | -CH(CH₃)OH | 431.1543 |
| 5.170 | 3-methyl-1,2,4-oxadiazol-5-yl with -CH(CH₂OH)- | 4-F-C₆H₄- | -C(CH₃)₂OH | 445.1877 |
| 5.171 | 3-methyl-1,2,4-oxadiazol-5-yl with (S)-CH(CH₃)- | 4-F-C₆H₄- | -CH(CF₃)CH(CH₃)OH | 455.1333 |

TABLE 5-continued
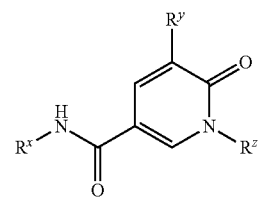
| Example | $R^x$ | $R^y$ | $R^z$ | MS (M + 1) |
|---|---|---|---|---|
| 5.172 | 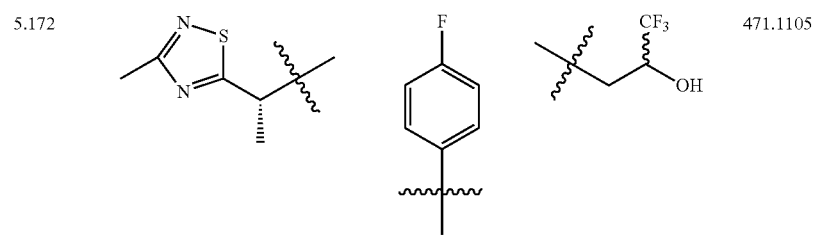 | | | 471.1105 |
| 5.173 | 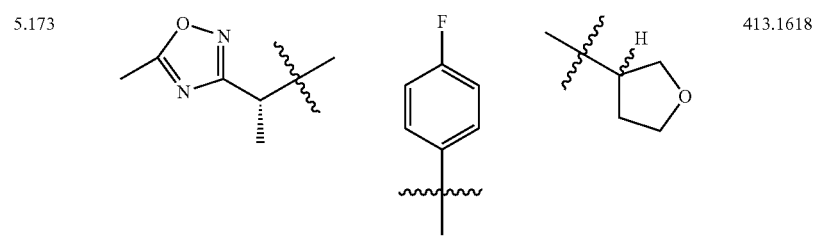 | | | 413.1618 |
| 5.174 | 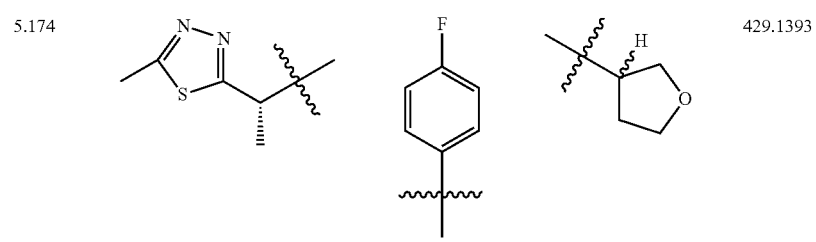 | | | 429.1393 |
| 5.175 | 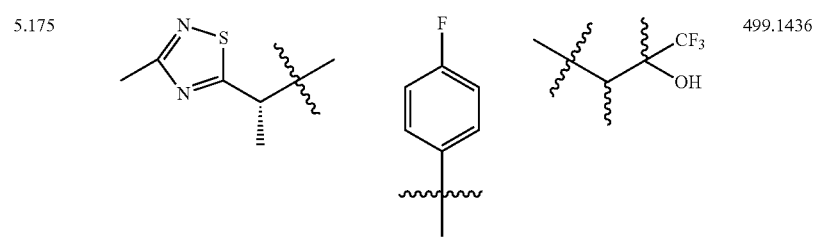 | | | 499.1436 |
| 5.176 | 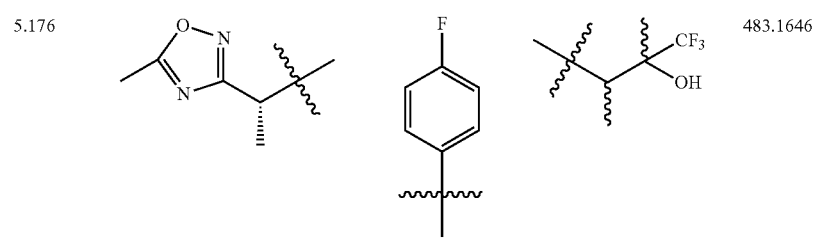 | | | 483.1646 |

TABLE 5-continued
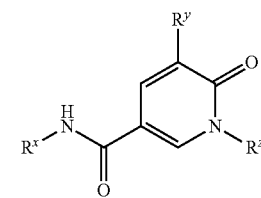
| Example | R$^x$ | R$^y$ | R$^z$ | MS (M + 1) |
|---|---|---|---|---|
| 5.177 | 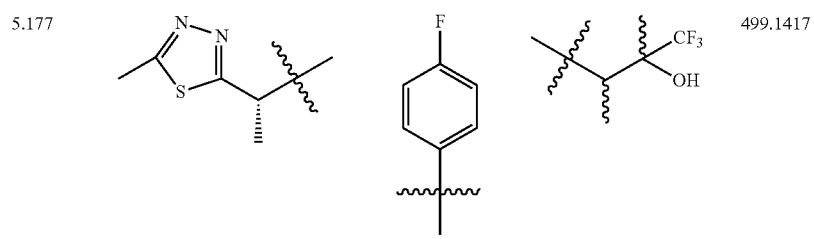 | | | 499.1417 |
| 5.178 | 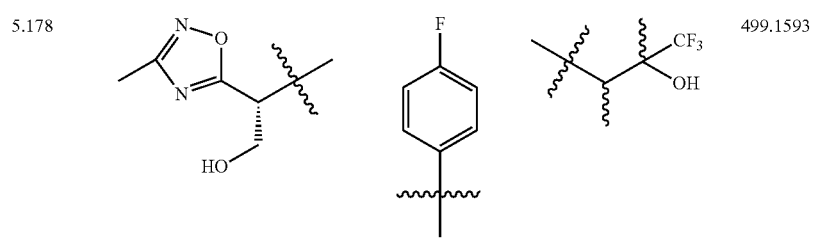 | | | 499.1593 |
| 5.179 | 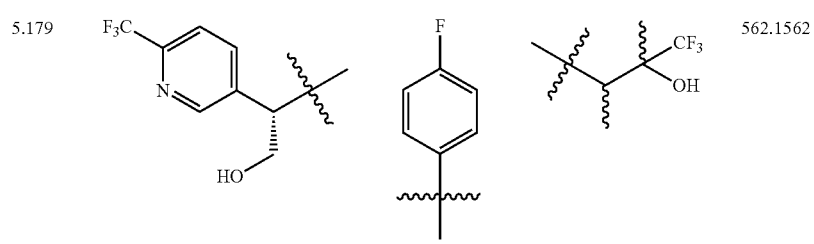 | | | 562.1562 |
| 5.180 | 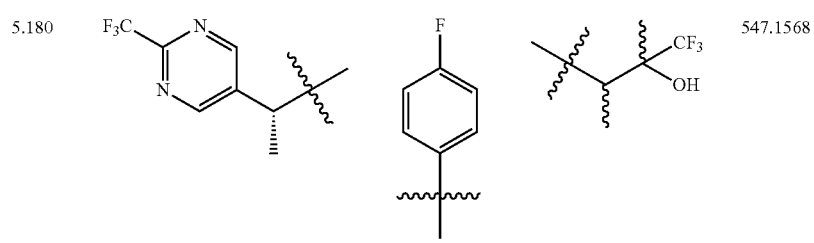 | | | 547.1568 |
| 5.181 | 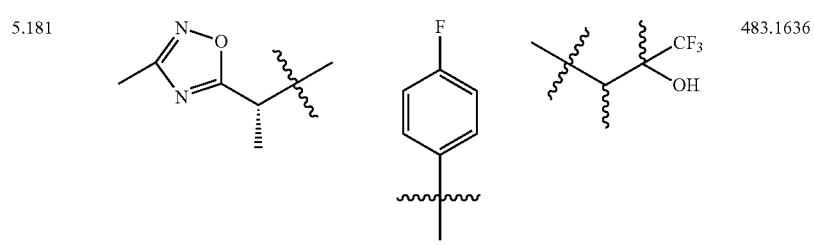 | | | 483.1636 |

TABLE 5-continued
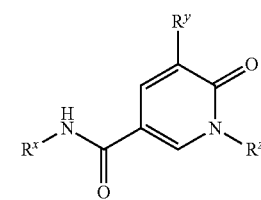
| Example | Rˣ | Rʸ | Rᶻ | MS (M + 1) |
|---|---|---|---|---|
| 5.182 | 3-methyl-1,2,4-oxadiazole-CH(CH₃)- | 4-F-phenyl | 2-cyclopropyl-thiazol-4-yl | 466.1346 |
| 5.183 | 3-methyl-1,2,4-oxadiazole-CH(CH₃)- | 4-F-phenyl | 2-methyl-thiazol-4-yl | 440.1188 |
| 5.184 | 3-methyl-1,2,4-oxadiazole-CH(CH₃)- | 4-F-phenyl | 2-hydroxycyclopentyl | 427.1778 |
| 5.185 | 3-methyl-1,2,4-oxadiazole-CH(CH₂OH)- | 4-F-phenyl | 3-hydroxy-3-methylbutan-2-yl | 445.1882 |
| 5.186 | 3-methyl-1,2,4-oxadiazole-CH(CH₃)- | 4-F-phenyl | 3-hydroxy-3-methylbutan-2-yl | 429.4 |

TABLE 5-continued
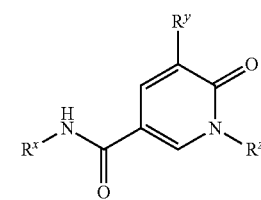
| Example | R$^x$ | R$^y$ | R$^z$ | MS (M + 1) |
|---|---|---|---|---|
| 5.187 | | | | 415.3 |
| 5.188 | | | | 415.3 |
| 5.189 | | | | 415.3 |
| 5.190 | | | | 415.3 |
| 5.191 | | | | 415.3 |

TABLE 5-continued
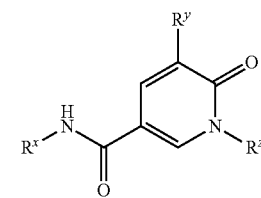
| Example | R$^x$ | R$^y$ | R$^z$ | MS (M + 1) |
|---|---|---|---|---|
| 5.192 | 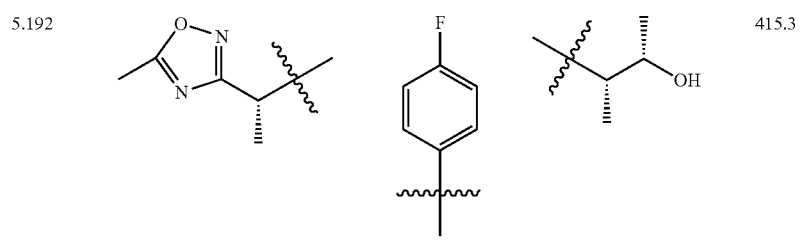 | | | 415.3 |
| 5.193 | 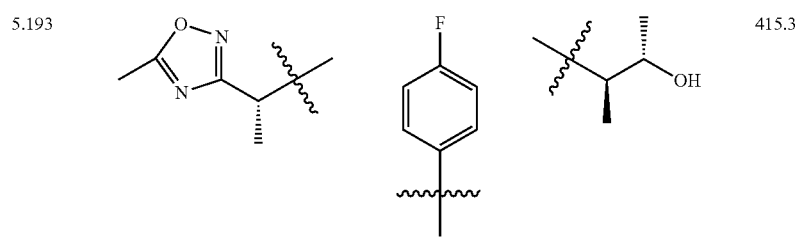 | | | 415.3 |
| 5.194 | 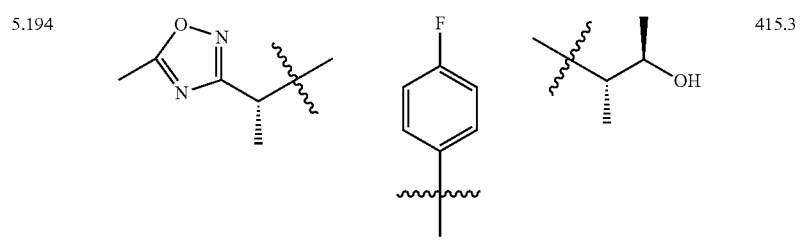 | | | 415.3 |
| 5.195 | 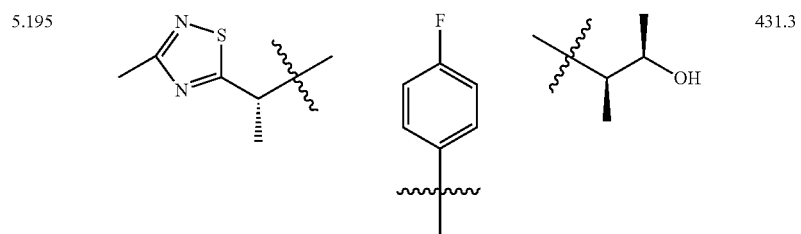 | | | 431.3 |
| 5.196 | 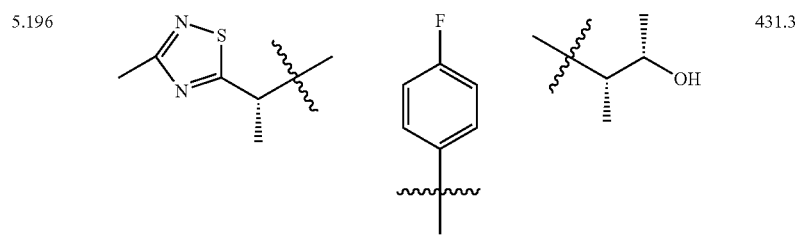 | | | 431.3 |

TABLE 5-continued
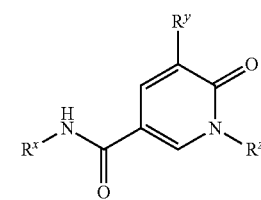
| Example | R<sup>x</sup> | R<sup>y</sup> | R<sup>z</sup> | MS (M + 1) |
|---|---|---|---|---|
| 5.197 | | | | 431.3 |
| 5.198 | | | | 431.3 |
| 5.199 | | | | 420.1466 |
| 5.200 | | | | 420.1472 |
| 5.201 | | | | 419.1514 |
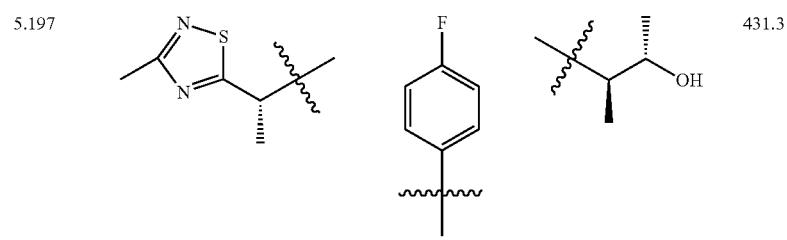
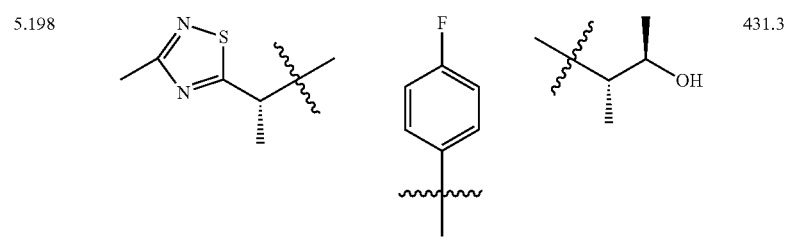
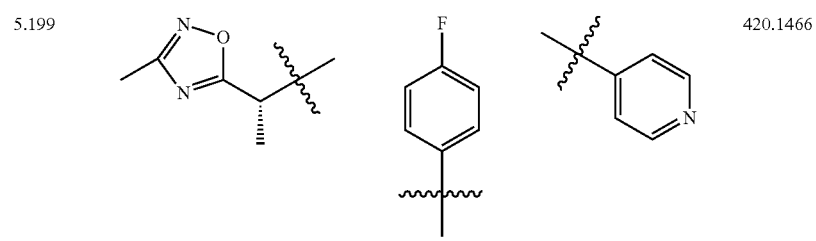
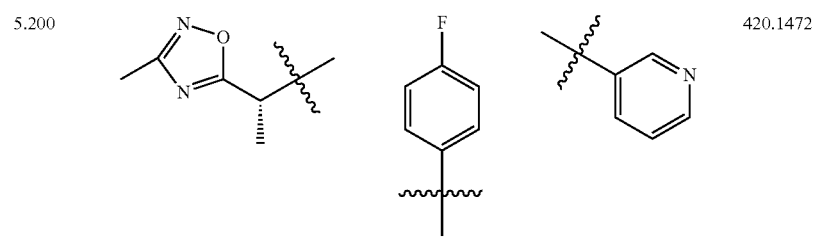
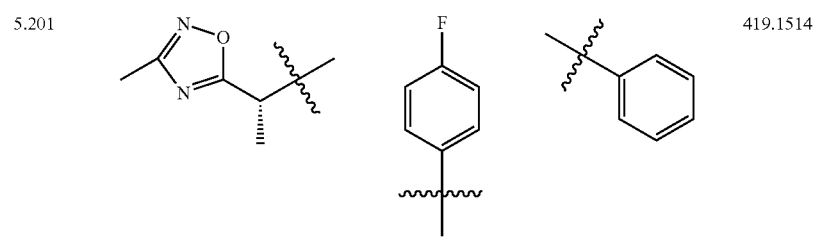

TABLE 5-continued

| Example | R$^x$ | R$^y$ | R$^z$ | MS (M + 1) |
|---|---|---|---|---|
| 5.202 | methyl-1,2,4-thiadiazole with CH(CH₃) linker | 4-F-phenyl | pyridin-3-yl | 436.1238 |
| 5.203 | methyl-1,2,4-thiadiazole with CH(CH₃) linker | 4-F-phenyl | 2-methylthiazol-4-yl | 456.0962 |
| 5.204 | methyl-1,2,4-thiadiazole with CH(CH₃) linker | 4-F-phenyl | 2-cyclopropylthiazol-4-yl | 482.1114 |
| 5.205 | methyl-1,2,4-oxadiazole with CH(CH₃) linker | 4-F-phenyl | 2-methylpyrimidin-5-yl | 435.1577 |
| 5.206 | methyl-1,2,4-thiadiazole with CH(CH₃) linker | 4-F-phenyl | 2-methylpyrimidin-5-yl | 451.1346 |

TABLE 5-continued
| Example | R^x | R^y | R^z | MS (M + 1) |
|---|---|---|---|---|
| 5.207 | 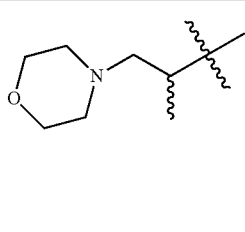 [SMILES: *C(C)CN1CCOCC1] | 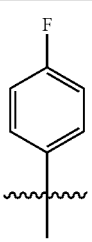 [SMILES: *c1ccc(F)cc1] | 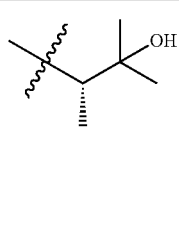 [SMILES: *[C@@H](C)C(C)(C)O] | 446.2441 |
| 5.208 | 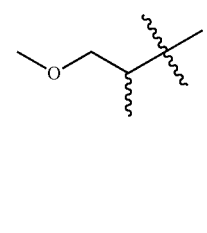 [SMILES: *C(C)COC] | 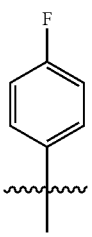 [SMILES: *c1ccc(F)cc1] | 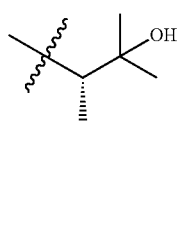 | 391.2024 |
| 5.209 | 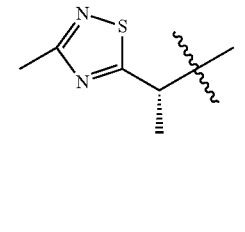 | 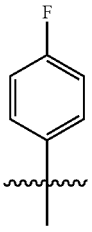 [SMILES: *c1ccc(F)cc1] | 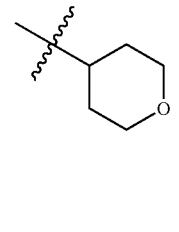 [SMILES: *C1CCOCC1] | 443.1544 |
| 5.210 | 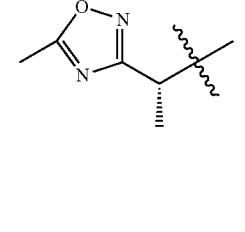 [SMILES: *[C@H](C)c1noc(C)n1] | 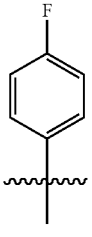 [SMILES: *c1ccc(F)cc1] | 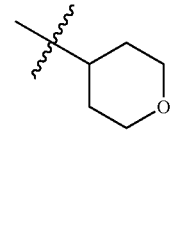 [SMILES: *C1CCOCC1] | 427.1770 |
| 5.211 | 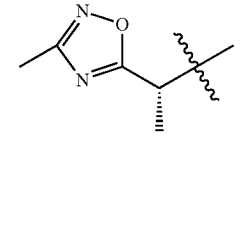 [SMILES: *[C@H](C)c1nc(C)no1] | 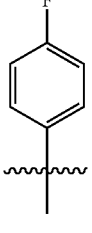 | 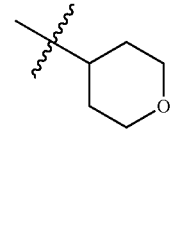 [SMILES: *C1CCOCC1] | 427.1777 |

TABLE 5-continued

| Example | R$^x$ | R$^y$ | R$^z$ | MS (M + 1) |
|---|---|---|---|---|
| 5.212 | 3-methyl-1,2,4-oxadiazol-5-yl with (S)-methyl linker | 4-fluorophenyl | 3,3-dimethyl-2-hydroxy-2-(trifluoromethyl) | 483.1653 |
| 5.213 | 2-(trifluoromethyl)pyrimidin-5-yl with (S)-methyl linker | 4-fluorophenyl | 3-hydroxy-2-methylbutyl | 479.1697 |
| 5.214 | 6-(trifluoromethyl)pyridin-3-yl with (S)-methyl linker | 4-fluorophenyl | 3-hydroxy-2-methylbutyl | 478.1750 |
| 5.215 | 3-methyl-1,2,4-oxadiazol-5-yl with (S)-methyl linker | 4-fluorophenyl | pyrimidin-2-yl with gem-dimethyl linker | 421.1428 |
| 5.216 | 3-methyl-1,2,4-oxadiazol-5-yl with (S)-methyl linker | 4-fluorophenyl | pyrazin-2-yl with gem-dimethyl linker | 421.1423 |

TABLE 5-continued

| Example | R$^x$ | R$^y$ | R$^z$ | MS (M + 1) |
|---------|-------|-------|-------|------------|
| 5.217 | 3-methyl-1,2,4-oxadiazol-5-yl with (S)-methyl | 4-fluorophenyl | (1S,2R)-2-hydroxycyclopentyl (methyl) | 427.1770 |
| 5.218 | 3-methyl-1,2,4-oxadiazol-5-yl with (S)-methyl | 4-fluorophenyl | 2-hydroxycyclopentyl (methyl) | 427.1773 |
| 5.219 | 5-methyl-1,2,4-oxadiazol-3-yl with (S)-methyl | 4-fluorophenyl | 2-hydroxycyclopentyl (methyl) | 427.1771 |
| 5.220 | 3-methyl-1,2,4-thiadiazol-5-yl with (S)-methyl | 4-fluorophenyl | 2-hydroxycyclopentyl (methyl) | 443.1545 |
| 5.221 | 3-methyl-1,2,4-thiadiazol-5-yl with (S)-methyl | 4-fluorophenyl | (1S,2R)-2-hydroxycyclopentyl (methyl) | 443.1559 |

TABLE 5-continued

| Example | R^x | R^y | R^z | MS (M + 1) |
|---|---|---|---|---|
| 5.222 | 5-methyl-1,2,4-oxadiazol-3-yl CH(CH3) | 4-F-phenyl | trans-2-hydroxycyclopentyl | 427.1795 |
| 5.223 | 2-(trifluoromethyl)pyrimidin-5-yl CH(CH3) | 4-F-phenyl | trans-2-hydroxycyclopentyl | 491.1717 |
| 5.224 | 2-(trifluoromethyl)pyrimidin-5-yl CH(CH3) | 4-F-phenyl | pyridin-3-yl | 484.1401 |
| 5.225 | 5-methyl-1,2,4-oxadiazol-3-yl CH(CH3) | 4-F-phenyl | pyridin-3-yl | 420.1466 |
| 5.226 | 3-methyl-1,2,4-oxadiazol-5-yl CH(CH3) | 4-F-phenyl | pyridazin-3-yl | 420.9 |

TABLE 5-continued
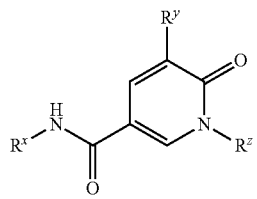
| Example | R$^x$ | R$^y$ | R$^z$ | MS (M + 1) |
|---|---|---|---|---|
| 5.227 | | | | 421.1424 |
| 5.228 | | | | 429.1398 |
| 5.229 | | | | 469.4 |
| 5.230 | | | | 469.4 |
| 5.231 | | | | 469.1507 |

TABLE 5-continued

| Example | R^x | R^y | R^z | MS (M + 1) |
|---|---|---|---|---|
| 5.232 | 3-methyl-1,2,4-oxadiazol-5-yl with (S)-methyl | 4-F-phenyl | CF3/CH(CH3)/OH | 469.1505 |
| 5.233 | 3-methyl-1,2,4-oxadiazol-5-yl with (S)-methyl | 4-F-phenyl | tetrahydropyran-3-yl | 427.4 |
| 5.234 | 5-methyl-1,2,4-oxadiazol-3-yl with (S)-methyl | 4-F-phenyl | tetrahydropyran-3-yl | 427.4 |
| 5.235 | 3-methyl-1,2,4-thiadiazol-5-yl with (S)-methyl | 4-F-phenyl | tetrahydropyran-3-yl | 443.4 |
| 5.236 | 2-(trifluoromethyl)pyrimidin-5-yl with (S)-methyl | 4-F-phenyl | tetrahydropyran-3-yl | 491.4 |

TABLE 5-continued

| Example | R^x | R^y | R^z | MS (M + 1) |
|---|---|---|---|---|
| 5.237 | 2-(trifluoromethyl)pyridin-5-yl, CH(CH3) | 4-fluorophenyl | tetrahydrofuran-3-yl (NH) | 476.4 |
| 5.238 | 3-methyl-1,2,4-thiadiazol-5-yl, CH(CH3) | 4-fluorophenyl | tetrahydrofuran-3-yl (NH) | 429.3 |
| 5.239 | 2-(trifluoromethyl)pyrimidin-5-yl, CH(CH3) | 4-fluorophenyl | tetrahydrofuran-3-yl (NH) | 477.4 |
| 5.240 | 3-methyl-1,2,4-oxadiazol-5-yl, CH(CH3) | 4-fluorophenyl | 2-hydroxycyclopentyl | 427.3 |
| 5.241 | 2-(trifluoromethyl)pyrimidin-5-yl, CH(CH3) | 4-fluorophenyl | 2-hydroxycyclopentyl | 491.3 |

TABLE 5-continued

| Example | R$^x$ | R$^y$ | R$^z$ | MS (M + 1) |
|---|---|---|---|---|
| 5.242 | 3-methyl-1,2,4-thiadiazol-5-yl with (S)-methyl CH linker | 4-fluorophenyl | (1R,2S)-2-hydroxycyclopentyl | 443.3 |
| 5.243 | 5-methyl-1,2,4-oxadiazol-3-yl with (S)-methyl CH linker | 4-fluorophenyl | (1R,2S)-2-hydroxycyclopentyl | 427.3 |
| 5.244 | 3-methyl-1,2,4-oxadiazol-5-yl with (S)-methyl CH linker | 4-fluorophenyl | 2-hydroxycyclopentyl (methyl) | 427.4 |
| 5.245 | 5-methyl-1,2,4-oxadiazol-3-yl with (S)-methyl CH linker | 4-fluorophenyl | 2-hydroxycyclopentyl (methyl) | 427.4 |
| 5.246 | 3-methyl-1,2,4-thiadiazol-5-yl with (S)-methyl CH linker | 4-fluorophenyl | 2-hydroxycyclopentyl (methyl) | 443.4 |

TABLE 5-continued
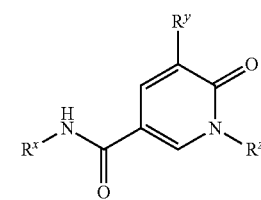
| Example | R$^x$ | R$^y$ | R$^z$ | MS (M + 1) |
|---|---|---|---|---|
| 5.247 | 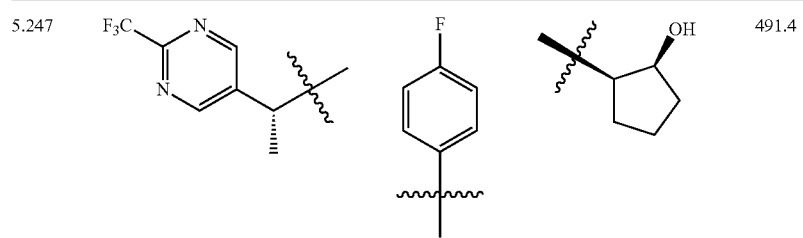 | | | 491.4 |
| 5.248 | 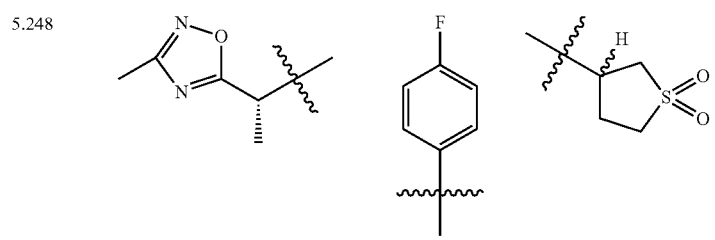 | | | |
| 5.249 | 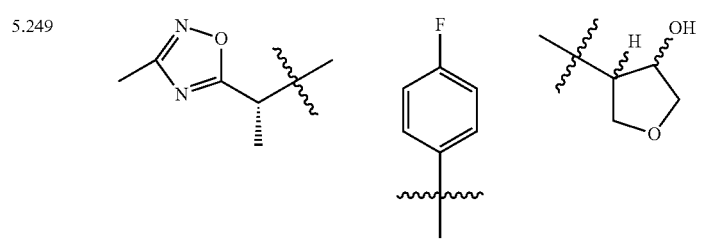 | | | |
| 5.250 | 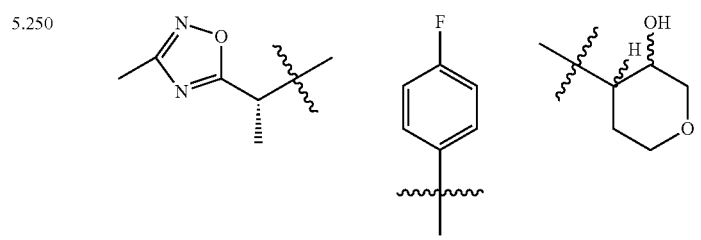 | | | |
| 5.251 | 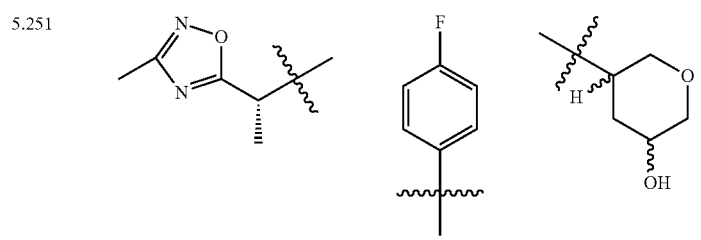 | | | |

TABLE 5-continued

| Example | R$^x$ | R$^y$ | R$^z$ | MS (M + 1) |
|---------|-------|-------|-------|------------|
| 5.252 | methyl-oxadiazolyl | 4-F-phenyl | neopentyl-OH | |
| 5.253 | methyl-oxadiazolyl | 4-F-phenyl | neopentyl-OH | |
| 5.254 | methyl-oxadiazolyl | 4-F-phenyl | neopentyl-OH | | or pharmaceutically acceptable salts and individual enantiomers and diastereomers thereof.

When any variable (e.g. aryl, heterocycle, R$^1$, R$^5$ etc.) occurs more than one time in any constituent, its definition on each occurrence is independent at every other occurrence. Also, combinations of substituents/or variables are permissible only if such combinations result in stable compounds.

When R$^a$ or R$^6$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is C$_2$-C$_6$ alkenyl. Preferred alkynyls are C$_2$-C$_6$ alkynyl.

"Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "C$_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S. heteroaryl groups include, without limitation, thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, aryloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spino-fused to a cycloalkyl, heterocyclyl, or aryl, wherein each of the foregoing is further optionally substituted with one more moieties listed in (a), above.

"Halogen" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of P2X receptor complex modulator sufficient to inhibit or enhance the effect of the P2X receptor complex.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, tissue injury pain, and the like (Dorland's Illustrated Medical Dictionary, 28th Edition, W. B. Saunders Company, Philadelphia, Pa.). The goal of treatment of pain is to reduce the degree or severity of pain perceived by a treatment subject.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin, xvi) sodium channel blockers and xvii) calcitonin gene-related peptide (CGRP) antagonists such as BIBN4096BS (olcegepant), MK-0974 (telcagepant), and $CGRP_{8-37}$ and beta-3 adrenergic receptor agaonists (β3AR) such as CL316243. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, small fiber neuropathy, and diabetic neuropathy. The present compounds and compositions are also useful for the treatment of chronic lower back pain, phantom limb pain, chronic pelvic pain, neuroma pain, complex regional pain syndrome, migraines, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohn's disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders. Thus, another aspect of this invention is the use of the compounds of formula I in the manufacture of a medicament to treat pain and other diseases associated with pain.

Compounds of Formula I also may be used alone or in combination with other drugs in the treatment/prevention/suppression or amelioration of the diseases, conditions, or disorders such as overactive bladder, urinary incontinence, urge urinary incontinence, and urinary urgency.

In addition to primates, such as humans, a variety of other mammals can be treated according to the method of the present invention. For instance, mammals including, but not limited to, cows, sheep, goats, horses, dogs, cats guinea pigs, or other bovine, ovine, equine, canine, feline, rodent such as mouse, species can be treated. However, the method can also be practiced in other species, such as avian species (e.g., chickens).

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-}HT_{1A}$ agonists or antagonists, especially $5\text{-}HT_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with calcium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are advantageous oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet advantageously contains from about 0.1 mg to about 500 mg of the active ingredient and each cachet or capsule advantageously containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

Further, as described above, the instant compounds can be utilized in combination with one or more therapeutically active compounds. In particular, the inventive compounds can be advantageously used in combination with i) opiate agonists or antagonists, ii) other calcium channel antagonists, iii) 5HT receptor agonists or antagonists, including 5-$HT_{1A}$ agonists or antagonists, and 5-$HT_{1A}$ partial agonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, xiv) norepinephrine reuptake inhibitors, xv) monoamine oxidase inhibitors (MAOIs), xvi) reversible inhibitors of monoamine oxidase (RIMAs), xvii) alpha-adrenoreceptor antagonists, xviii) atypical anti-depressants, xix) benzodiazepines, xx) corticotropin releasing factor (CRF) antagonists, xxi) neurontin (gabapentin) and xxii) pregabalin.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, CAMP (cyclic adenosine-3',5'-monophosphate), DAST ((diethylamino)sulfur trifluoride), DBU (1,8-diazabicyclo[5.4.0]undec-7-ene), DIBAL (diisobutylaluminum hydride), DIEA (diisopropylethyl amine), DMAP (4-(dimethylamino)pyridine), DMF (N,N-dimethylformamide), DPPF (1,1'-bisdiphenylphosphino ferrocene), EDC (1-(3-dimethylaminopropyl)-3-ethylcarbodiimide hydrochloride), Et$_3$N (triethylamine), GST (glutathione transferase), HOBt (1-hydroxybenzotriazole), LAH (lithium aluminum hydride), Ms (methanesulfonyl; mesyl; or SO$_2$Me), MsO (methanesulfonate or mesylate), MCPBA (meta-chloro perbenzoic acid), NaHMDS (sodium hexamethyldisilazane), NBS (N-bromosuccinimide), NCS(N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or SO$_2$NH$_2$), SPA (scintillation proximity assay), Th (2- or 3-thienyl), TFA (trifluoroacetic acid), THF (Tetrahydrofuran), Thi (Thiophenediyl), TLC (thin layer chromatography), TMEDA (N,N,N',N'-tetramethylethylenediamine), TMSI (trimethylsilyl iodide), Tr or trityl (N-triphenylmethyl), C$_3$H$_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the procedures provided in the Examples. The following Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive, Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the examples below can be further manipulated, when appropriate, using the standard functional group transformation techniques available to those skilled in the art, to provide desired compounds described in this invention.

It is also understood that compounds of this invention contain one or more stereocenters that may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Several methods for preparing the compounds of this invention are illustrated in the following Schemes and Examples. Starting materials are made according to procedures known in the art or as illustrated herein.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

palladium catalysis with either aryl or heteroaryl boronic acids or esters to give mono-coupled products 1.2. N-arylation of substituted piperidines, morpholines, and piperazines yields amino pyridines 1.3. Ester hydrolysis and amide bond formation using EDC gives final targets 1.4.

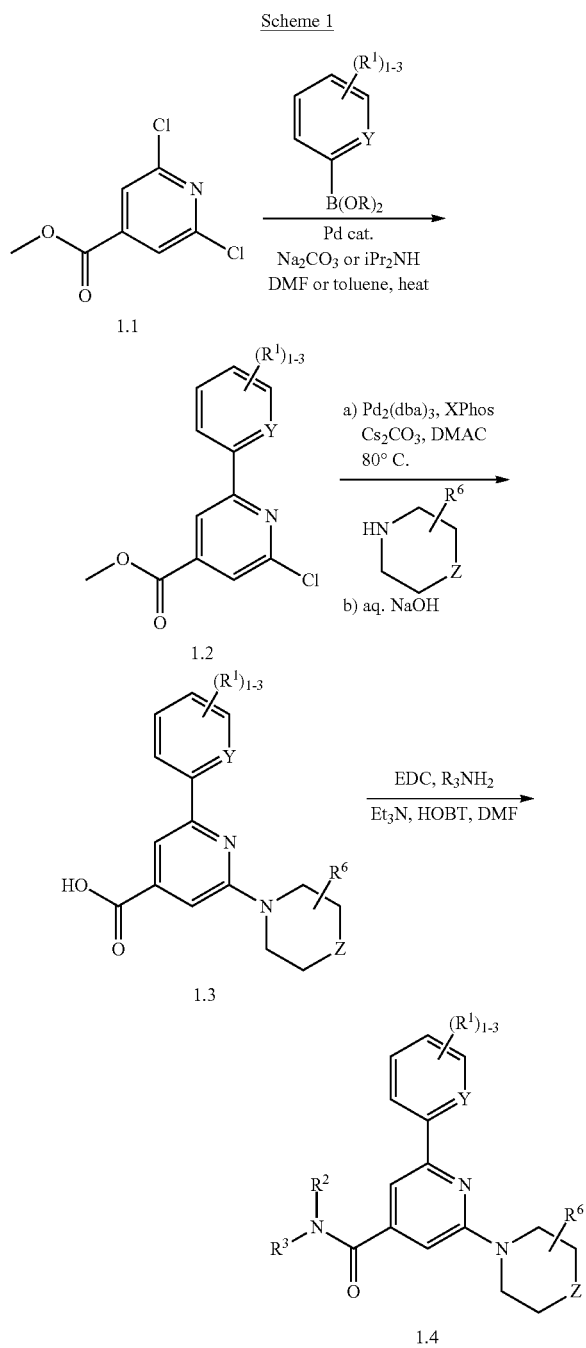

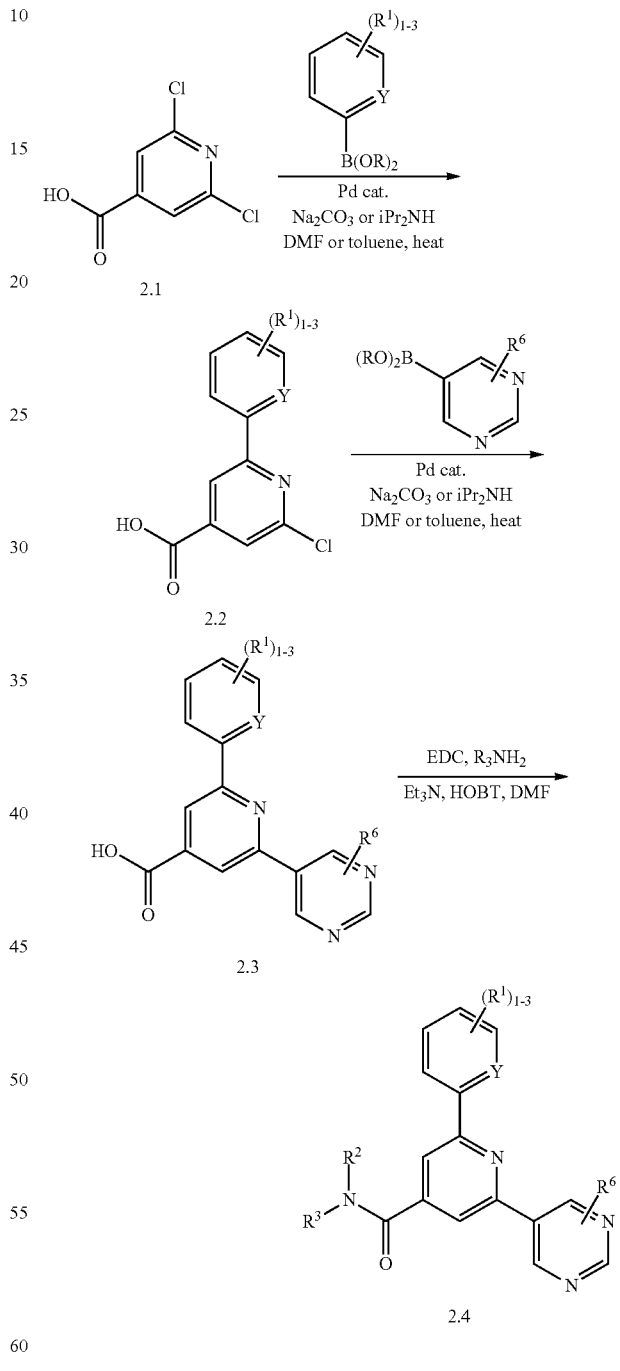

The synthesis of 2-amino pyridine analogs is shown in Scheme 1. Dichloropyridine 1.1 can be cross-coupled under Biaryl substituted pyridines are prepared according to Scheme 2. Palladium-catalyzed cross couplings can be performed on pyridine carboxylic acid 2.1. A second cross coupling is next carried out on various aryl or heteroaryl boronic acids or esters to give triaryl intermediates 2.3. Amide bond formation then yields the final targets 2.4.

Scheme 3

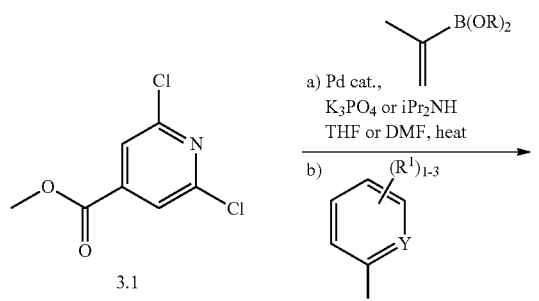

Scheme 4

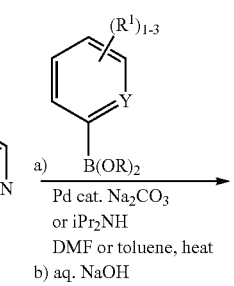

Tertiary hydroxyl analogs are prepared as shown in Scheme 3. Suzuki coupling of dichloropyridine 3.1 with isopropenyl boronate ester followed by sequential addition of a substituted aryl or heteroaryl boronic acid or ester yields the disubstituted pyridine 3.2. Oxidation with catalytic cobalt tetraphenyl porphorin affords the tertiary alcohol derivative which is then hydrolyzed to acid 3.3. Amide bond formation gives final targets 3.4.

Pyridine N-oxides can be prepared according to Scheme 4, Bromopyridine 4.1 can undergo palladium-catalyzed Suzuki cross coupling to a variety of aryl or heteroaryl boronic acids or esters. Subsequent hydrolysis furnishes acid 4.2. Oxidation with MCPBA affords the corresponding pyridine N-oxides 4.3, and amide bond formation using EDC provides amides 4.4.

Scheme 5

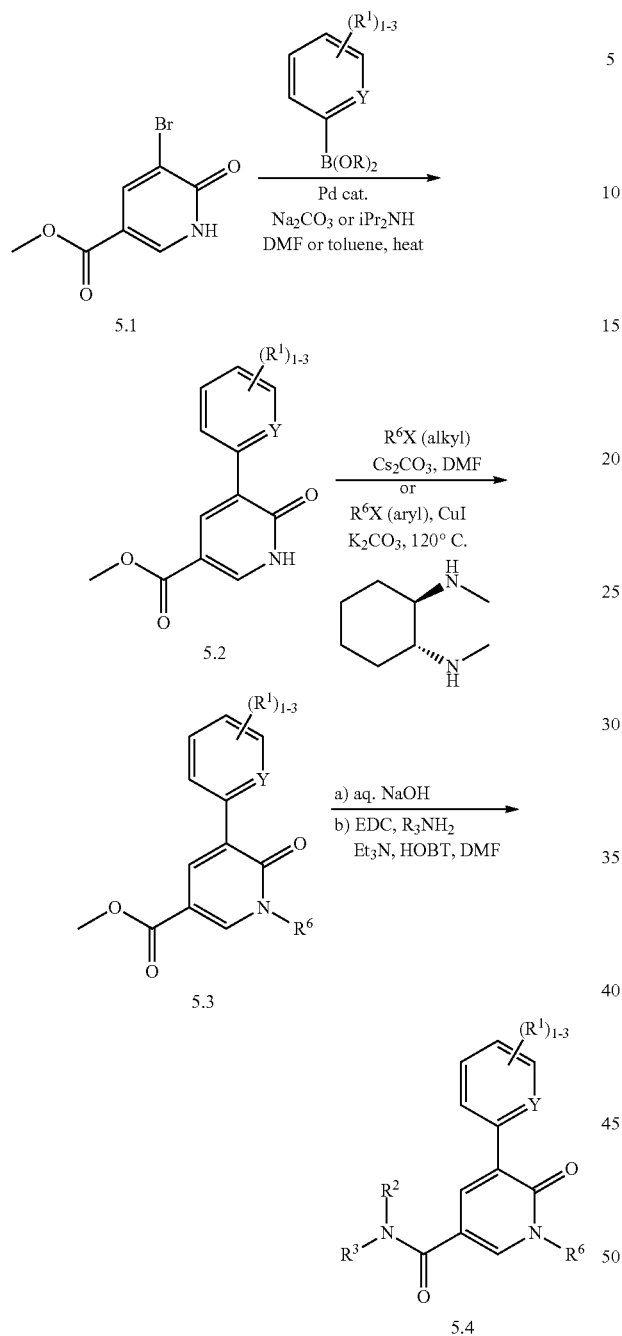

5.1

5.2

5.3

5.4

Substituted pyridinones are prepared according to Scheme 5. Bromopyridinone 5.1 can undergo Suzuki coupling with a variety of aryl or heteroaryl boronic acids or esters to afford intermediate 5.2. N-alkylation can be accomplished using cesium carbonate and an appropriate alkyl halide or tosylate. In some cases a significant amount of o-alkylation is observed. N-arylation is effected using copper(I) iodide with a trans 1,2-cyclohexyl diamine ligand. Hydrolysis and amide bond formation yields final targets 5.4.

Scheme 6

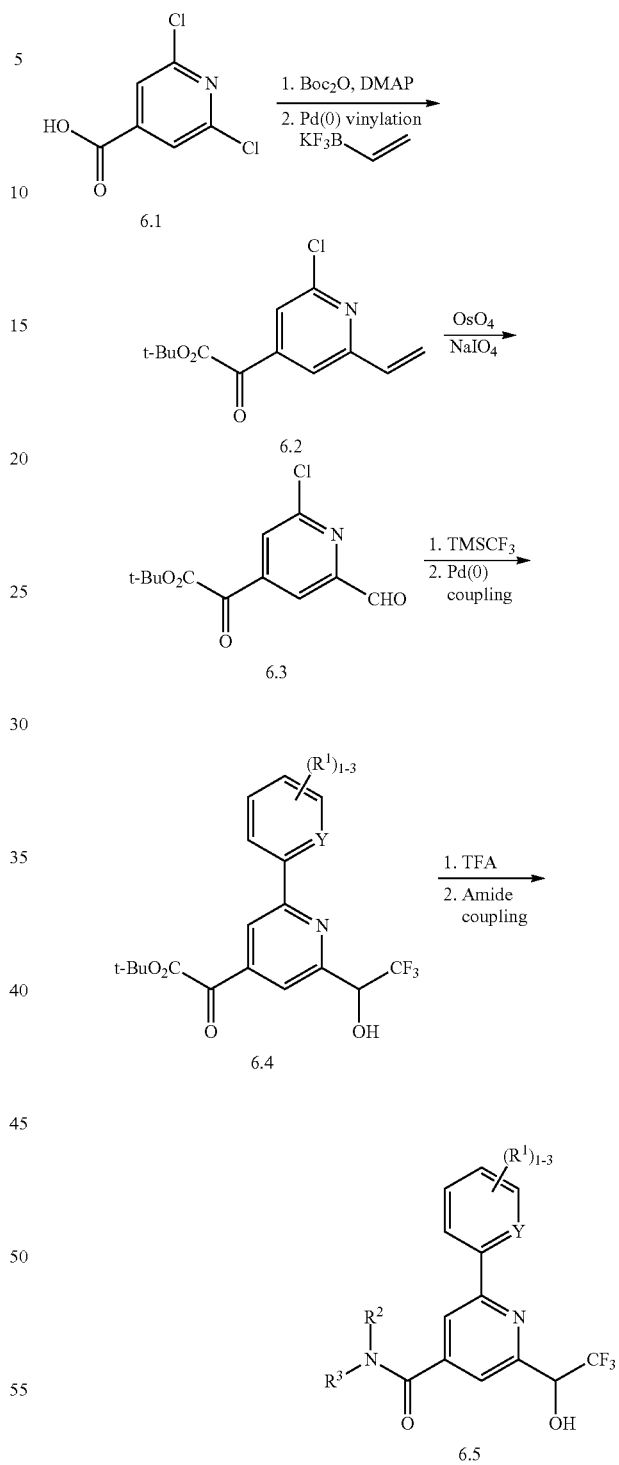

6.1

6.2

6.3

6.4

6.5

Scheme 6 depicts the general synthetic route to prepare compounds of type 6.5. Dichloropyridine 6.1 is protected using Boc$_2$O and subsequent vinyllation gives intermediate 6.2. Oxidation, incorporation of trifluoromethyl group and Suzuki cross-coupling gives intermediates of type 6.4. Ester deprotection and final amide coupling gives examples of type 6.5.

Scheme 7

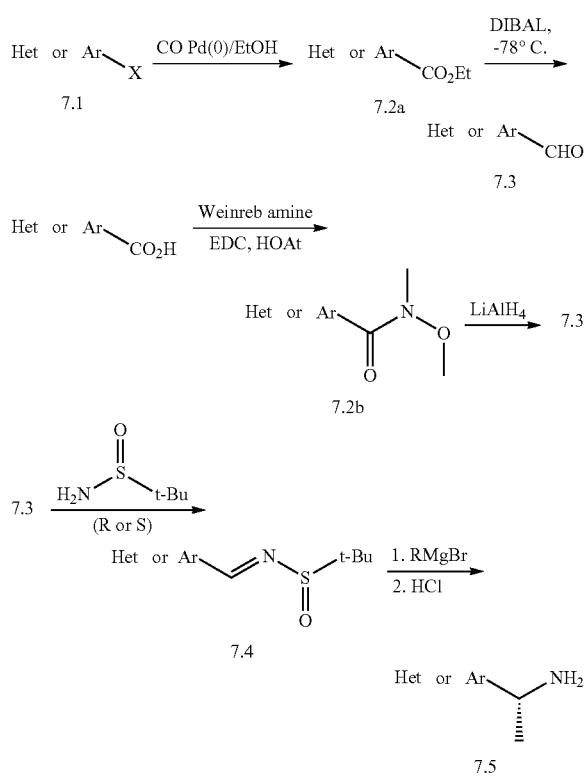

Amine intermediates of type 7.5 can be prepared from one of several intermediates as shown in Scheme 7. This method utilizes diastereoselective Ellman sulfinimine addition chemistry to generate a pair of diastereomeric sulfinamides. The diastereomers are separated by silica chromatography prior to HCl deprotection to give 7.5. Depending on the substrate either the R or S Ellman reagent is utilized to favor the desired alpha methyl amino compound with the preferred stereo configuration shown.

INTERMEDIATES AND EXAMPLES

The following examples are provided so that the invention might be more fully understood. These examples are illustrative only and should not be construed as limiting the invention in any way.

Intermediate 1

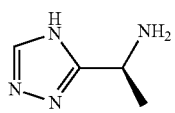

(1S)-1-(4H-1,2,4-Triazol-3-yl)ethanamine

Step A: Benzyl [(1S)-2-amino-1-methyl-2-thioxoethyl]carbamate

To a solution of [(1S)-2-amino-1-methyl-2-oxoethyl]carbamate (15.0 g, 67.5 mmol) in dichloromethane (337 mL) was added 2,4-bis-(4-methoxyphenyl)-1,3-dithia-2,4-diphosphetane 2,4-disulfide (15.01 g, 37.1 mmol) and the mixture was heated to 55° C. After 1.5 h, the reaction was allowed to cool to ambient temperature and concentrated. Recrystallization from dichloromethane gave the title compound (13.4 g). MS 239.1 (M+1).

Step B: Benzyl [(1S)-1-(4H-1,2,4-triazol-3-yl)ethyl]carbamate

To a solution of benzyl[(1S)-2-amino-1-methyl-2-thioxoethyl]carbamate (13.4 g, 56.2 mmol) in ethanol (1.125 L) was added formic acid hydrazide (20.26 g, 337 mmol) and mercury(II) chloride (19.85 g, 73.1 mmol). After 1 h the reaction was filtered and concentrated. Saturated aqueous sodium carbonate and ethyl acetate were added. The organic layer was isolated and the aqueous layer was extracted with ethyl acetate (2×). The combined organic extracts were washed with brine, dried over magnesium sulfate, filtered, and concentrated. A solution of the resulting residue in ethanol (1.125 L) was heated to 80° C. After 16 h, the reaction was concentrated. Purification by silica gel chromatography (100% dichloromethane→90% dichloromethane/methanol with 1% ammonium hydroxide) gave the title compound (8.7 g). MS 247.1 (M+1).

Step C: (1S)-1-(4H-1,2,4-Triazol-3-yl)ethanamine

To a solution of benzyl[(1S)-1-(4H-1,2,4-triazol-3-yl)ethyl]carbamate (8.6 g, 34.9 mmol) in ethanol (140 mL) was added 4 M hydrochloric acid in 1,4-dioxane (43.7 mL, 175 mmol) and 10% palladium on carbon (1,858 g, 1.746 mmol) and the mixture was pressurized to 47 psi under hydrogen. After 4 h, the reaction was depressurized and filtered. Concentration gave the title compound as a hydrochloride salt (6.6 g). MS 113.0 (M+1). $^1$H NMR (500 MHz, CD$_3$OD): δ 8.82 (s, 1H); 4.67 (q, J=6.9 Hz, 1H); 1.70 (dd, J=6.9, 1.0 Hz, 3H).

Intermediate 2

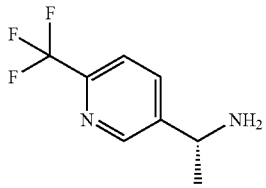

(1R)-1-[6-(Trifluoromethyl)pyridin-3-yl]etanamine

Step A: 2-methyl-N-{(1E)-[6-(trifluoromethyl)-3-pyridinyl]methylene}-2-propanesulfinamide To a solution of 6-(trifluoromethyl)nicotinaldehyde (45.0 g, 257 mmol) in dichloroethane (640 mL) were added (S)-(−)-2-methyl-2-propanesulfinamide (34.3 g, 283 mmol) and anhydrous copper(II) sulfate (82 g, 514 mmol). The mixture was stirred at 50° C. After 48 h, the mixture cooled to ambient temperature. The reaction mixture was filtered through Celite. The filtered cake was washed with dichloromethane and the filtrate was concentrated to give the title compound (76.8 g). MS 223.1 (M-tert-butyl+1)

Step B: 2-Methyl-N-{(1R)-1-[6-(trifluoromethyl)-3-pyridinyl]ethyl}-2-propanesulfinamide To a solution of 2-methyl-N-{(1E)-[6-(trifluoromethyl)-3-pyridinyl]methylene}-2-propanesulfinamide (76.8 g, 276 mmol) in dichloromethane (920 mL) at −45° C. was added methylmagnesium bromide (3.0 M in THF; 184 mL, 552 mmol). The mixture was stirred at −45° C. for 4 h. The reaction mixture was warmed to −20° C. Additional methylmagnesium bromide (3.0 M in THF; 276 mL, 828 mmol) was added at −20° C. The reaction mixture was warmed to 0° C. and was quenched with saturated aqueous ammonium chloride (300 mL). The mixture was allowed to warm to ambient temperature. The organic layer was separated and the aqueous layer was extracted with dichloromethane (3×). The combined organic extracts were washed with brine, dried over magnesium sulfate, filtered and concentrated. The concentrate was recrystallized using ethyl alcohol (500 mL). Then white solid was filtered and dried under reduced pressure (41.6 g). MS 295.0 (M+1).

Step C: (1R)-1-[6-(Trifluoromethyl)-3-pyridinyl]ethanamine

To a solution of 2-methyl-N-{(1R)-1-[6-(trifluoromethyl)-3-pyridinyl]ethyl}-2-propanesulfinamide (41.6 g, 141 mmol) in methyl alcohol (470 mL) at 0° C. was added hydrogen chloride (4.0 M in dioxane; 106 mL, 424 mmol). After 30 min, the mixture was concentrated to dryness. The residue was recrystallized using ethyl alcohol (15 mL) and ether (40 mL). The white solid was filtered and dried under reduced pressure to give the hydrochloride salt of the title compound (26.3 g). MS 191.2 (M+1). $^1$H NMR (500 MHz, CD$_3$OD): δ 8.83 (d, J=2.2 Hz, 1H); 8.17 (d, J=8.2 Hz, 1H); 7.93 (d, J=8.2 Hz, 1H); 4.69 (q, J=6.9 Hz, 1H); 1.70 (d, J=6.9 Hz, 3H).

Intermediate 3

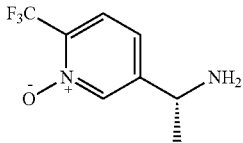

(1R)-1-[1-Oxido-6-(trifluoromethyl)-3-pyridinyl]ethanamine

Step A: tert-Butyl {(1R)-1-[6-(trifluoromethyl)-3-pyridinyl]ethyl}carbamate

To a solution of (1R)-1-[6-(trifluoromethyl)pyridin-3-yl]ethanamine hydrochloride salt (0.554 g, 0.21 mmol) in dichloromethane (7.0 mL) were added di-tert-butyl dicarbonate (0.506 g, 2.32 mmol) and triethylamine (0.969 mL, 6.95 mmol). The reaction mixture was stirred at ambient temperature for 4 h. Saturated aqueous ammonium chloride was added. The mixture was extracted with dichloromethane (3×). The combined organics extracts were washed with brine, dried over magnesium sulfate, filtered and concentrated to give the title compound which was used directly in Step 13 (0.626 g).

Step B: tert-Butyl {(1R)-1-[1-oxido-6-(trifluoromethyl)-3-pyridinyl]ethyl}carbamate To a solution of tert-butyl {(1R)-1-[6-(trifluoromethyl)-3-pyridinyl]ethyl}carbamate (0.626 g, 2.157 mmol) in chloroform (10.0 mL) were added 2,6-di-tert-butyl-4-methylphenol (24 mg, 0.108 mmol) and 3-chloroperbenzoic acid (0.665 g, 2.70 mmol). The reaction mixture was stirred at 50° C. for 48 h. The reaction mixture was cooled to ambient temperature. Saturated aqueous sodium thiosulfate and saturated aqueous sodium bicarbonate were added. The mixture was extracted with dichloromethane (3×). The combined organics extracts were washed with brine, dried over magnesium sulfate, filtered and concentrated. Purification by silica gel chromatography (75% hexanes/ethyl acetate→100% ethyl acetate) gave the title compound (140 mg). MS 307.0 (M+1).

Step C: (1R)-1-[1-Oxido-6-(trifluoromethyl)-3-pyridinyl]ethanamine hydrochloride To a solution of tert-butyl {(1R)-1-[1-oxido-6-(trifluoromethyl)-3-pyridinyl]ethyl}carbamate (140 mg, 0.457 mmol) in dioxane (2 mL) was added hydrogen chloride (4.0 M in dioxane; 0.343 mL, 1.371 mmol). The reaction mixture was stirred for 4 h. The reaction mixture was concentrated to dryness to give the hydrochloride salt of the title compound (118 mg). MS 207.1 (M+1).

Intermediate 4

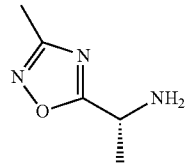

(1R)-1-(3-Methyl-1,2,4-oxadiazol-5-yl)ethanamine

Step A: tert-Butyl [(1R)-1-(3-methyl-1,2,4-oxadiazol-5-yl)ethyl]carbamate

To a solution of N-(tert-butoxycarbonyl)-D-alanine (20 g, 106 mmol), acetamide oxime (17.3 g, 234 mmol) in 120 mL of 1,4-dioxane and 30 mL of N,N-dimethylformamide were added EDC (44.8 g, 234 mmol). The mixture was heated at 60° C. for 4 h then at 100° C. for 16 h. After cooling to ambient temperature, 300 mL of ethyl acetate was added. The mixture was washed with aqueous saturated sodium bicarbonate (2×). The combined organic extracts were dried over magnesium sulfate, filtered and concentrated. The residue was purified by silica gel chromatography (100% dichloromethane→90% dichloromethane/methanol) to give pure tert-butyl [(1R)-1-(3-methyl-1,2,4-oxadiazol-5-yl)ethyl]carbamate (6.0 g). MS 172.1 ((M-t-butyl+H)+1).

Step B: (1R)-1-(3-Methyl-1,2,4-oxadiazol-5-yl)ethanamine

To a solution of tert-butyl [(1R)-1-(3-methyl-1,2,4-oxadiazol-5-yl)ethyl]carbamate (6.0 g, 26.4 mmol) in dioxane (40 mL) was added 4 M hydrochloric acid in dioxane (30 mL). The reaction mixture was stirred for 16 h. The solution was concentrated and dried by vacuum to give hydrochloride salt of (1R)-1-(3-methyl-1,2,4-oxadiazol-5-yl)ethanamine (5.1 g). ¹H NMR (500 MHz, CD₃OD): δ 490-4.83 (m, 1H); 2.41 (s, 3H); 1.72 (d, J=7.0 Hz, 3H). MS 128.2 (M+1).

Intermediate 5

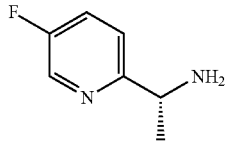

(1R)-1-(5-Fluoropyridin-2-yl)ethanamine

Step A: Ethyl 5-fluoropyridine-2-carboxylate

To a degassed solution of ethyl alcohol (400 mL) in a Parr steel bomb was added sodium acetate (43.3 g, 528 mmol), 2-bromo-5-fluoropyridine (20 g, 114 mmol), 1,1'-bis(diphenylphosphino)ferrocene (2.27 g, 4.09 mmol) and palladium acetate (204 mg, 0.91 mmol). The vessel was put under nitrogen and sealed with Parr top. The atmosphere was displaced with carbon monoxide gas and the pressure was adjusted to 300 psi. The mixture was heated to 90° C. After 3 h, the pressure dropped to below 100 psi. The vessel was cooled to ambient temperature and the reaction was repressurized with carbon monoxide to 300 psi. The vessel was heated to 90° C. for an additional 4 h. The vessel was cooled to ambient temperature and the remaining carbon monoxide was vented. The mixture was concentrated to half of the volume. Ethyl acetate (500 mL) and water (300 mL) were added. The organic layer was isolated and the aqueous layer was extracted with ethyl acetate (2×). The combined organic extracts were washed with brine, dried over sodium sulfate, filtered and concentrated. Purification by silica gel chromatography (100% hexanes→70% hexanes/ethyl acetate) gave the title compound. MS 170.0 (M+1).

Step B: 5-Fluoropyridine-2-carbaldehyde

To a solution of ethyl 5-fluoropyridine-2-carboxylate (25 g, 148 mmol) in tetrahydrofuran (250 mL) at −78° C. was added dropwise diisobutylaluminum hydride (1.0 M in hexanes; 296 mL, 296 mmol). After 1 h, the reaction was quenched with ethyl alcohol (10 mL). Saturated aqueous sodium potassium tartrate tetrahydrate (1.3 L) was added and the aqueous layer was extracted with ethyl acetate (2×). The combined organic extracts were washed with brine, dried over sodium sulfate, filtered. The solution mixture (1.4 L) was carried onto the next step without concentration. MS 125.9 (M+1).

Step C: N-[(1E)-(5-Fluoropyridin-2-yl)methylene]-2-methylpropane-2-sulfinamide

To a solution of 5-fluoropyridine-2-carbaldehyde (18.49 g, 148 mmol) in ethyl acetate (850 mL), THF (250 mL) and hexanes (300 mL) were added (R)-(+)-2-methyl-2-propanesulfinamide (19.71 g, 163 mmol) and anhydrous copper(II) sulfate (59.0 g, 370 mmol). The mixture was stirred at ambient temperature. After 18 h, the mixture was filtered through Celite. The filtered cake was washed with ethyl acetate and the filtrate was concentrated. Purification by silica gel chromatography (100% dichloromethane→98% dichloromethane/methanol) gave the title compound.

Step D: N-[(1R)-1-(5-Fluoropyridin-2-yl)ethyl]-2-methylpropane-2-sulfinamide

To a solution of N-[(1E)-(5-fluoropyridin-2-yl)methylene]-2-methylpropane-2-sulfinamide (52.12 g, 228 mmol) in dichloromethane (1000 mL) at −78° C. was added methylmagnesium bromide (3.0 M in THF; 198 mL, 594 mmol). The mixture was allowed to warm to ambient temperature. After 30 min, the mixture was cooled down to −78° C. and was quenched with saturated aqueous ammonium chloride (100 mL). The mixture was allowed to warm to ambient temperature. The organic layer was separated and the aqueous layer was extracted with dichloromethane (3×). The combined organic extracts were washed with brine, dried over sodium sulfate, filtered and concentrated. Purification by silica gel chromatography (100% ethyl acetate) gave the title compound. MS 245 (M+1).

Step E: (1R)-1-(5-Fluoropyridin-2-yl)ethanamine

To a solution of N-[(1R)-1-(5-fluoropyridin-2-yl)ethyl]-2-methylpropane-2-sulfinamide (34.3 g, 140 mmol) in methyl alcohol (700 mL) at 0° C. was added hydrogen chloride (4.0 M in dioxane; 105 mL, 421 mmol). After 30 min, the mixture was concentrated to dryness. The residue was recrytalized using ethyl alcohol (15 mL) and ether (40 mL). The white solid was filtered and dried under reduced pressure to give the hydrochloride salt of the title compound. MS 141.1 (M+1).

Intermediate 6

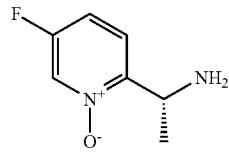

(1R)-1-(5-Fluoro-1-oxidopyrindin-2-yl)ethanamine

Step A: tert-Butyl [(1R)-1-(5-fluoropyridin-2-yl)ethyl]carbamate

To a solution of the toluene sulfonic acid salt of (1R)-1-(5-fluoropyridin-2-yl)ethanamine (7.5 g, 24.0 mmol) in dichloromethane (96 mL) at 0° C. was added triethylamine (7.03 mL, 50.0 mmol) and di-tert-butyl dicarbonate (6.13 mL, 26.4 mmol). The mixture was allowed to warm to ambient temperature. After 16 hours, saturated aqueous sodium bicarbonate was added. The organic layer was isolated and the aqueous layer was extracted with dichloromethane (2×). The combined organic extracts were washed with brine, dried over magnesium sulfate, and filtered. Concentration gave the title compound (7.72 g). MS 241.1 (M+1).

Step B: tert-Butyl [(1R)-1-(5-fluoro-1-oxidopyridin-2-yl)ethyl]carbamate

To a solution of tert-butyl [(1R)-1-(5-fluoropyridin-2-yl)ethyl]carbamate (5.77 g, 24.0 mmol) in dichloromethane (96 mL) was added 3-chloroperbenzoic acid (6.51 g, 26.4 mmol). After 4.5 h, excess 3-chloroperbenzoic acid (0.59 g, 2.6 mmol) was added. After 72 h, saturated aqueous sodium sulfite was added. After 1 h, saturated aqueous sodium bicarbonate was added. The organic layer was isolated and the aqueous layer was extracted with dichloromethane (2×). The combined organic extracts were washed with brine, dried over magnesium sulfate, filtered, and concentrated. Purification by silica gel chromatography (100% dichloromethane→90% dichloromethane/methanol with 1% ammonium hydroxide) gave the title compound (5.45 g). MS 257.1 (M+1).

Step C: (1R)-1-(5-Fluoro-1-oxidopyrindin-2-yl)ethanamine

To a solution of tert-butyl [(1R)-1-(5-fluoro-1-oxidopyridin-2-yl)ethyl]carbamate (1.47 g, 5.74 mmol) in dichloromethane (28.7 mL) was added 4 M hydrochloric acid in 1,4-dioxane (43.0 mL, 172 mmol). After 2 h, concentration gave the title compound as a hydrochloride salt (1.396 g). MS 157.1 (M+1). $^1$H NMR (500 MHz, CD$_3$OD): δ 8.55 (dd, J=4.3, 2.4 Hz, 1H); 7.70 (dd, J=9.0, 6.7 Hz, 1H); 7.52 (ddd, J=9.1, 7.1, 2.4 Hz, 1H); 4.80 (q, J=7.0 Hz, 1H); 1.74 (d, J=7.0 Hz, 3H).

Intermediate 7

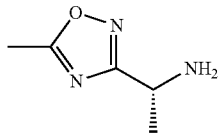

(1R)-1-(5-Methyl-1,2,4-oxadiazol-3-yl)ethanamine

Step A: Benzyl [(1R)-1-cyanoethyl]carbamate

To a solution of benzyl [(1R)-2-amino-1-methyl-2-oxoethyl]carbamate (10 g, 45 mmol) in 50 mL of N,N-dimethylformamide was added 2,4,6-trichloro-1,3,5-triazine (4.15 g, 22.5 mmol). After 2 h, 100 mL of water was added and the mixture was filtered. The solids were washed with 100 mL aqueous sodium bicarbonate (2×) and dried under vacuum to give pure benzyl [(1R)-1-cyanoethyl]carbamate (7.2 g). MS 205.2 ((M+1).

Step B: Benzyl [(1R,2Z)-2-amino-2-(hydroxyimino)-1-methylethyl]carbamate

To a solution of benzyl [(1R)-1-cyanoethyl]carbamate (2.52 g, 12.3 mmol) in ethanol (30 ml) was added hydroxylamine hydrochloride salt (0.90 g, 13.0 mmol) and triethylamine (3.43 ml, 24.6 mmol) and the mixture heated to 75° C. After 16 h, the solution was concentrated and the residue was dissolved in 200 mL of dichloromethane. The mixture was washed with 100 mL of saturated aqueous sodium bicarbonate (2×) and brine (100 mL). The combined organic extracts were dried over sodium sulfate, filtered and concentrated to give benzyl [(1R,2Z)-2-amino-2-(hydroxyimino)-1-methylethyl]carbamate (2.9 g). MS 238.2 (M+1).

Step C: Benzyl [(1R)-1-(5-methyl-1,2,4-oxadiazol-3-yl)ethyl]carbamate

To a solution of benzyl [(1R,2Z)-2-amino-2-(hydroxyimino)-1-methylethyl]carbamate (2.25 g, 9.48 mmol) in dioxane (80 ml) was added 1-acetyl-1H-imidazole (3.13 g, 28.5 mmol) and the mixture heated to 90° C. After 16 h, the solution was concentrated and the residue was dissolved in 200 mL of dichloromethane. The mixture was washed with 100 mL of aqueous saturated sodium bicarbonate (2×) and brine (100 mL). The organic layer was dried over sodium sulfate, filtered and concentrated. The residue was purified by silica gel chromatography (100% dichloromethane→95% dichloromethane/methanol) to give the title compound (1.1 g). MS 262.1 (M+1).

Step D: (1R)-1-(5-Methyl-1,2,4-oxadiazol-3-yl)ethanamine

To a solution of benzyl [(1R)-1-(5-methyl-1,2,4-oxadiazol-3-yl)ethyl]carbamate (1.10 g, 4.21 mmol) in dichloromethane (40 mL) was added 1 M boron trichloride solution in dichloromethane (21.1 mL, 21.1 mmol) at 0° C. The reaction mixture was allowed to warm from 0° C. to 20° C. over 4 h. The solution was quenched by 5 ml of methanol at 0° C. After warming to ambient temperature, the mixture was concentrated and the residue was washed with 100 mL of diethyl ether (2×) to give the hydrochloride salt of (1R)-1-(5-methyl-1,2,4-oxadiazol-3-yl)ethanamine was obtained as solid (0.84 g). $^1$H NMR (500 MHz, CD$_3$OD): δ 4.70-4.61 (m, 1H); 2.63 (s, 3H); 1.67 (d, J=6.9 Hz, 3H).

Intermediate 8

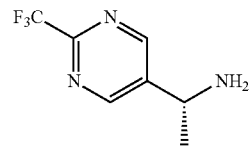

(1R)-1-[2-(Trifluoromethyl)pyrimidin-5-yl]ethanamine

Step A: Ethyl 2-(trifluoromethyl)pyrimidine-5-carboxylate

To a solution of ethyl 4-chloro-2-(trifluoromethyl)pyrimidine-5-carboxylate (30.2 g, 119.0 mmol) in ethanol (594 mL) under nitrogen were added palladium (10% on carbon, 50% water wet; 2.58 g, 1.21 mmol) and diisopropylethylamine (50.0 mL, 286.0 mmol). The mixture stirred under hydrogen (1 atm). After 6 h, the mixture was filtered with Celite. The filtrate was concentrated and ethyl acetate was added. The mixture was washed with sat. NaHCO$_3$ (2×), brine, dried over Na$_2$SO$_4$, filtered and concentrated to give the title compound (25.6 g). MS 221.1 (M+1).

Step B: 2-(Trifluoromethyl)pyrimidine-5-carbaldehyde

To a solution of ethyl 2-(trifluoromethyl)pyrimidine-5-carboxylate (25.5 g, 116.0 mmol) in dichloromethane (580 mL) at −78° C. was slowly added DIBAL-H (1.0 M; 130.0 mL, 130.0 mmol). The mixture was stirred at −78° C. After 2 h, the mixture was quenched via slow addition of HCl (2.0 M in water). The mixture was allowed to warm to ambient temperature. The mixture was extracted with diethyl ether (3×). The combined organic extracts was dried over Na$_2$SO$_4$, filtered and concentrated to give the title compound (28.2 g).

Step C: 2-Methyl-N-{(1Z)-[2-(trifluoromethyl)pyrimidin-5-yl]methylene}propane-2-sulfinamide To a solution of 2-(trifluoromethyl)pyrimidine-5-carbaldehyde (27.2 g, 99 mmol) in dichloroethane (250 mL) was added (R)-(+)-2-methyl-2-propanesulfinamide (13.3 g, 109.0 mmol) and copper(II) sulfate (31.5 g, 197.0 mmol). The mixture was heated to 50° C. After 18 h, the mixture was cooled to ambient temperature and filtered through a pad of silica gel. The filtered cake was washed with dichloromethane and the filtrate was concentrated to give the title compound (27.3 g). MS 224 [(M+1)-56].

Step D: 2-Methyl-N-{(1R)-1-[2-(trifluoromethyl)pyrimidin-5-yl]ethyl}propane-2-sulfinamide To a solution of 2-methyl-N-{(1Z)-[2-(trifluoromethyl)pyrimidin-5-yl]methylene}propane-2-sulfinamide (14.3 g, 51.2 mmol) in toluene (260 mL) at −70° C. was added methyllithium (1.6 M; 35.0 mL, 56.0 mmol). The mixture was stirred at −70° C. for 15 min. The mixture was quenched with sat. NH$_4$Cl and the reaction was allowed to warm to ambient temperature. The mixture was extracted with dichloromethane (3×). The combined organic extracts was dried over Na$_2$SO$_4$, filtered and concentrated. Purification by silica gel chromatography (100% hexanes→35% hexanes/ethyl acetate then 100% ethyl acetate→94% ethyl acetate/methanol) gave the title compound (7.23 g). MS 240 [(M+1)-56].

Step E: (1R)-1-[2-(Trifluoromethyl)pyrimidin-5-yl]ethanamine

To a solution of 2-methyl-N-{(1R)-1-[2-(trifluoromethyl)pyrimidin-5-yl]ethyl}propane-2-sulfinamide (7.23 g, 24.5 mmol) in methanol (100 mL) was added HCl (4.0 M in dioxane; 18.5 mL, 74.0 mmol). The mixture was stirred at ambient temperature. After 1 h, the mixture was concentrated to give the title compound (4.6 g).

Example 1.32

2-(2-Fluoro-4-methylphenyl)-6-morpholin-4-yl-N-[(1S)-1-(4H-1,2,4-triazol-3-yl)ethyl]isonicotinamide

Step A: Methyl 2-chloro-6-(2-fluoro-4-methylphenyl)isonicotinate

To a solution of methyl 2,6-dichloroisonicotinate (3.34 g, 16.2 mmol) in toluene (100 mL) were added (2-fluoro-4-methylphenyl)boronic acid (1.4 g, 9.09 mmol), (tetrakistriphenylphosphine)palladium (0) (0.94 g, 0.81 mmol) and sodium carbonate (2.0 M in water; 8.1 g, 16.2 mmol). The mixture was degassed with nitrogen (3×) and heated to 80° C. After 42 h, the mixture was cooled to ambient temperature and saturated NaHCO$_3$ was added. The mixture was extracted with ethyl acetate (3×). The combined organic extracts were washed with brine, dried over sodium sulfate, filtered and concentrated. Purification by reverse phase chromatography (C-18, 85% water/acetonitrile→5% water/acetonitrile with 0.1% trifluoroacetic acid) gave the title compound (1.07 g). MS 280.0 (M+1).

Step B: Methyl 2-(2-fluoro-4-methylphenyl)-6-morpholin-4-ylisonicotinate

To a solution of methyl 2-chloro-6-(2-fluoro-4-methylphenyl)isonicotinate (0.26 g, 0.94 mmol) in DMA (4 mL) were added morpholine (0.10 mL, 1.17 mmol), tris(dibenzylideneacetone)dipalladium(0) (21.4 mg, 0.02 mmol), 2-dicyclohexylphosphino-2',4',6'-triisopropylbiphenyl (33.5 mg, 0.07 mmol) and cesium carbonate (0.46 g, 1.41 mmol). The mixture was heated to 80° C. After 18 h, the mixture was filtered. The filtered cake was washed with methanol. The filtrate was concentrated to remove methanol. The solution in DMA was carried onto the next step.

Step C: 2-(2-Fluoro-4-methylphenyl)-6-morpholin-4-ylisonicotinic acid

To a solution of methyl 2-(2-fluoro-4-methylphenyl)-6-morpholin-4-ylisonicotinate (0.31 g, 0.94 mmol) in DMA (4 mL) was added sodium hydroxide (1.0 M solution in water; 1.87 mL, 1.87 mmol). The mixture was stirred at ambient temperature. After 1 h, HCl (1.0 M in water; 1.87 mL, 1.87 mmol) was added and the mixture was concentrated. Methanol was added and the mixture was filtered and the filtrate was concentrated. The mixture was purified by reverse phase chromatography (C-18, 95% water/acetonitrile→25% water/acetonitrile with 0.1% trifluoroacetic acid). HCl (1.0 M) was added and fractions were concentrated to give the hydrochloride salt of the title compound (129 mg). MS 317.0 (M+1).

Step D: 2-(2-Fluoro-4-methylphenyl)-6-morpholin-4-O—N-[(1S)-1-(4H-1,2,4-triazol-3-yl)ethyl]isonicotinamide To a solution of the hydrochloride salt of 2-(2-fluoro-4-methylphenyl)-6-morpholin-4-ylisonicotinic acid (50 mg, 0.14 mmol) in DMF (1.5 mL) were added hydrochloride salt of (1S)-1-(4H-1,2,4-triazol-3-yl)ethanamine (31.5 mg, 0.17 mmol), EDC (35.3 mg, 0.18 mmol), HOST (21.7 mg, 0.14 mmol) and diisopropylethylamine (99.0 μL, 0.57 mmol). The mixture was stirred at ambient temperature. After 72 h, the mixture was filtered and the filtrate was purified by reverse phase chromatography (C-18, 95% water/acetonitrile→25% water/acetonitrile with 0.1% trifluoroacetic acid). The product was treated with HCl (2.0 M in ether) to give the hydrochloride salt of the title compound (69 mg). HRMS 411.1936

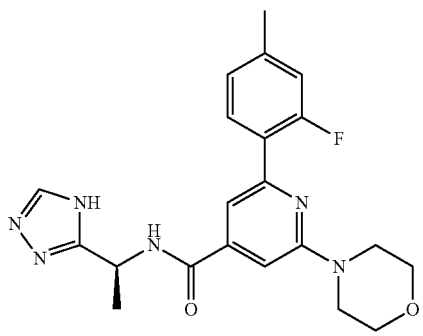 [SMILES: Cc1ccc(-c2cc(C(=O)N[C@@H](C)c3nnc[nH]3)cc(N3CCOCC3)n2)c(F)c1]

(M+1). ¹H NMR δ (ppm)(CH₃OH-d₄): 9.32 (s, 1H), 7.74 (t, J=7.96 Hz, 1H), 7.63 (s, 1H), 7.50 (s, 1H), 7.21 (d, J=7.95 Hz, 1H), 7.16 (d, J=12.16 Hz, 1H), 5.52-5.46 (m, 1H), 3.87 (t, J=4.72 Hz, 4H), 3.77 (t, J=4.67 Hz, 4H), 2.44 (s, 3H), 1.78 (d, J=7.05 Hz, 3H).

Example 1.62

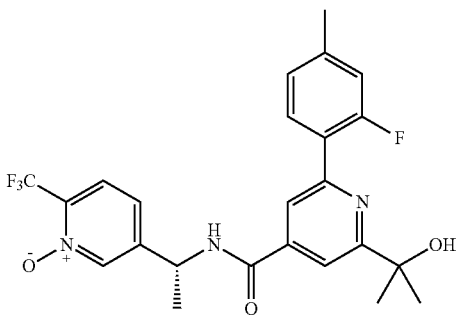

2-(2,4-Difluorophenyl)-6-(1-hydroxy-1-methylethyl)-N-{(1R)-1-[1-oxido-6-(trifluoromethyl)pyridin-3-yl]ethyl}isonicotinamide Step A: Methyl 2-(2,4-difluorophenyl)-6-isopropenylisonicotinate To a degassed solution of methyl 2,6-dichloroisonicotinate (0.1 g, 0.49 mmol), tripotassium phosphate (0.16 g, 0.73 mmol), palladium(II) acetate (8.72 mg, 0.04 mmol) and tris(2-methoxyphenyl)phosphine (27.4 mg, 0.08 mmol) in THF (1 mL) and water (0.25 mL) was added 2-isopropenyl-4,4,5,5-tetramethyl-1,3,2-dioxaborolane (0.11 mL, 0.61 mmol)) The mixture was heated to 65° C. After 4 h, a solution of (2,4-difluorophenyl)boronic acid (0.12 g, 0.73 mmol) in THF (0.5 mL) was added. The mixture was continued to stir at 65° C. After 18 h, the mixture was cooled to ambient temperature. Saturated aqueous NaHCO₃ was added the mixture was extracted with ethyl acetate (3×). The combined organic extracts were washed with brine, dried over magnesium sulfate, filtered and concentrated. Purification by silica gel chromatography (100% hexanes→90% hexanes/ethyl acetate) gave the title compound (144 mg, 80% pure). MS 290.1 (M+1).

Step B: 2-(2,4-Difluorophenyl)-6-(1-hydroxy-1-methylethyl)isonicotinic acid

To a solution of methyl 2-(2,4-difluorophenyl)-6-isopropenylisonicotinate (0.29 g, 1.01 mmol) in methanol (5.1 mL) and DME (5.1 mL) was added cobalt(II)mesotetraphenylporphine (6.8 mg, 10.1 mmol). The mixture was stirred at ambient temperature. After 18 h, tetraethylammonium borohydride (73.5 mg, 0.51 mmol) was added. After 15 min, additional tetraethylammonium borohydride (0.14 g, 1.01 mmol) was added. After 1.5 h, sodium hydroxide (1.0 M in water; 2.03 mL, 2.03 mmol) was added. The mixture was heated to 50° C. After 1 h, HCl (0.17 mL, 2.03 mmol) was added and the mixture was concentrated. Purification by reverse phase chromatography (C-18, 95% water/acetonitrile→25% water/acetonitrile with 0.1% trifluoroacetic acid) gave the title compound (0.22 g). MS 294.1 (M+1).

Step C: 2-(2,4-Difluorophenyl)-6-(1-hydroxy-1-methylethyl)-N-{(1R)-1-[1-oxido-6-(trifluoromethyl)pyridin-3-yl]ethyl}isonicotinamide To a solution of 2-(2,4-difluorophenyl)-6-(1-hydroxy-1-methylethyl)isonicotinic acid (19.5 mg, 0.07 mmol) in DMF (0.67 mL) were added hydrochloride salt of (1R)-1-[1-oxido-6-(trifluoromethyl)pyridin-3-yl]ethanamine (24.2 mg, 0.10 mmol), HATU (0.5 M in DMA; 0.2 mL, 0.10 mmol) and diisopropylethylamine (46.5 uL, 0.27 mmol). The mixture was stirred at ambient temperature. After 30 min, small amount of water and trifluoroacetic acid were added and the mixture was purified by reverse phase chromatography (C-18, 95% water/acetonitrile→5% water/acetonitrile with 0.1% trifluoroacetic acid) gave the title compound (28 mg). HRMS 482.1462 (M+1). ¹H NMR (400 MHz, CDCl₃): δ 8.38 (s, 1H); 8.09-8.01 (m, 1H); 7.94 (s, 1H); 7.73 (s, 1H); 7.67 (d, J=8.3 Hz, 1H); 7.38 (d, J=8.3 Hz, 1H); 7.07-6.98 (m, 1H); 6.99-6.90 (m, 1H); 6.74 (d, J=6.9 Hz, 1H); 5.32-5.25 (m, 1H); 4.38 (s, 1H); 1.67 (d, J=7.1 Hz, 3H); 1.62 (s, 6H).

Example 1.63

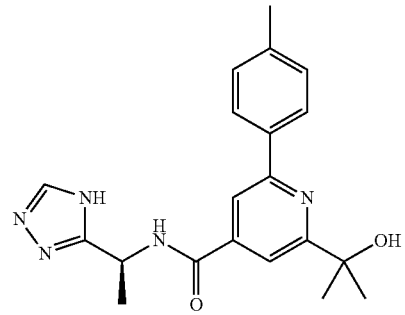 [SMILES: Cc1ccc(-c2cc(C(=O)N[C@@H](C)c3nnc[nH]3)cc(C(C)(C)O)n2)cc1]

2-(2-Hydroxypropan-2-yl)-6-(4-methylphenyl)-N-[(1S)-1-(4H-1,2,4-triazol-3-yl)ethyl]pyridine-4-carboxamide Step A: Methyl 2-(4-methylphenyl)-6-(prop-1-en-2-yl)pyridine-4-carboxylate To a degassed solution of palladium(II) acetate (21.8 mg, 0.10 mmol) and tris(2-methoxyphenyl)phosphine (68.4 mg, 0.19 mmol) in THF (1 mL) was added a degassed mixture of methyl 2,6-dichloroisonicotinate (250 mg, 1.21 mmol), tripotassium phosphate (386 mg, 1.82 mmol), and 2-isopropenyl-4,4,5,5-tetramethyl-1,3,2-dioxaborolane (0.285 mL, 1.52 mmol) in THF (1.5 mL) and water (0.625 mL). The mixture was heated to 63° C. After 4 h, a degassed solution of 4-methylphenylboronic acid (247 mg, 1.82 mmol) in THF (1.25 mL) was added. The resulting mixture was heated to 63° C. After 18 h, 4-methylphenylboronic acid (247 mg, 1.82 mmol), palladium(II) acetate (21.8 mg, 0.10 mmol), and tris(2-methoxyphenyl)phosphine (68.4 mg, 0.19 mmol) were added. The resulting mixture was heated to 63° C. After 18 h, the mixture was cooled to ambient temperature. Saturated aqueous NaHCO₃ was added and the mixture was extracted with ethyl acetate (3×). The combined organic extracts were washed with brine, dried over magnesium sulfate, filtered and concentrated. Purification by reverse phase chromatography (C-18, 80% water/acetonitrile→5% water/acetonitrile with 0.1% trifluoroacetic acid) gave the title compound (191 mg). MS 268.1 (M+1).

Step B: Methyl 2-(2-hydroxypropan-2-yl)-6-(4-methylphenyl)pyridine-4-carboxylate To a solution of methyl 2-(4-methylphenyl)-6-(prop-1-en-2-yl)pyridine-4-carboxylate (191 mg, 0.71 mmol) in methanol (3.6 mL) and DME (3.6 mL) was added cobalt(II)mesotetraphenylporphine (2.4 mg, 3.6 mop. After 30 min, tetraethylammonium borohydride (170 mg, 1.17 mmol) was added in 3 portions over 1 h. Saturated aqueous NaHCO$_3$ was added. The mixture was diluted with water and extracted with ethyl acetate (3×). The combined organic extracts were washed with brine, dried over magnesium sulfate, filtered and concentrated. Purification by reverse phase chromatography (C-18, 90% water/acetonitrile→5% water/acetonitrile with 0.1% trifluoroacetic acid) gave the title compound (165 mg). MS 286.1 (M+1).

Step C: 2-(2-Hydroxypropan-2-yl)-6-(4-methylphenyl)pyridine-4-carboxylic acid To a solution of methyl 2-(2-hydroxypropan-2-yl)-6-(4-methylphenyl)pyridine-4-carboxylate (165 mg, 0.58 mmol) in methyl alcohol (5.8 mL) was added sodium hydroxide (1 M; 1.16 mL, 1.16 mmol). The resulting mixture was heated to 60° C. After 30 min, the mixture was cooled to ambient temperature. Hydrogen chloride (96 µL, 1.16 mmol) was added. The resulting mixture was concentrated, giving the sodium chloride salt of the title compound. MS 272.1 (M+1).

Step D: 2-(2-Hydroxypropan-2-yl)-6-(4-methylphenyl)-N-[(1S)-1-(4H-1,2,4-triazol-3-yl)ethyl]pyridine-4-carboxamide To a solution of the sodium chloride salt of 2-(2-hydroxypropan-2-yl)-6-(4-methylphenyl)pyridine-4-carboxylic acid (224 mg, 0.58 mmol) in DMF (2.3 mL) was added the hydrochloride salt of (1S)-1-(4H-1,2,4-triazol-3-yl)ethanamine (160 mg, 0.87 mmol), HOST (89 mg, 0.58 mmol), triethylamine (322 pt, 2.31 mmol), and EDC (139 mg, 0.72 mmol). The resulting mixture was heated to 60° C. After 30 min, the mixture was cooled to ambient temperature. A small amount of water was added and the mixture was purified by reverse phase chromatography (C-18, 95% water/acetonitrile→5% water/acetonitrile with 0.1% trifluoroacetic acid). Treatment with 2 M hydrogen chloride in diethyl ether gave the title compound as the hydrochloride salt. (230 mg). HRMS 366.1920 (M+1). $^1$H NMR (399 MHz, DMSO): δ 9.28 (d, J=7.9 Hz, 1H); 8.38 (s, 1H); 8.18 (s, 1H); 8.07 (d, J=8.0 Hz, 2H); 8.02 (d, J=1.3 Hz, 1H); 7.33 (d, J=7.9 Hz, 2H); 5.37 (t, J=7.3 Hz, 1H); 2.38 (s, 3H); 1.59 (d, J=7.0 Hz, 3H); 1.52 (s, 6H).

Example 1.68

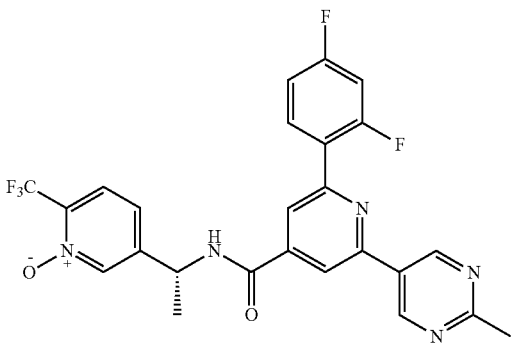

2-(2,4-Difluorophenyl)-6-(2-methylpyrimidin-5-yl)-N-{(1R)-1-[1-oxido-6-(trifluoromethyl)pyridin-3-yl]ethyl}isonicotinamide

Step A: 2-Chloro-6-(2,4-difluorophenyl)isonicotinic acid

To a solution of 2,6-dichloroisonicotinic acid (2.43 g, 12.67 mmol) in DMF (38 mL) and water (12.7 mL) were added (2,4-difluorophenyl)boronic acid (2.0 g, 12.67 mmol), tri(m-sulfophenyl)phosphine sodium salt (0.54 g, 0.95 mmol), palladium(II) acetate (71.0 mg, 0.32 mmol) and diisopropylamine (6.3 mL, 44.3 mmol). The mixture was heated 50° C. After 2.5 h, the mixture was cooled to ambient temperature and stirred for 18 h. HCl (1.0 M in water) was added and the mixture was was extracted with ethyl acetate (3×). The combined organic extracts were washed with brine, dried over magnesium sulfate, filtered and concentrated. Purification by reverse phase chromatography (C-18, 85% water/acetonitrile→5% water/acetonitrile with 0.1% trifluoroacetic acid) gave the title compound (1.24 g). MS 270.0 (M+1).

Step B: 2-(2,4-Difluorophenyl)-6-(2-methylpyrimidin-5-yl)isonicotinic acid

To a solution of 2-chloro-6-(2,4-difluorophenyl)isonicotinic acid (0.10 g, 0.37 mmol) in DMF (1.9 mL) and water (0.6 mL) were added (2-methylpyrimidin-5-yl)boronic acid (0.31 g, 2.23 mmol), palladium(II)acetate (12.5 mg, 0.06 mmol), 3,3',3"-phosphinidynetris(benzenesulfonic acid) trisodium salt (95.0 mg, 0.17 mmol) and diisopropylamine (0.19 mL, 1.30 mmol). The mixture was heated to 80° C. After 2 h, the mixture was filtered and the filtrate was purified by reverse phase chromatography (C-18, 95% water/acetonitrile→25% water/acetonitrile with 0.1% trifluoroacetic acid). To the product fractions was added HCl (2.0 M in ether) and the mixture was concentrated to give the hydrochloride salt of the title compound. MS 328.1 (M+1).

Step C: 2-(2,4-Difluorophenyl)-6-(2-methylpyrimidin-5-yl)-N-{(1R)-1-[1-oxido-6-(trifluoromethyl)pyridin-3-yl]ethyl}isonicotinamide To a solution of 2-(2,4-difluorophenyl)-6-(2-methylpyrimidin-5-yl)isonicotinic acid (21.3 mg, 0.05 mmol) in DMF (0.5 mL) were added hydrochloride salt of (1R)-1-[1-oxido-6-(trifluoromethyl)pyridin-3-yl]ethanamine (27.0 mg, 0.07 mmol), HATU (0.5 M in DMF; 0.16 mL, 0.08 mmol) and diisopropylethylamine (65 μL, 0.37 mmol). The mixture was stirred at ambient temperature. After 25 min, the mixture was purified by reverse phase chromatography (C-18, 95% water/acetonitrile→25% water/acetonitrile with 0.1% trifluoroacetic acid) gave the title compound, which was converted to hydrochloride salt using 2.0 M HCl in ether (31 mg). HRMS 516.1453 (M+1). $^1$H NMR (400 MHz, CDCl$_3$): δ 9.34 (s, 2H), 8.42 (s, 1H), 8.24-8.15 (m, 1H), 8.09 (s, 1H), 8.06 (s, 1H), 7.68 (d, J=8.3 Hz, 1H), 7.40 (d, J=8.4 Hz, 1H), 7.11-7.04 (m, 1H), 6.97 (t, J=9.8 Hz, 1H), 6.85 (d, J=7.0 Hz, 1H), 5.37-5.30 (m, 1H), 2.83 (s, 3H), 1.69 (d, J=7.1 Hz, 3H).

Example 1.79

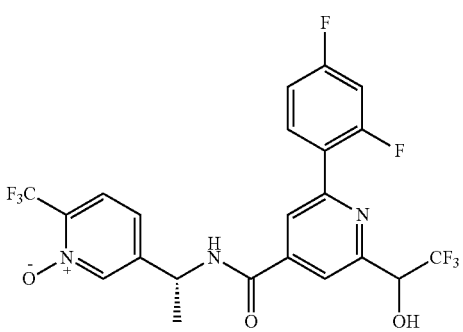

N-{(1R)-1-[6-(1,1-Difluoroethyl)-1-oxidopyridin-3-yl]ethyl}-2-(2,4-difluorophenyl)-6-(2,2,2-trifluoro-1-hydroxyethyl)isonicotinamide Step A: tert-Butyl 2,6-dichloroisonicotinate To a solution of 2,6-dichloroisonicotinic acid (10.0 g, 52.1 mmol) in THF (200 mL) were added di-tert-butyl dicarbonate (12.5 g, 57.3 mmol) and DMAP (1.9 g, 15.6 mmol). The mixture was stirred at ambient temperature. After 72 h, water was added and the mixture was extracted with ethyl acetate (3×). The combined organic extracts were washed with brine, dried over sodium sulfate, filtered and concentrated.

Step B: tert-Butyl 2-chloro-6-vinylisonicotinate

To a solution of tert-butyl 2,6-dichloroisonicotinate (11.0 g, 44.3 mmol) in THF (200 mL) were added potassium vinyltrifluoroborate (7.1 g, 53.2 mmol), dichloro[1,1'-bis(diphenylphosphino)ferrocene]palladium(II) dichloromethane adduct (0.97 g, 1.33 mmol) and triethylamine (9.3 mL, 66.5 mmol). The mixture was heated to 65° C. After 1 h, saturated aqueous sodium bicarbonate was added and the mixture was extracted with ethyl acetate (3×). The combined organic extracts were washed with brine, dried over sodium sulfate, filtered and concentrated. Purification by silica gel chromatography (100% hexanes→90% hexanes/ethyl acetate) gave no separation of desired product. The mixture was carried onto next step.

Step C: tert-Butyl 2-chloro-6-formylisonicotinate

To a solution of tert-butyl 2-chloro-6-vinylisonicotinate (9.6 g, 40.1 mmol) in THF (100 mL) and water (100 mL) were added osmium tetroxide (4% in water; 6.3 mL, 0.80 mmol) and sodium periodate (25.7 g, 120.0 mmol). The mixture was stirred at ambient temperature. After 30 min, saturated aqueous sodium bicarbonate was added and the mixture was extracted with ethyl acetate (3×). The combined organic extracts were washed with brine, dried over sodium sulfate, filtered and concentrated.

Step D: tert-Butyl 2-chloro-6-(2,2,2-trifluoro-1-hydroxyethyl)isonicotinate

To a solution of tert-butyl 2-chloro-6-formylisonicotinate (1.5 g, 6.2 mmol) in THF (40 mL) were added (trifluoromethyl)trimethylsilane (1.49 mL, 4.31 mmol) and ground 4 A° molecular sieves. The mixture was cooled to 0° C. and TBAP (1.0 M in THF; 1.86 mL, 1.86 mmol) was added dropwise. The mixture was warmed to ambient temperature. After 30 min, additional (trifluoromethyl)trimethylsilane (0.5 mL, 1.44 mmol), TBAP (1.0 M in THF; 0.62 mL, 0.62 mmol) and ground 4 A° molecular sieves were added. After 30 min, the mixture was filtered with Celite. Aqueous 1 N HCl was added to the filtrate and the filtrate was extracted with ethyl acetate (3×). The combined organic extracts were washed with brine, dried over sodium sulfate, filtered and concentrated. Purification by silica gel chromatography (100% hexanes→95% hexanes/ethyl acetate) gave the title compound (1.4 g). MS 312.2 (M+1).

Step E: tert-Butyl 2-(2,4-difluorophenyl)-6-(2,2,2-trifluoro-1-hydroxyethyl)isonicotinate To a solution of tort-butyl 2-chloro-6-(2,2,2-trifluoro-1-hydroxyethyl)isonicotinate (0.5 g, 1.6 mmol) in toluene (15 mL) were added (2,4-difluorophenyl)boronic acid (0.38 g, 2.41 mmol), palladium(II) acetate (36.0 mg, 0.16 mmol), 2-dicyclohexylphosphino-2',4',6'-triisopropylbiphenyl (76.0 mg, 0.16 mmol) and potassium phosphate tribasic (1.02 g, 4.81 mmol). The mixture was degassed and heated to 100° C. After 1 h, saturated aqueous sodium bicarbonate was added and the mixture was extracted with ethyl acetate (3×). The combined organic extracts were washed with brine, dried over sodium sulfate, filtered and concentrated. Purification by silica gel chromatography (100% hexanes→80% hexanes/ethyl acetate) gave the title compound (0.56 g). MS 390.3 (M+1).

Step F: 2-(2,4-Difluorophenyl)-6-(2,2,2-trifluoro-1-hydroxyethyl)isonicotinic acid To a solution of tert-butyl 2-(2,4-difluorophenyl)-6-(2,2,2-trifluoro-1-hydroxyethyl)isonicotinate (0.56 g, 1.44 mmol) in dichloromethane (3 mL) was added trifluoroacetic acid (3 mL). The mixture was stirred at ambient temperature. After 18 h, additional trifluoroacetic acid (1 mL) was added and the mixture was stirred at ambient for 1 h. The mixture was concentrated to dryness to give the title compound (0.43 g). MS 334.2 (M+1).

Step G: N-{(1R)-1-[6-(1,1-Difluoroethyl)-1-oxidopyridin-3-yl]ethyl}-2-(2,4-difluorophenyl)-6-(2,2,2-trifluoro-1-hydroxyethyl)isonicotinamide To a solution of 2-(2,4-difluorophenyl)-6-(2,2,2-trifluoro-1-hydroxyethyl)isonicotinic acid (0.15 g, 0.45 mmol) in DMF (2.5 mL) were added hydrochloride salt of (1R)-1-[1-oxido-6-(trifluoromethyl)pyridin-3-yl]ethanamine (0.16 g, 0.59 mmol), EDC (0.17 g, 0.90 mmol), HOAT (61.3 mg, 0.45 mmol) and triethylamine (0.38 mL, 2.7 mmol). The mixture was stirred at 60° C. After 1 h, the mixture was cooled to ambient temperature and saturated aqueous NaHCO$_3$ was added. The mixture was extracted with ethyl acetate (3×). The combined organic extracts were washed with brine, dried over sodium sulfate, filtered and concentrated. The mixture was suspended in dichloromethane and the solid was filtered. The solid cake was washed with cold dichloromethane and dried under hi-vac. The product was treated with HCl (2.0 M in ether) to give the hydrochloride salt of the title compound (0.18 g). HRMS 522.1063 (M+1). $^1$H NMR (400 MHz, CD$_3$OD): δ 8.48 (s, 1H); 8.17 (s, 1H); 8.09-7.99 (m, 2H); 7.89 (d, J=8.4 Hz, 1H); 7.65 (d, J=8.4 Hz, 1H); 7.10 (t, J=9.1 Hz, 2H); 5.28-5.18 (m, 2H); 1.62 (d, J=7.2 Hz, 3H).

Example 1.87

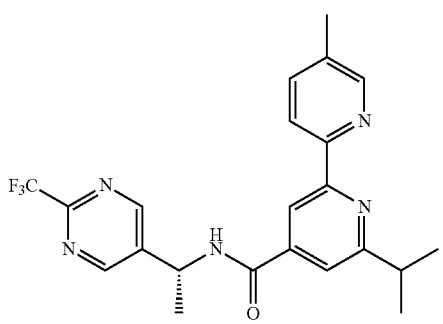 [SMILES: Cc1ccc(-c2cc(C(=O)N[C@H](C)c3cnc(C(F)(F)F)nc3)cc(C(C)C)n2)nc1]

6-Isopropyl-5'-methyl-N-{(1R)-1-[2-(trifluoromethyl)pyrimidin-5-yl]-ethyl}-2,2'-bipyridine-4-carboxamide Step A: Methyl 2-chloro-6-isopropenylisonicotinate To a solution of 2-chloro-6-isopropenylisonicotinic acid (0.25 g, 1.27 mmol) in dichloromethane (4.7 mL) and methanol (1.6 mL) was added (diazomethyl)(trimethyl)silane (0.63 mL, 1.27 mmol). After the addition, the mixture was concentrated and carried onto the next step. MS 212.0 (M+1).

Step B: Methyl 6-isopropenyl-5'-methyl-2,2'-bipyridine-4-carboxylate

To a solution of methyl 2-chloro-6-isopropenylisonicotinate (0.5 g, 2.36 mmol) in DMF (12 mL) were added 5-methyl-2-(4,4,5,5-tetramethyl-1,3,2-dioxaborolan-2-yl)pyridine (1.3 g, 5.9 mmol), palladium(II)acetate (26.5 mg, 0.12 mmol), cesium carbonate (1.54 g, 4.72 mmol), dichloro[1,1'-bis(diphenylphosphino)ferrocene]palladium(II) dichloromethane adduct (0.13 g, 0.24 mmol) and copper(I) chloride (0.23 g, 2.36 mmol). The mixture was purged with argon and heated to 100° C. After 45 min, saturated aqueous NaHCO$_3$ was added. The mixture was extracted with ethyl acetate (3×). The combined organic extracts were washed with water (3×), brine, dried over sodium sulfate, filtered and concentrated. Purification by silica gel chromatography (100% hexanes→75% hexanes/ethyl acetate) gave the title compound (0.55 g). MS 269.1 (M+1).

Step C: Methyl 6-isopropyl-5'-methyl-2,2'-bipyridine-4-carboxylate

To a solution of methyl 6-isopropenyl-5'-methyl-2,2'-bipyridine-4-carboxylate (0.25 g, 0.93 mmol) in ethanol (9.3 mL) was palladium (10% on carbon; 49.6 mg, 0.047 mmol). The mixture was purged with hydrogen (3×) and stirred under hydrogen (1 atm). After 35 min, the mixture was filtered with Celite and the filtrate was concentrated. MS 271.2 (M+1).

Step D: 6-Isopropyl-5'-methyl-2,2'-bipyridine-4-carboxylic acid

To a solution of methyl 6-isopropyl-5'-methyl-2,2'-bipyridine-4-carboxylate (275 mg, 1.02 mmol) in methanol (10 mL) was added sodium hydroxide (1.0 M in water; 2.03 mL, 2.03 mmol). The mixture was heated to 50 C. After 45 min, HCl (1.0 M in water; 2.03 mL; 2.03 mmol) was added and the mixture was concentrated to give the sodium chloride salt of the title compound (0.32 g). MS 257.1 (M+1).

Step E: 6-Isopropyl-5'-methyl-N-{(1R)-1-[2-(trifluoromethyl)pyrimidin-5-yl]ethyl}-2,2'-bipyridine-4-carboxamide To a solution of 6-isopropyl-5'-methyl-2,2'-bipyridine-4-carboxylic acid (25.0 mg, 0.07 mmol) in DMF (0.3 mL) were added hydrochloride salt of (1R)-1-[2-(trifluoromethyl)pyrimidin-5-yl]ethanamine (22.1 mg, 0.08 mmol), HATU (38.2 mg, 0.10 mmol) and diisopropylethylamine (58.5 μL, 0.34 mmol). The mixture was stirred at ambient temperature. After 20 min, the mixture was purified by reverse phase chromatography (C-18, 95% water/acetonitrile→25% water/acetonitrile with 0.1% trifluoroacetic acid) gave the title compound (24 mg), HRMS 430.1850 (M+1). $^1$H NMR (400 MHz, CDCl$_3$): δ 8.96 (s, 2H), 8.48 (s, 1H), 8.43 (d, 8.1 Hz, 1H), 8.37 (s, 1H), 7.67 (d, J=8.2 Hz, 1H), 7.63 (s, 1H), 6.96 (d, J=6.7 Hz, 1H), 5.44-5.35 (m, 1H), 3.24-3.14 (m, 1H), 2.42 (s, 3H), 1.74 (d, J=7.2 Hz, 3H), 1.37 (d, J=6.9 Hz, 6H).

Example 2.3

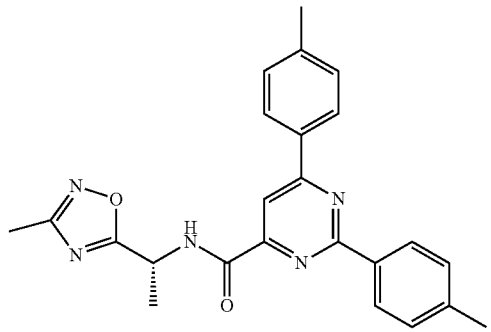

N-[(1R)-1-(3-Methyl-1,2,4-oxadiazol-5-yl)ethyl]-2,6-bis(4-methylphenyl)pyrimidine-4-carboxamide Step A: Methyl 2,6-bis(4-methylphenyl)pyrimidine-4-carboxylate To a solution of methyl 2,6-dichloropyrimidine-4-carboxylate (0.39 g, 1.87 mmol) in DMF (15 mL) were added (4-methylphenyl)boronic acid (0.84 g, 6.17 mmol), potassium phosphate tribasic (0.79 g, 3.74 mmol) and dichloro[1,1'-bis(diphenylphosphino)ferrocene]palladium(II) dichloromethane adduct (0.15 g, 0.19 mmol). The mixture was heated to 80° C. After 16 h, the mixture was cooled to ambient temperature. Saturated aqueous sodium bicarbonate was added and the mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound (0.31 g). MS 319.2 (M+1).

Step B: 2,6-Bis(4-methylphenyl)pyrimidine-4-carboxylic acid

To a solution of methyl 2,6-bis(4-methylphenyl)pyrimidine-4-carboxylate (0.31 g, 0.98 mmol) in THF (10 mL) and water (10 mL) were added sodium hydroxide (1.0 M in water; 2.05 mL, 2.05 mmol). The mixture was stirred at ambient temperature. After 18 h, HCl (1.0 M in water) was added and the mixture was extracted with dichloromethane (3×). The combined organic extracts were washed with brine, dried over sodium sulfate, filtered and concentrated. MS 305.1 (M+1).

Step C: N-[(1R)-1-(3-Methyl-1,2,4-oxadiazol-5-yl)ethyl]-2,6-bis(4-methylphenyl)pyrimidine-4-carboxamide To a solution of 2,6-bis(4-methylphenyl)pyrimidine-4-carboxylic acid (15.0 mg, 0.05 mmol) in DMF (1 mL) were added hydrochloride salt of (1R)-1-(3-methyl-1,2,4-oxadiazol-5-yl)ethanamine (14.7 mg, 0.07 mmol), EDC (23.8 mg, 0.15 mmol), HOBT (22.6 mg, 0.15 mmol) and diisopropylethylamine (34.4 μL, 0.20 mmol). The mixture was stirred at ambient temperature. After 18 h, the mixture was purified by reverse chromatography (C-18, 95% water/acetonitrile→5% water/acetonitrile with 0.1% trifluoroacetic acid) to give the trifluoroacetate salt of the title compound (33 mg). HRMS 414.1924 (M+1). $^1$H NMR (499 MHz, DMSO): δ 9.80 (d, J=8.3 Hz, 1H); 8.66 (d, J=8.0 Hz, 2H); 8.37-8.29 (m, 3H); 7.42 (t, J=9.1 Hz, 4H); 5.55-5.47 (m, 1H); 2.43 (d, J=3.4 Hz, 6H); 2.35 (s, 3H); 1.73 (d, J=7.1 Hz, 3H).

Example 3.13

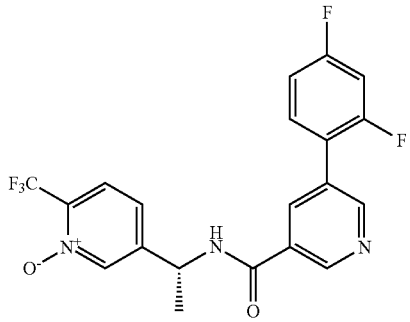 [SMILES: C[C@@H](NC(=O)c1cncc(-c2ccc(F)cc2F)c1)c1ccc(C(F)(F)F)[n+]([O-])c1]

5-(2,4-Difluorophenyl)-N-{(1R)-1-[1-oxido-6-(trifluoromethyl)pyridin-3-yl]ethyl}nicotinamide Step A: 5-(2,4-Difluorophenyl)nicotinic acid To a solution of 5-bromonicotinic acid (0.5 g, 2.48 mmol) in DMF (7.4 mL) and water (2.5 mL) were added (2,4-difluorophenyl)boronic acid (0.43 g, 2.72 mmol), palladium acetate (27.8 mg, 0.12 mmol), 3,3',3"-phosphinidynetris(benzensulfonic acid) trisodium salt (0.21 g, 0.37 mmol) and diisopropylamine (1.23 mL, 8.66 mmol). The mixture was heated to 80° C. After 1.5 h, the mixture was cooled to ambient temperature and filtered. The filtrate was purified by reverse chromatography (C-18, 95% water/acetonitrile→5% water/acetonitrile with 0.1% trifluoroacetic acid). The product was converted to hydrochloride salt by adding HCl (2.0 M in ether) and concentrated to give the hydrochloride salt of the title compound (0.65 g). MS 236.0 (M+1).

Step B: 5-(2,4-Difluorophenyl)-N-{(1R)-1-[1-oxido-6-(trifluoromethyl)pyridin-3-yl]ethyl}nicotinamide To a solution of 5-(2,4-difluorophenyl)nicotinic acid (40.0 mg, 0.15 mmol) in DMF (0.7 mL) were added hydrochloride salt of (1R)-1-[1-oxido-6-(trifluoromethyl)pyridin-3-yl]ethanamine (49.3 mg, 0.18 mmol), EDC (33.9 mg, 0.18 mmol), HOBT (22.6 mg, 0.15 mmol) and triethylamine (0.10 mL, 0.74 mmol). The mixture was stirred at ambient temperature for 18 h. Purification by reverse chromatography (C-18, 95% water/acetonitrile→25% water/acetonitrile with 0.1% trifluoroacetic acid) gave the title product, which was converted to hydrochloride salt using 2.0 M HCl in ether (47 mg). HRMS 424.1086. $^1$H NMR (400 MHz, CD$_3$OD): δ 9.22 (s, 1H); 9.15 (s, 1H); 9.00 (s, 1H); 8.52 (s, 1H); 7.92 (d, J=8.4 Hz, 1H); 7.83-7.73 (m, 1H); 7.70 (d, J=8.4 Hz, 1H); 7.31-7.21 (m, 2H); 5.33-5.25 (m, 1H); 1.67 (d, J=7.1 Hz, 3H).

Example 3.24 Example 5.61

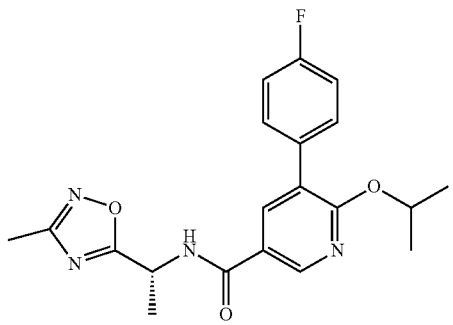 [SMILES: Cc1noc([C@@H](C)NC(=O)c2cnc(OC(C)C)c(-c3ccc(F)cc3)c2)n1]

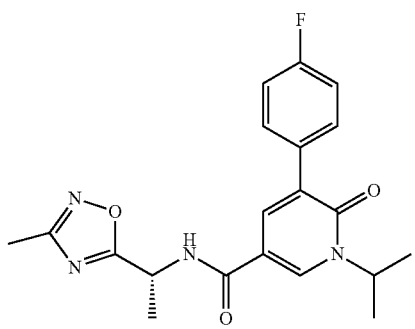 [SMILES: Cc1noc([C@@H](C)NC(=O)c2cc(-c3ccc(F)cc3)c(=O)n(C(C)C)c2)n1]

5-(4-Fluorophenyl)-6-isopropoxy-N-[(1R)-1-(3-methyl-1,2,4-oxadiazol-5-yl)ethyl]nicotinamide (Example 3.24) and 5-(4-fluorophenyl)-1-isopropyl-N-[(1R)-1-(3-methyl-1,2,4-oxadiazol-5-yl)ethyl]-6-oxo-1,6-dihydropyridine-3-carboxamide (Example 5.61)

Step A: Methyl 5-(4-fluorophenyl)-6-oxo-1,6-dihydropyridine-3-carboxylate

To a solution of methyl 5-bromo-6-oxo-1,6-dihydropyridine-3-carboxylate (0.50 g, 2.16 mmol) in DMF (8.1 mL) and water 2.7 mL) were added (4-fluorophenyl)boronic acid (0.38 g, 2.69 mmol), palladium(II) acetate (36.3 mg, 0.16 mmol), tris(3-sulfonatophenyl)phosphine hydrate sodium salt (0.31 g, 0.49 mmol) and diisopropylamine (1.54 mL, 10.8 mmol). The mixture was heated in the microwave reactor at 125° C. for 15 min. The mixture was filtered and water was added to the filtrate. The mixture was extracted with ethyl acetate and the organic layer was washed with water (3×), brine, dried over sodium sulfate, filtered and concentrated. Purification by silica gel chromatography (100% dichloromethane→70% dichloromethane/ethyl acetate) gave the title compound (0.35 g). MS 248.1 (M+1).

Step B: Methyl 5-(4-fluorophenyl)-6-isopropoxynicotinate and methyl 5-(4-fluorophenyl)-1-isopropyl-6-oxo-1,6-dihydropyridine-3-carboxylate To a solution of methyl 5-(4-fluorophenyl)-6-oxo-1,6-dihydropyridine-3-carboxylate (0.18 g, 0.72 mmol) in DMF (3 mL) were added 2-iodopropane (0.61 g, 3.58 mmol) and cesium carbonate (0.35 g, 1.07 mmol). The mixture was stirred at ambient temperature. After 2 h, the mixture was filtered and washed with methanol. The filtrate was concentrated to remove methanol. The DMF solution was carried onto the next step.

Step C: 5-(4-Fluorophenyl)-6-isopropoxynicotinic acid and 5-(4-fluorophenyl)-1-isopropyl-6-oxo-1,6-dihydropyridine-3-carboxylic acid To a solution of methyl 5-(4-fluorophenyl)-6-isopropoxynicotinate and methyl 5-(4-fluorophenyl)-1-isopropyl-6-oxo-1,6-dihydropyridine-3-carboxylate in DMF (5 mL) and water (2 mL) were added sodium hydroxide (1.0 M in water; 1.43 mL, 1.43 mmol). The mixture was stirred at 50° C. After 1 h, additional sodium hydroxide (1.0 M in water; 1.43 mL, 1.43 mmol) was added. After 2 h, HCl (1.0 M in water) was added and the mixture was extracted with dichloromethane (3×). The combined organic extracts were washed with brine, dried over sodium sulfate, filtered and concentrated. The desired products were still in the DMF layer. The DMF solution was carried onto the next step.

Step D: 5-(4-Fluorophenyl)-6-isopropoxy-N-[(1R)-1-(3-methyl-1,2,4-oxadiazol-5-yl)ethyl]nicotinamide (Example 3.24) and 5-(4-fluorophenyl)-1-isopropyl-N-[(1R)-1-(3-methyl-1,2,4-oxadiazol-5-yl)ethyl]-6-oxo-1,6-dihydropyridine-3-carboxamide (Example 5.61)

To a solution of 5-(4-fluorophenyl)-6-isopropoxynicotinic acid and 5-(4-fluorophenyl)-1-isopropyl-6-oxo-1,6-dihydropyridine-3-carboxylic acid (50 mg, 0.09 mmol) in DMF (0.5 mL) were added hydrochloride salt of (1R)-1-(3-methyl-1,2,4-oxadiazol-5-yl)ethanamine (21.8 mg, 0.11 mmol), HATU (0.5 M in DMF; 0.27 mL, 0.14 mmol) and diisopropylethylamine (63 μL, 0.36 mmol). The mixture was stirred at ambient temperature. After 10 min, HCl (1.0 M) was added and the mixture was purified by reverse chromatography (C-18, 95% water/acetonitrile→5% water/acetonitrile with 0.1% trifluoroacetic acid) to give the N-alkylated product, 5-(4-fluorophenyl)-1-isopropyl-N-[(1R)-1-(3-methyl-1,2,4-oxadiazol-5-yl)ethyl]-6-oxo-1,6-dihydropyridine-3-carboxamide (example 5.61) (20.9 mg), HRMS 385.1685. $^1$H NMR (400 MHz, CDCl$_3$): δ 8.21 (d, J=2.5 Hz, 1H); 7.69-7.63 (m, 3H); 7.12 (t, J=8.5 Hz, 2H); 6.52 (d, J=7.7 Hz, 1H); 5.60-5.51 (m, 1H); 5.37-5.27 (m, 1H); 2.41 (s, 3H); 1.70 (d, J=7.1 Hz, 3H); 1.45 (dd, J=6.8, 2.2 Hz, 6H). The o-alkylated product was repurified by reverse chromatography (C-18, 95% water/acetonitrile→5% water/acetonitrile with 0.05% ammonium hydroxide) to give 5-(4-fluorophenyl)-6-isopropoxy-N-[(1R)-1-(3-methyl-1,2,4-oxadiazol-5-yl)ethyl]nicotinamide (example 3.24) (16.1 mg). HRMS 385.1679. $^1$H NMR (400 MHz, CDCl$_3$): δ 8.59 (s, 1H); 8.01 (d, J=2.3 Hz, 1H); 7.55 (dd, J=8.3, 5.4 Hz, 2H); 7.16-7.08 (m, 2H); 6.63 (d, J=7.7 Hz, 1H); 5.63-5.55 (m, 1H); 5.51-5.43 (m, 1H); 2.40 (s, 3H); 1.71 (d, J=7.1 Hz, 3H); 1.35 (d, J=6.2 Hz, 6H).

Example 4.1

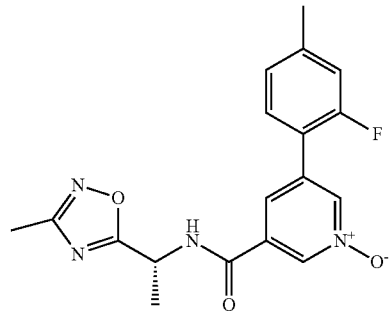 [SMILES: Cc1ccc(-c2cc(C(=O)N[C@H](C)c3nc(C)no3)c[n+]([O-])c2)c(F)c1]

5-(2-Fluoro-4-methylphenyl)-N-[(1R)-1-(3-methyl-1,2,4-oxadiazol-5-yl)ethyl]nicotinamide 1-oxide Step A: Ethyl 5-(2-fluoro-4-methylphenyl)nicotinate To a solution of ethyl 5-bromonicotinate (0.58 g, 2.53 mmol) in acetonitrile (15 mL) and water (5 mL) were added (2-fluoro-4-methylphenyl)boronic acid (0.47 g, 3.04 mmol), 3,3',3''-phosphinidynetris(benzenesulfonic acid) trisodium salt (0.22 g, 0.38 mmol), palladium(II)acetate (28.4 mg, 0.13 mmol) and diisopropylamine (0.90 mL, 6.32 mmol). The mixture was heated to 80° C. After 1 h, the mixture was cooled to ambient temperature and saturated aqueous NaHCO$_3$ was added. The mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound (0.67 g). MS 260.1 (M+1).

Step B: 5-(2-Fluoro-4-methylphenyl)nicotinic acid

To a solution of ethyl 5-(2-fluoro-4-methylphenyl)nicotinate (0.67 g, 2.58 mmol) in methanol (10 mL), THF (10 mL) and water (5 mL) were added sodium hydroxide (1.0 M in water; 5.17 mL, 5.17 mmol). The mixture was stirred at ambient temperature. After 40 min, HCl (1.0 M in water; 5.17 mL, 5.17 mmol) was added and the mixture was concentrated to give the sodium chloride salt of the title compound (0.87 g). MS 232.1 (M+1).

Step C: 5-(2-Fluoro-4-methylphenyl)nicotinic acid 1-oxide

To a solution of 5-(2-fluoro-4-methylphenyl)nicotinic acid (0.15 g, 0.43 mmol) in dichloromethane (5 mL) and methanol (3 mL) was added 3-chloroperbenzoic acid (70%; 0.16 g, 0.65 mmol). The mixture was stirred at ambient temperature. After 18 h, additional 3-chloroperbenzoic acid (70%; 0.19 g, 0.86 mmol) was added. The mixture was continued to stir at ambient temperature. After 24 h, additional 3-chloroperbenzoic acid (70%; 0.19 g, 0.86 mmol) was added. After 18 h, the mixture was concentrated. Purification by reverse chromatography (C-18, 95% water/acetonitrile→25% water/acetonitrile with 0.1% trifluoroacetic acid) gave the title compound (70 mg). MS 248.0 (M+1).

Step D: 5-(2-Fluoro-4-methylphenyl)-N-[(1R)-1-(3-methyl-1,2,4-oxadiazol-5-yl)ethyl]nicotinamide 1-oxide To a solution of 5-(2-fluoro-4-methylphenyl)nicotinic acid 1-oxide (22.6 mg, 0.09 mmol) in DMF (0.5 mL) were added hydrochloride salt of (1R)-1-(3-methyl-1,2,4-oxadiazol-5-yl)ethanamine (23.8 mg, 0.12 mmol), EDC (26.3 mg, 0.14 mmol), HOBT (15.4 mg, 0.10 mmol) and diisopropylethylamine (64 µL, 0.37 mmol). The mixture was stirred at ambient temperature. After 72 h, the mixture was purified by reverse chromatography (C-18, 95% water/acetonitrile→25% water/acetonitrile with 0.1% trifluoroacetic acid) to give the title compound (18.4 mg). HRMS 357.1367 (M+1). $^1$H NMR (400 MHz, CDCl$_3$): δ 9.02 (s, 1H); 8.73 (d, J=7.6 Hz, 1H); 8.53 (s, 1H); 7.98 (s, 1H); 7.32 (t, J=8.0 Hz, 1H); 7.08 (d, J=8.0 Hz, 1H); 7.02 (d, J=11.8 Hz, 1H); 5.60-5.51 (m, 1H); 2.42 (s, 3H); 2.29 (s, 3H); 1.80 (d, J=7.1 Hz, 3H).

Example 5.88

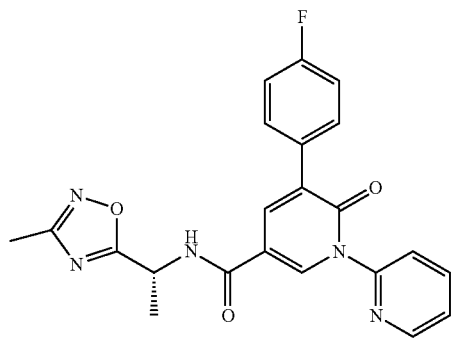 [SMILES: Cc1noc([C@@H](C)NC(=O)c2cc(-c3ccc(F)cc3)c(=O)n(-c3ccccn3)c2)n1]

3-(4-Fluorophenyl)-N-[(1R)-1-(3-methyl-1,2,4-oxadiazol-5-yl)ethyl]-2-oxo-2H-1,2'-bipyridine-5-carboxamide

Step A: Methyl 5-(4-fluorophenyl)-6-oxo-1,6-dihydropyridine-3-carboxylate

To a solution of methyl 5-bromo-6-oxo-1,6-dihydropyridine-3-carboxylate (0.5 g, 2.16 mmol) in DMF (8.1 mL) and water (2.7 mL) were added (4-fluorophenyl)boronic acid (0.38 g, 2.69 mmol), palladium(II)acetate (36.3 mg, 0.16 mmol), tris(3-sulfonatophenyl)phosphine hydrate sodium salt (0.31 g, 0.49 mmol) and diisopropylamine (1.54 mL, 10.77 mmol). The mixture was heated in the microwave reactor for 15 min at 125° C. The mixture was filtered and water was added to the filtrate. The mixture was extracted with ethyl acetate (3×). The combined organic extracts were washed with water (3×), brine, dried over sodium sulfate, filtered and concentrated. Purification by silica gel chromatography (100% dichloromethane→70% dichloromethane/ethyl acetate) gave the title compound (0.35 g). MS 248.1 (M+1).

Step B: Methyl 3-(4-fluorophenyl)-2-oxo-2H-1,2'-bipyridine-5-carboxylate

To a solution of methyl 5-(4-fluorophenyl)-6-oxo-1,6-dihydropyridine-3-carboxylate (77.0 mg, 0.31 mmol) in dioxane (2.1 mL) were added 2-bromopyridine (0.15 g, 0.92 mmol), trans-(1R,2R)—N,N'-bismethyl-1,2-cyclohexanediamine (17.7 mg, 0.13 mmol) and potassium carbonate (86.0 mg, 0.62 mmol). The mixture was heated in the microwave reactor at 120° C. for 1 h then heated in an oil bath at 80° C. for 8 h. The mixture was cooled to ambient temperature and dichloromethane was added. The mixture was washed with water, sat. NaHCO$_3$, brine and dried with sodium sulfate, filtered and concentrated. Purification by silica gel chromatography (100% dichloromethane→75% dichloromethane/ethyl acetate) gave the title compound (94 mg). MS 325.1 (M+1).

Step C: 3-(4-Fluorophenyl)-2-oxo-2H-1,2'-bipyridine-5-carboxylic acid

To a solution of methyl 3-(4-fluorophenyl)-2-oxo-2H-1,2'-bipyridine-5-carboxylate (93.0 mg, 0.29 mmol) in dioxane (5 mL) and water (2 mL) was added NaOH (1.0 M in water; 0.36 mL, 0.36 mmol). The mixture was stirred at 60 C. After 1.25 h, the mixture was cooled to ambient temperature and HCl (1.0 M in water; 0.36 mL, 0.36 mmol) was added. The sample was put under the lyophilizer to give the sodium chloride salt of the title compound (111 mg). MS 311.1 (M+1).

Step D: 3-(4-Fluorophenyl)-N-[(1R)-1-(3-methyl-1,2,4-oxadiazol-5-yl)ethyl]-2-oxo-2H-1,2'-bipyridine-5-carboxamide To a solution of 3-(4-fluorophenyl)-2-oxo-2H-1,2'-bipyridine-5-carboxylic acid (20.0 mg, 0.05 mmol) in DMF (0.5 mL) were added hydrochloride salt of (1R)-1-(3-methyl-1,2,4-oxadiazol-5-yl)ethanamine (13.6 mg, 0.07 mmol), HATU (0.5 M in DMF; 0.16 mL, 0.08 mml) and diisopropylethylamine (36 µL, 0.21 mmol). The mixture was stirred at ambient temperature. After 30 min, the mixture was purified by reverse chromatography (C-18, 95% water/acetonitrile→25% water/acetonitrile with 0.1% trifluoroacetic acid) to give the title compound (20 mg). HRMS 420.1470 (M+1). $^1$H NMR (400 MHz, CDCl$_3$): δ 8.62 (d, J=4.8 Hz, 1H); 8.53 (d, J=2.5 Hz, 1H); 7.94-7.83 (m, 3H); 7.70 (dd, J=8.3, 5.4 Hz, 2H); 7.41 (t, J=5.8 Hz, 1H); 7.12 (t, J=8.5 Hz, 2H); 6.66 (d, J=7.7 Hz, 1H); 5.60-5.51 (m, 1H); 2.40 (s, 3H); 1.69 (d, J=7.1 Hz, 3H).

Example 5.134

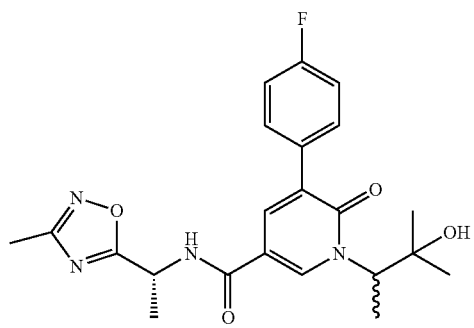 [SMILES: Cc1noc([C@@H](C)NC(=O)c2cc(-c3ccc(F)cc3)c(=O)n(C(C)C(C)(C)O)c2)n1]

5-(4-Fluorophenyl)-1-(3-hydroxy-3-methylbutan-2-yl)-N-[(1R)-1-(3-methyl-1,2,4-oxadiazol-5-yl)ethyl]-6-oxo-1,6-dihydropyridine-3-carboxamide Step A: Methyl 5-bromo-6-oxo-1-(3-oxobutan-2-yl)-1,6-dihydropyridine-3-carboxylate To a solution of methyl-5-bromo-6-oxo-1,6-dihydropyridine-3-carboxylate (10.0 g, 43.1 mmol) and cesium carbonate (16.9 g, 51.7 mmol) in N,N-dimethylformamide (144 mL) was added 3-bromo-2-butanone (7.8 g, 51.7 mmol). The reaction mixture was stirred at ambient temperature. After 20 min, saturated aqueous sodium bicarbonate and water were added. The mixture was extracted with ethyl acetate (3×). The combined organic extracts were washed with water (3×), brine, dried over magnesium sulfate, filtered and concentrated. Purification by silica gel chromatography (100% dichloromethane→50% dichloromethane/ethyl acetate) gave the title compound. MS 302.1 (M).

Step B: Methyl 5-(4-fluorophenyl)-6-oxo-1-(3-oxobutan-2-yl)-1,6-dihydropyridine-3-carboxylate To a solution of methyl 5-bromo-6-oxo-1-(3-oxobutan-2-yl)-1,6-dihydropyridine-3-carboxylate (11.3 g, 37.4 mmol) in N,N-dimethylformamide (112 mL) and water (37 mL) were added 4-fluorophenylboronic acid (6.28 g, 44.9 mmol), palladium acetate (0.17 g, 0.75 mmol), 3,3',3''-phosphinidynetris(benzenesulfonic acid) trisodium salt (1.28 g, 2.24 mmol) and diisopropylamine (13.3 mL, 94.0 mmol). The reaction mixture was heated to 80° C. After 30 min, the mixture was cooled to ambient temperature. Saturated aqueous sodium bicarbonate and water were added. The mixture was extracted with ethyl acetate (3×). The combined organic extracts were washed with water (3×), brine, dried over magnesium sulfate, filtered and concentrated. Purification by silica gel chromatography (100% dichloromethane→80% dichloromethane/ethyl acetate) gave the title compound. MS 318.2 (M+1).

Step C: Methyl 5-(4-fluorophenyl)-1-(3-hydroxy-3-methylbutan-2-yl)-6-oxo-1,6-dihydropyridine-3-carboxylate To a solution of methyl 5-(4-fluorophenyl)-6-oxo-1-(3-oxobutan-2-yl)-1,6-dihydropyridine-3-carboxylate (11.1 g, 35.0 mmol) in tetrahydrofuran (175 mL) at 0° C. was added methylmagnesium bromide (3.0 M in THF; 14.0 mL, 42.0 mmol). After 20 min, the mixture was quenched with saturated aqueous sodium bicarbonate. The mixture was cooled to ambient temperature and extracted with ethyl acetate (3×). The combined organic extracts were washed with brine, dried over magnesium sulfate, filtered and concentrated. Purification by silica gel chromatography (100% dichloromethane→80% dichloromethane/ethyl acetate) gave the title compound. MS 334.2 (M+1).

Step D: 5-(4-Fluorophenyl)-1-(3-hydroxy-3-methylbutan-2-yl)-6-oxo-1,6-dihydropyridine-3-carboxylic acid To a solution of methyl 5-(4-fluorophenyl)-1-(3-hydroxy-3-methylbutan-2-yl)-6-oxo-1,6-dihydropyridine-3-carboxylate (400 mg, 1.20 mmol) in tetrahydrofuran (6 mL) and water (2 mL) was added sodium hydroxide (55 mg, 1.38 mmol). The resulting mixture was heated to 50° C. After 140 min, the mixture was cooled to ambient temperature. Hydrogen chloride (0.113 mL, 1.38 mmol) was added and the mixture was concentrated to give the sodium chloride salt of the title compound. MS 342.2 (M+Na).

Step E: 5-(4-Fluorophenyl)-1-(3-hydroxy-3-methylbutan-2-yl)-N-[(1R)-1-(3-methyl-1,2,4-oxadiazol-5-yl)ethyl]-6-oxo-1,6-dihydropyridine-3-carboxamide To a solution of the sodium chloride salt of 5-(4-fluorophenyl)-1-(3-hydroxy-3-methylbutan-2-yl)-6-oxo-1,6-dihydropyridine-3-carboxylic acid (177 mg, 0.46 mmol) in N,N-dimethylformamide (2 mL) were added (1R)-1-(3-methyl-1,2,4-oxadiazol-5-yl)ethanamine hydrochloride salt (110 mg, 0.55 mmol), EDC (105 mg, 0.55 mmol), 1-hydroxy-7-azabenzotriazole (6 mg, 0.05 mmol) and N-methylmorpholine (0.121 mL, 1.10 mmol). The reaction mixture was stirred at ambient temperature. After 18 h, water was added. Purification by reverse phase HPLC (C-18, 95% water/acetonitrile→15% water/acetonitrile with 0.1% trifluoroacetic acid) gave the title compound. HRMS 429.1973 (M+1).

Examples 5.135 and 5.136

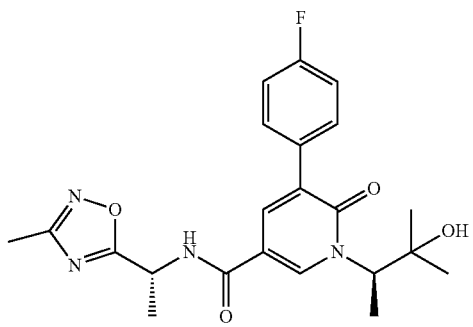

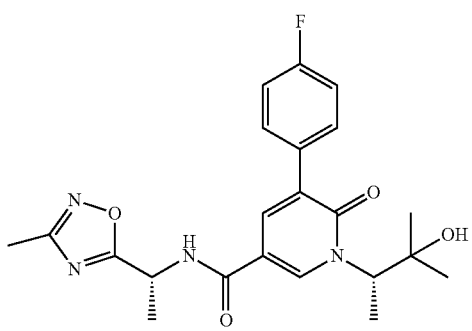

5-(4-Fluorophenyl)-1-[(2R)-3-hydroxy-3-methylbutan-2-yl]-N-[(1R)-1-(3-methyl-1,2,4-oxadiazol-5-yl)ethyl]-6-oxo-1,6-dihydropyridine-3-carboxamide and 5-(4-Fluorophenyl)-1-[(2S)-3-hydroxy-3-methylbutan-2-yl]-N-[(1R)-1-(3-methyl-1,2,4-oxadiazol-5-yl)ethyl]-6-oxo-1,6-dihydropyridine-3-carboxamide Purification of the two diastereomers by chiral chromatography (Whelk-O1, 2.1 cm×25 cm, 60% heptane and 40% isopropanol, 28 mL/min) gave the title compounds. EXAMPLE 5.135: HRMS 429.1928 (M+1). $^1$H NMR (400 MHz, DMSO): δ 9.05 (d, J=7.4 Hz, 1H); 8.46 (s, 1H); 8.13 (s, 1H); 7.76 (t, J=6.9 Hz, 2H); 7.25 (t, J=8.7 Hz, 2H); 5.76 (s, 1H); 5.35 (t, J=7.2 Hz, 1H); 5.15 (d, J=8.1 Hz, 1H); 4.95 (s, 1H); 2.33 (s, 3H); 1.59 (d, J=7.2 Hz, 3H); 1.39 (d, J=7.1 Hz, 3H); 1.25 (s, 3H); 0.91 (s, 3H). Example 5.136: HRMS 429.1931 (M+1). $^1$H NMR (400 MHz, DMSO): δ 9.03 (d, J=7.2 Hz, 1H); 8.47 (s, 1H); 8.14 (s, 1H); 7.76 (t, J=6.8 Hz, 2H); 7.25 (t, J=8.7 Hz, 2H); 5.35 (t, J=7.2 Hz, 1H); 5.15 (d, J=8.1 Hz, 1H); 4.94 (s, 1H); 2.33 (s, 3H); 1.59 (d, J=7.1 Hz, 3H); 1.39 (d, J=7.1 Hz, 3H); 1.25 (s, 3H); 0.91 (s, 3H).

Assay

In Vivo Rat Visceral Pain Model

Male Sprague-Dawley rats, weighing 150-180 g (max. range per experiment=40 g) at the beginning of the experiments. Animals will be delivered to the laboratory at least 5 days before the experiments during which time they are acclimatized to laboratory conditions. Rats will be housed in groups of 4, 5 or 6 in macrolon cages (41×25×14 cm or 44×28×19 cm) on wood with free access to food and water until tested (or as indicated otherwise). The animal house will be maintained under artificial lighting (12 hours) between 7.00 and 19.00 in a controlled ambient temperature of 21±3° C., and relative humidity maintained at 40-70%. Information related to any clinical signs and mortality will be archived with the study materials.

After overnight food-deprivation, male Sprague-Dawley rats are slightly anesthetized (isoflurane) and injected with 1% acetic acid into the colon (1.5 ml) using a cannula of 5 cm in length. After a recovery period of 75 minutes, rats are again slightly anesthetized (isoflurane) and a latex balloon of 1.5 cm in length tightly attached to a catheter is inserted via the anus into the descending colon and rectum. Anesthesia is then immediately discontinued. 15 minutes later, the test substance is administered p.o. 60 minutes after administration, the balloon is filled with 1.2 ml of water and the number of abdominal contractions is counted for 10 minutes.

10 rats are studied per group. The test is performed blind. The test substance will be evaluated at 3 doses, and compared with the vehicle group. Rats will be euthanized at the end of the experiments by exposure to a mixture of $O_2/CO_2$ (20%/80%) followed by $CO_2$. Data will be analyzed by comparing treated groups with vehicle control using Mann Whitney U tests.

In Vivo L5 Spinal Nerve Ligation Model a. Surgery and Post-Operative Care

For the spinal nerve ligation (SNL) procedure, male Sprague Dawley rats (100-200 g; Harlan) are anesthetized using isoflurane (1-5%; inhalation). Using aseptic technique, a dorsal midline incision is made from approximately spinal nerve L3 to S2. A combination of sharp and blunt dissection is used to expose the L6/S1 posterior interarticular process. The L6 transverse process is visualized and removed, and the L4 and L5 spinal nerves are exposed distal to their emergence from the intervertebral foramina. The L5 nerve is then tightly ligated with 6-0 silk suture. The muscle is closed with 4-0 absorbable suture and the skin is closed with wound clips. Postoperative monitoring is carried out to assure that animals are exposed to the least amount of pain as possible. Animals are housed in pairs on bedding and are monitored (2×) daily for three days post-operatively by Laboratory Animal Resource staff and then daily by investigator for any signs of possible distress.

b. Behavioral Testing

Prior to surgery, rats are tested for pre-surgery mechanical hind paw withdrawal thresholds by applying a series of calibrated von Frey filaments (0.25-15 g) to the left hind paw and determining the median withdrawal threshold using the Dixon "up-down" method (Chaplan et al., J Neurosci Meth 53:55, 1994). Rats are placed in individual plastic chambers on an elevated mesh galvanized steel platform and allowed to acclimate for 60 min. Pre-surgery mechanical hind paw withdrawal thresholds are determined, and rats having a threshold <15 g are excluded from the study. Following determination of pre-surgery withdrawal thresholds, rats undergo the SNL procedure described above. Between 28-35 days following the surgical procedure, rats are tested for post-surgery thresholds using the procedure described above, and animals displaying a hind paw withdrawal threshold <4.0 g are considered allodynic (i.e. mechanical hypersensitivity). Effects of test compounds on SNL-induced mechanical hypersensitivity are determined by dosing the compound along with a vehicle control group and a group receiving the positive comparator pregabalin (20 mg/kg, p.o.). Efficacy in the SNL model is evaluated by determining the % reversal of mechanical hypersensitivity using the formula:

$$\% \text{ reversal} = \frac{(\text{post- drug threshold} - \text{post- surgery threshold})}{\text{pre- surgery threshold} - \text{post- surgery threshold}} \times 100$$

At the conclusion of the study, all rats are euthanized using $CO_2$ and plasma and brain tissue are collected for bioanalytical analysis of drug exposures.

In Vivo Complete Freunds Adjuvant (CFA) Model

Male Sprague Dawley rats (300-400 g; Charles River) receive an intradermal injection of CFA (200 ul, 0.5 mg/ml) into the plantar aspect of the left hind paw and are subsequently returned to their cages where they are maintained on soft bedding. 72 hrs following CFA injection rats are tested for post-CFA mechanical hind paw withdrawal thresholds by wrapping the rat in a towel and placing the hind paw (either left or right) in a modified Randall-Sellito paw pinch apparatus (Stoelting, Wood Dale, Ill.). A plastic bar attached to a lever is placed on the dorsum of the hind paw, and an increasing force is applied to the hind paw until the rat vocalizes or pulls its hind paw away from the bar. The rat's hind paw withdrawal threshold is recorded at that point. The mechanical stimulus is applied to each hind paw 2 times, and the average post-CFA mechanical hind paw withdrawal thresholds are determined for both the left and right hind paw. Following determination of post-CFA withdrawal thresholds, rats receive test compound, vehicle, or the positive comparator naproxen (30 mg/kg, p.o.), and effects of compounds on withdrawal thresholds for the inflamed (CFA) hind paw are determined. Efficacy in the CFA model is evaluated by determining the % reversal of mechanical hypersensitivity using the formula:

$$\% \text{ reversal} = \frac{(\text{post-drug } threshold_{left\ hind\ paw} - \text{post-}CFA\ threshold_{left\ hind\ paw})}{(\text{post-}CFA\ threshold_{right\ hind\ paw} - \text{post-}CFA\ threshold_{left\ hind\ paw})} \times 100$$

At the conclusion of the study, all rats are euthanized using $CO_2$ and plasma and brain tissue are collected for bioanalytical analysis of drug exposures.

Cystometry in Normal Healthy Rats

Female Sprague-Dawley rats weighed 250-350 g were housed in a temperature- and light (12-h light/dark cycle)-controlled room, and were allowed access to food and water ad libitum. The animals were anesthetized with urethane (1.0 g/kg, i.p.). Supplemental urethane was given if necessarily. A lower abdominal midline incision was made to expose the bladder, and a polyethylene catheter (PE-50) was inserted into the bladder dome for recording the intravesical pressure and intravesical infusion of physiological saline at the rate of 0.05 ml/min. The intravesical pressure was measured using a pressure transducer, and signal was recorded using a multiple channel data acquisition system (Power lab, AD Instruments, Biopac systems, Colorado Springs, Colo.) at a sampling rate of 10 Hz. After confirming stable inter-micturtion interval and micturition pressure by intravesical infusion of saline, the drugs were administered intravenously (0.25 ml/kg). Inter-micturition interval (functional bladder capacity) and micturition pressure (maximum intravesical pressure) were obtained from micturitions prior to dosing (baseline) and between 5 to 30 min after dosing using Chart program (v5.5.4, AD Instruments), and calculated the ratio to baseline.

Cystometry in Rat Acetic Acid-Induced Hyper-Reflexia Model

Female Sprague-Dawley rats weighed 250-350 g were housed in a temperature- and light (12-h light/dark cycle)-controlled room, and were allowed access to food and water ad libitum. The animals were anesthetized with urethane (1.0 g/kg, i.p.). Supplemental urethane was given if necessarily. A lower abdominal midline incision was made to expose the bladder, and a polyethylene catheter (PE-50) was inserted into the bladder dome for recording the intravesical pressure and intravesical infusion at the rate of 0.05 ml/min. The intravesical pressure was measured using a pressure transducer, and signal was recorded using a multiple channel data acquisition system (Power lab, AD Instruments, Biopac systems, Colorado Springs, Colo.) at a sampling rate of 10 Hz. After confirming stable inter-micturtion interval and micturition pressure by intravesical infusion of saline, 0.25% of acetic acid-saline solution was infused at the same infusion rate. After 30-60 min, drugs were intravenously infused using infusion pumps at a rate of 10 µl/min. Intermicturition interval (functional bladder capacity) and micturition pressure (maximum intravesical pressure) were obtained from micturitions prior to dosing (baseline) and between 30 to 45 min after starting drug infusion using Chart program (v5.5.4, AD Instruments), and calculated the ratio to baseline.

Generation of a Human $P2X_3$ and $P2X_{2/3}$ Stable Cell Line—

Human $P2X_3$ receptor cDNA (Accession number NM_002559) was subcloned as a 5'XhoI and 3'HindIII fragment into the expression vector pcDNA5/FRT (Invitrogen). Human $P2X_2$ receptor cDNA (Accession number NM_174873) was subcloned as a 5'EcoRI and 3'NotI fragment into the expression vector pIRESneo2 (BD Biosciences Clontech). The human $P2X_3$ expression construct was transfected using Lipofectamine 2000 (Invitrogen) into Flp-in—293 cells (Invitrogen) according to the manufacturer's directions. Cells positive for flp-mediated recombination of rhesus $P2X_3$ were selected using 150 µg/ml hygromycin. The stable human $P2X_3$ cell line was co-transfected with the human $P2X_2$ expression construct using Lipofectamine 2000 as above and co-transfected cells selected using 100 mg/ml hygromycin and 1 mg/ml G418. The stable $P2X_3$ cell line was propagated in DMEM, 10% FBS, 100 µg/ml hygromycin, and 100 units/ml penicillin and 100 µg/ml streptomycin, and maintained at 37° and 95% humidity. The stable $P2X_{2/3}$ cell line was propagated as above with the addition of 500 µg/ml G418.

Intracellular Calcium Measurement to Assess Antagonist Affinity—

A fluorescent imaging plate reader (FLIPR; Molecular Devices) was used to monitor intracellular calcium levels using the calcium-chelating dye Fluo-4 (Molecular Probes). The excitation and emission wavelengths used to monitor fluorescence were 488 nm and 530 nm, respectively. Cells expressing either human $P2X_3$ or human $P2X_{2/3}$ were plated at a density of 20,000 cells/well (20 µl/well) in 384-well black-walled plates approximately 20 hours before beginning the assay. On the day of the assay 20 µl of loading buffer (Hank's balanced salt solution, 2.5 mM $CaCl_2$, 20 mM HEPES, 0.1% BSA, 2.5 mM probenecid, TR-40, Fluo-4, and 138 mM NMDG substituted for NaCl) is added and cells dye-loaded for 60 min in the dark at room temperature. Ten minutes prior to adding agonist, the antagonist was added in a volume of 10 µl and allowed to incubate at room temperature. During this period fluorescence data is collected at 3 sec intervals followed by 10 sec intervals. The agonist, α,β-meATP, is added at a 6× concentration ([α,β-meATP]$_{final}$=EC$_{50}$). Following agonist addition fluorescence was measured at 5 sec intervals and analyzed based on the increase in peak relative fluorescence units (RFU) compared to the basal fluorescence. Peak fluorescence was used to determine the inhibitory effect at each concentration of antagonist by the following equation:

% Inhibition=100*(1−((RFU$_{(drug)}$−RFU$_{(control)}$)/(RFU$_{(DMSO\ only)}$−RFU$_{(control)}$)))

In vitro Electrophysiological Assay—

Cells expressing human $P2X_3$ receptors were grown to a confluence of 65-85% 20 to 32 hours prior to assay. The cells were dissociated with trypsin, centrifuged, and resuspended in bath solution at a cell density of 1×10$^6$ cells/ml and loaded onto PatchXpress. The bath solution contained 150 mM NaCl, 4 mM KCl, 2 mM $CaCl_2$, 1.2 mM $MgCl_2$, 10 mM HEPES, and 11.1 mM glucose, at pH 7.2. The intracellular solution contained either 140 mM K-aspartate, 20 mM NaCl, 5 mM HEWS, 10 mM EGTA, at pH 7.2 or 30 mM CsCl, 5 mM HEPES, 10 mM EGTA, 120 mM CsF, 5 mM NaF, 2 mM MgCl2, pH=7.3 with CsOH. Agonist stock solutions were prepared in $H_2O$ and diluted in bath solution prior to use. All antagonists were prepared as 10 mM stock solutions in DMSO and diluted in bath solution prior to use. All experiments were performed on cells under the whole-cell patch clamp configuration at room temperature. Up to 16 individual cells could be patch clamped simultaneously on the PatchXpress instrument. A baseline response was established by repeated CTP (100 μM; for 2 sec.) followed by antagonist incubation for 2 min. in the absence of CTP. After antagonist preincubation 100 μM CTP and antagonist were co-administered to determine the inhibitory effect of the antagonist. These steps were then repeated on the same cell with a range of concentrations of the antagonist. A maximum of five concentrations of antagonist were tested on any individual cell. The control $P2X_3$ current amplitude ($I_{P2X3-(control)}$) was taken as an average of the peak current amplitude from the last two agonist additions prior to incubation with an antagonist. The peak $P2X_3$ current amplitude in the presence of an antagonist ($I_{P2X3-(drug)}$) was used to calculate the inhibitory effect at each concentration of the antagonist according to the following equation:

$$\% \text{ inhibition of } P2X_3 = 100 * (I_{P2X3-(control)} - I_{P2X3-(drug)})/I_{P2X3-(control)}$$

Each concentration of an antagonist was tested on at least two independent cells. The concentration of drug required to inhibit $P2X_3$ current by 50% ($IC_{50}$) was determined by fitting of the Hill equation to the averaged % inhibition data at each concentration:

$$\% \text{ of Control} = 100 \cdot (1 + ([\text{Drug}]/IC_{50})^p)^{-1}$$

In Vitro Electrophysiological Assay for $P2X_{2/3}$—

$P2X_{2/3}$ was assayed as above with two protocol modifications: 1) 30 μM α,β-meATP used as agonist; and 2) current amplitude was measured at the end of 2-second agonist application. Using the assays described herein the compounds of this invention were found to be active for the P2X3 receptor. The compounds of formula I have an $IC_{50}$ activity of 100 μM or less for the P2X3 receptor. Many of the compounds of formula I disclosed herein were found to have an $IC_{50}$ of less than 200 nM. For example, the compounds below have $IC_{50}$<250 nM in the "Intracellular Calcium Measurement to Assess Antagonist Affinity" assay. In particular, compound 1.62 has an $IC_{50}$=23 nM; compound 2.1 has an $IC_{50}$=165 nM; compound 3.22 has an $IC_{50}$=42 nM; and compound 5.61 has an $IC_{50}$=48 nM.

What is claimed:

1. A compound of structural formula I:

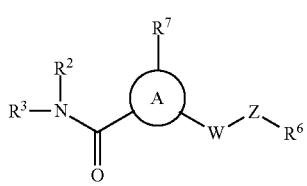

I or pharmaceutically acceptable salts and individual enantiomers and diastereomers thereof wherein:

A represents pyridinyl, or pyridinonyl;

W and Z independently are absent or represent $C(R^2)_2$, —O—, $NR^2$, CO, or $SO_{0-2}$;

$R^2$ represents H, $C_{1-6}$ alkyl, $CF_3$, OH, $CHF_2$, or $CH_2F$;

$R^3$ represents $CR^2R^4R^5$, $(CH_2)_nC_{3-10}$ cycloalkyl, $(CH_2)_nC_{6-10}$ aryl, $(CH_2)_nC_{5-10}$ heterocycle, said cycloalkyl, and heterocyclyl optionally substituted with 1 to 3 groups of $R^a$;

or $R^2$ and $R^3$ can be combined with the nitrogen to which they are attached to form a $C_{5-10}$ heterocyclyl optionally substituted with 1 to 3 groups of $R^a$;

$R^4$ and $R^5$ independently represent H, $(CH_2)_nOR^2$, $CHF_2$, $(CH_2)_nCF_3$, $(CH_2)_nC_{5-10}$ heterocyclyl, $(CH_2)_nC_{6-10}$ aryl, $C_{3-10}$ cycloalkyl, $C_{1-6}$ alkoxy, $C_{2-6}$ alkenyl, $C(O)_{1-2}R^2$, or $C_{1-6}$ alkyl; said alkyl, cycloalkyl, heterocyclyl and aryl optionally substituted with 1 to 3 groups of $R^a$;

$R^6$ represents hydrogen, $OR^2$, —O—, $CF_3$, $C(R^2)_2OR^2$, $C_{1-6}$ alkyl, $C_{2-6}$ alkenyl, $C_{2-6}$ alkynyl, $C_{3-10}$ cycloalkyl, $(CH_2)_nC_{6-10}$ aryl, $(CH_2)_nC_{5-10}$ heterocyclyl, said alkyl, aryl and heterocyclyl optionally substituted with 1 to 3 groups of $R^a$;

$R^7$ represents $C_{1-6}$ alkyl, $C_{3-10}$ cycloalkyl, $(CH_2)_nC_{5-10}$ heterocyclyl, or $(CH_2)_nC_{6-10}$ aryl, said alkyl, cycloalkyl, heterocyclyl and aryl optionally substituted with 1 to 3 groups of $R^a$;

$R^a$ represents $C_{1-6}$ alkyl, halogen, hydroxyl, $OR^2$ $(CH_2)_nCF_3$, —O—, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $C(O)OR^2$, $SO_2R^2$, $OR^2$, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN; and n represents 0 to 4, provided that when A is pyridinonyl $WZR^6$ is not hydrogen or when A is pyridinyl, W is CO, Z is $NR^2$ (where $R^2$ in $NR^2$ is alkyl), $R^2$ is hydrogen or alkyl, and $R^3$ is alkyl, then $R^6$ is not hydrogen or alkyl.

2. The compound according to claim 1 wherein $R^2$ is hydrogen, and $R^7$ is represented by structural formula Ia:

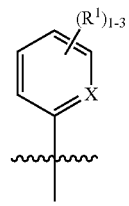

Ia

Wherein X is N or CH; and $R^1$ represents H, $C_{1-6}$ alkyl, halogen, $(CH_2)_nCF_3$, $C_{3-10}$ cycloalkyl, $C(R^2)_2OH$, —O—, CN, $(CH_2)_nOR^2$, $(CH_2)_nC_{5-10}$ heterocyclyl, $(CH_2)_nC_{6-10}$ aryl, or $C_{1-6}$ alkoxy; said alkyl, cycloalkyl, heterocyclyl and aryl optionally substituted with 1 to 3 groups of $C_{1-6}$ alkyl, halogen, hydroxyl, $(CH_2)_nCF_3$, or CN.

3. The compound according to claim 2 wherein X is N.

4. The compound according to claim 2 wherein X is CH.

5. The compound according to claim 2 wherein Ia is linked to a carbon atom on A.

6. The compound according to claim 1 wherein A is pyridyl.

7. The compound according to claim 1 wherein A is pyridinonyl.

8. A compound according to claim 1 represented by structural formula II:

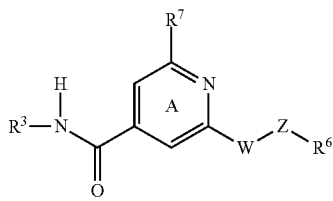

II or pharmaceutically acceptable salts and individual enantiomers and diastereomers thereof:
wherein W and Z are absent, $R^7$ is $(CH_2)_n C_{6-10}$ aryl, or $(CH_2)_n C_{6-10}$ heterocyclyl optionally substituted with 1 to 3 groups of $R^a$, $R^6$ is hydrogen, —O—, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_n C_{6-10}$ aryl, or $(CH_2)_n C_{6-10}$ heterocyclyl, said alkyl, aryl and heterocyclyl optionally substituted with 1 to 3 groups of $R^a$.

9. A compound according to claim 1 represented by structural formula IV:

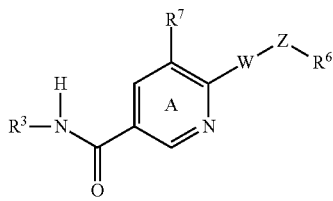

IV or pharmaceutically acceptable salts and individual enantiomers and diastereomers thereof:
wherein W and Z are absent, $R^7$ is $(CH_2)_n C_{6-10}$ aryl, or $(CH_2)_n C_{6-10}$ heterocyclyl said aryl and heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_n C_{6-10}$ aryl, or $(CH_2)_n C_{6-10}$ heterocyclyl, said alkyl, aryl and heterocyclyl optionally substituted with 1 to 3 groups of $R^a$.

10. A compound according to claim 1 represented by structural formula V:

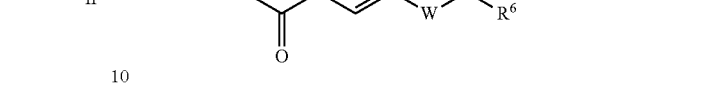

V or pharmaceutically acceptable salts and individual enantiomers and diastereomers thereof:
wherein W and Z are absent, $R^7$ is $(CH_2)_n C_{6-10}$ aryl, or $(CH_2)_n C_{6-10}$ heterocyclyl optionally substituted with 1 to 3 groups of $R^a$, $R^6$ is —O—, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_n C_{6-10}$ aryl, or $(CH_2)_n C_{6-10}$ heterocyclyl, said alkyl, aryl and heterocyclyl optionally substituted with 1 to 3 groups of $R^a$.

11. A compound according to claim 1 represented by structural formula VI:

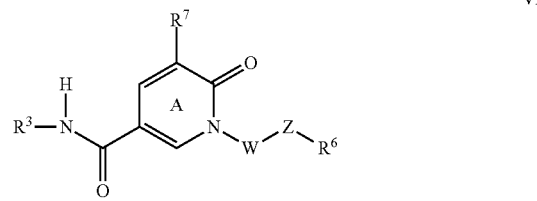

VI or pharmaceutically acceptable salts and individual enantiomers and diastereomers thereof:
wherein W and Z are absent, $R^7$ is $(CH_2)_n C_{6-10}$ aryl, or $(CH_2)_n C_{6-10}$ heterocyclyl optionally substituted with 1 to 3 groups of $R^a$, $R^6$ is hydrogen, $C_{1-6}$ alkyl, $OR^2$, $(CH_2)_n$morpholinyl, $(CH_2)_n$pyridyl, $(CH_2)_n$piperidinyl, $(CH_2)_n$oxazolyl, $(CH_2)_n$isoxazolyl, $(CH_2)_n$phenyl, $(CH_2)_n$piperidinyl, $(CH_2)_n$imidazolyl, $(CH_2)_n$pyrimidinyl, cyclopropyl, cyclobutyl, all optionally substituted with 1 to 3 groups of $R^a$, and $R^3$ is $CR^2R^4R^5$ wherein $R^2$ of $CR^2R^4R^5$ is hydrogen, and one of $R^4$ and $R^5$ is $C_{1-6}$ alkyl or hydrogen and the other is $(CH_2)_n C_{6-10}$ aryl, or $(CH_2)_n C_{6-10}$ heterocyclyl, said alkyl, aryl and heterocyclyl optionally substituted with 1 to 3 groups of $R^a$.

12. The compound according to claim 11 wherein $R^7$ is phenyl, pyridinyl, morpholinyl, pyrimidinyl, imidazolyl, or oxazolyl any one of which is optionally substituted with 1 to 3 groups of $R^a$, $R^2$ of $CR^2R^4R^5$ is hydrogen, and one of $R^4$ and $R^5$ of $CR^2R^4R^5$ is $C_{1-6}$ alkyl or hydrogen and the other is $(CH_2)_n$phenyl, $(CH_2)_n$pyridyl, $(CH_2)_n$pyrimidinyl, $(CH_2)_n$triazolyl, pyrazinyl, or $(CH_2)_n$oxadiazolyl, said phenyl, pyridyl, pyrimidinyl, triazolyl, pyrazinyl and oxadiazolyl optionally substituted with 1 to 3 groups of $R^a$.

13. The compound according to claim 12 wherein $R^7$ is an optionally substituted phenyl, $R^2$ of $CR^2R^4R^5$ is hydrogen, and one of $R^4$ and $R^5$ of $CR^2R^4R^5$ is $C_{1-6}$ alkyl or hydrogen and the other is optionally substituted $(CH_2)_n$oxadiazolyl, said oxadiazolyl optionally substituted with 1 to 3 groups of $R^a$, and $R^6$ is an optionally substituted $C_{1-6}$ alkyl.

14. A compound represented in Tables 1 through 5, wherein A is pyridinyl or pyridinonyl or pharmaceutically acceptable salts and individual enantiomers and diastereomers thereof.

15. A compound according to claim 14 which is:

2-(2-Fluoro-4-methylphenyl)-6-morpholin-4-yl-N-[(1S)-1-(4H-1,2,4-triazol-3-yl)ethyl]isonicotinamide;

2-(2,4-Difluorophenyl)-6-(1-hydroxy-1-methylethyl)-N-{(1R)-1-[1-oxido-6-(trifluoromethyl)pyridin-3-yl]ethyl}isonicotinamide;

2-(2,4-Difluorophenyl)-6-(2-methylpyrimidin-5-yl)-N-{(1R)-1-[1-oxido-6-(trifluoromethyl)pyridin-3-yl]ethyl}isonicotinamide;

N-{(1R)-1-[6-(1,1-Difluoroethyl)-1-oxidopyridin-3-yl]ethyl}-2-(2,4-difluorophenyl)-6-(2,2,2-trifluoro-1-hydroxyethyl)isonicotinamide;

6-Isopropyl-5'-methyl-N-{(1R)-1-[2-(trifluoromethyl)pyrimidin-5-yl]ethyl}-2,2'-bipyridine-4-carboxamide;

N-[(1R)-1-(3-Methyl-1,2,4-oxadiazol-5-yl)ethyl]-2,6-bis(4-methylphenyl)pyrimidine-4-carboxamide;

5-(2,4-Difluorophenyl)-N-{(1R)-1-[1-oxido-6-(trifluoromethyl)pyridin-3-yl]ethyl}nicotinamide;

5-(4-Fluorophenyl)-6-isopropoxy-N-[(1R)-1-(3-methyl-1,2,4-oxadiazol-5-yl)ethyl]nicotinamide;

5-(4-fluorophenyl)-1-isopropyl-N-[(1R)-1-(3-methyl-1,2,4-oxadiazol-5-yl)ethyl]-6-oxo-1,6-dihydropyridine-3-carboxamide;

5-(2-Fluoro-4-methylphenyl)-N-[(1R)-1-(3-methyl-1,2,4-oxadiazol-5-yl)ethyl]nicotinamide 1-oxide;

3-(4-Fluorophenyl)-N-[(1R)-1-(3-methyl-1,2,4-oxadiazol-5-yl)ethyl]-2-oxo-2H-1,2'-bipyridine-5-carboxamide;

5-(4-Fluorophenyl)-1-(3-hydroxy-3-methylbutan-2-yl)-N-[(1R)-1-(3-methyl-1,2,4-oxadiazol-5-yl)ethyl]-6-oxo-1,6-dihydropyridine-3-carboxamide;

5-(4-Fluorophenyl)-1-[(2R)-3-hydroxy-3-methylbutan-2-yl]-N-[(1R)-1-(3-methyl-1,2,4-oxadiazol-5-yl)ethyl]-6-oxo-1,6-dihydropyridine-3-carboxamide;

5-(4-Fluorophenyl)-1-[(2S)-3-hydroxy-3-methylbutan-2-yl]-N-[(1R)-1-(3-methyl-1,2,4-oxadiazol-5-yl)ethyl]-6-oxo-1,6-dihydropyridine-3-carboxamide or pharmaceutically acceptable salts and individual enantiomers and diastereomers thereof.

16. A pharmaceutical composition comprising an inert carrier and an effective amount of a compound according to claim 1.

* * * * *